(12) United States Patent
Saka et al.

(10) Patent No.: US 7,947,722 B2
(45) Date of Patent: May 24, 2011

(54) IMIDAZOLIDINONE DERIVATIVE, METHOD OF PRODUCING THE SAME AND METHOD OF PRODUCING OPTICALLY ACTIVE AMINO ACID

(75) Inventors: Yasuhiro Saka, Takasago (JP); Akio Fujii, Takasago (JP); Kazumi Okuro, Takasago (JP); Masaru Mitsuda, Takasago (JP)

(73) Assignee: Kaneka Corporation, Osaka (JP)

( * ) Notice: Subject to any disclaimer, the term of this patent is extended or adjusted under 35 U.S.C. 154(b) by 72 days.

(21) Appl. No.: 12/309,729

(22) PCT Filed: May 14, 2007

(86) PCT No.: PCT/JP2007/059826
§ 371 (c)(1),
(2), (4) Date: Jan. 28, 2009

(87) PCT Pub. No.: WO2008/012974
PCT Pub. Date: Jan. 31, 2008

(65) Prior Publication Data
US 2009/0209768 A1    Aug. 20, 2009

(30) Foreign Application Priority Data
Jul. 28, 2006 (JP) ................................ 2006-206431

(51) Int. Cl.
*A61K 31/4166*    (2006.01)
*C07D 233/32*    (2006.01)
(52) U.S. Cl. .................. 514/386; 548/316.4; 548/322.5
(58) Field of Classification Search ............... 548/316.4; 514/396
See application file for complete search history.

(56) References Cited

U.S. PATENT DOCUMENTS

| 4,280,008 A | 7/1981 | Schoellkopf et al. |
| 4,772,694 A | 9/1988 | Cooper |

FOREIGN PATENT DOCUMENTS

| JP | 53-79866 | 7/1978 |
| JP | 63-35571 | 2/1988 |

OTHER PUBLICATIONS

International Search Report dated Jun. 19, 2007 in the International (PCT) Application PCT/JP2007/059826 of which the present application is the U.S. National Stage.

Robert Fitzi et al., "Enantiomer Separation of (R,S)-2-(*tert*-Butyl)-3-methyl-4-imidazolidinone, a Chiral Building Block for Amino Acid Synthesis", Angew. Chem. Int. Ed., vol. 25, No. 4, pp. 345-346, 1986.
Dieter Seebach et al., "The Chiral Glycine Enolate Derivative from 1-Benzoyl-2-(*tert*-butyl)-3-methyl-1,3-imidazolidin-4-one is Alkylated in the 5-Position with Relative Topicity *lk*", Helvetica Chimica Acta, vol. 68, pp. 949-952, 1985.
Dieter Seebach et al., "EPC Synthesis with C,C Bond Formation via Acetals and Enamines", Modern Synthetic Methods, vol. 4, pp. 128-259, 1986.
Eusebio Juaristi et al., "Highly Diastereoselective Alkylation of 1-Benzoyl-2-alkyl-3-(1'-methylbenzyl) imidazolidin-4-ones", J. Org. Chem., vol. 60, pp. 6408-6415, 1995.
Karel M. J. Brands, et al., "Crystallization-Induced Diastereomer Transformations", Chemical Review, vol. 106, pp. 2711-2733, 2006.
Elmar Pfammatter et al., "Preparation of (R)- and (S)-2-Alkyl-2-amino-3-(methylamino)propanoic and Other 2,3-Diaminoalkanoic Acid Derivatives from a Chiral Imidazoline", Liebigs Annalen der Chemie, No. 12, pp. 1323-1336, 1991.
Form PCT/IB/338 together with International Preliminary Report on Patentability and translation of PCT Written Opinion dated Feb. 12, 2009 for International (PCT) Application No. PCT/JP2007/059826 of which the present application is the U.S. National Stage.
European Search Report issued Aug. 23, 2010 in corresponding European Application No. 07743261.
Fitzi, R. et al., "Resolution and use in alpha-amino acid synthesis of imidazolidinone glycine derivatives", Tetrahedron, vol. 44, No. 17, pp. 5277-5292, 1988.

*Primary Examiner* — Yong Chu
*Assistant Examiner* — Michael Barker
(74) *Attorney, Agent, or Firm* — Wenderoth, Lind & Ponack, L.L.P.

(57) ABSTRACT

The objective of the present invention is to provide an optically active imidazolidinone derivative widely usable for synthesizing an optically active amino acid, a method of easily producing the derivative, and a method of easily producing an optically active amino acid by using the derivative. The objective can be achieved by producing an optically active amino acid using a novel optically active imidazolidinone derivative represented by a general formula (3) and the like. According to the method of the present invention, an optically active imidazolidinone derivative can be obtained by preferential crystallization from a mixture of isomers of the imidazolidinone derivative. Therefore, an optically active amino acid can be easily and stereoselectively produced without cumbersome procedures required for the conventional methods, such as resolution of diastereomers, synthesis from an optically active amino acid and resolution of isomers by silica gel column chromatography.

23 Claims, No Drawings

IMIDAZOLIDINONE DERIVATIVE, METHOD OF PRODUCING THE SAME AND METHOD OF PRODUCING OPTICALLY ACTIVE AMINO ACID

TECHNICAL FIELD

The present invention relates to an optically active imidazolidinone derivative which is a chiral glycine synthon useful for producing an optically active amino acid. Further, the present invention relates to a method of producing the derivative, and a method of producing an optically active amino acid using the derivative. An optically active amino acid is an important intermediate in terms of production of a pharmaceutical product, an agricultural agent, a chemical product or the like.

BACKGROUND ART

An optically active amino acid, particularly an optically active unnatural amino acid which does not exist in nature, is an important constituent factor for a pharmaceutical product, an agricultural agent, a chemical product or the like. With respect to an optically active imidazolidinone derivative as a chiral glycine synthon developed for synthesizing such an unnatural amino acid, following synthetic methods are conventionally known.
  i) A method of synthesizing the derivative from a glycinamide derivative and pivalaldehyde (Non-patent Document 1)
  ii) A method of synthesizing the derivative from an optically active serinamide derivative and pivalaldehyde (Non-patent Document 2)
  iii) A method of synthesizing the derivative from an optically active methioninamide derivative and pivalaldehyde (Non-patent Document 3)
  iv) A method of synthesizing the derivative from a chiral glycinamide derivative and pivalaldehyde (Non-patent Document 4)

However, the method i) is difficult to be industrially carried out, since a salt production and salt dissolution process is inevitably required in the method i) in which the produced optical isomers are resolved as mandelate salts thereof. Further, the method ii) is also difficult to be industrially carried out, since in the method ii) an optically active serine is used and it is necessary to oxidize and decarbonate the hydroxymethyl group thereof after forming an imidazolidinone ring. Furthermore, the method iii) is also difficult to be industrially carried out, since cumbersome procedures are required for the method iii) because of a plurality of induction processes from optically active methionine similarly to the case of ii). In the case of the method iv), since optically active glycinamide is used, the produced imidazolidinone derivatives are obtained as an isomeric mixture. Accordingly, the method iv) is similarly difficult to be industrially carried out, since it is required to purify the isomeric mixture by a silica gel column to obtain a pure single isomer. In addition, pivalaldehyde used in common for the methods i) to iv) is an expensive compound and use of the compound in industrial scale is not preferred.

Non-patent Document 1: Angew. Chem. Int. Ed., 1986, 345
Non-patent Document 2: Helv. Chim. Acta., 1985, 68, 949
Non-patent Document 3: Modern Synthetic Methods, 1986, 4, 128
Non-patent Document 4: J. Org. Chem., 1995, 60, 6408

DISCLOSURE OF THE INVENTION

In view of the above situation, an objective of the present invention is to provide an optically active imidazolidinone derivative widely usable for synthesizing an optically active amino acid without carrying out cumbersome procedures such as resolution of a salt of diastereomers, synthesis from an optically active amino acid and resolution of isomers by a silica gel column. Further, it is also an objective to provide a method of easily producing the derivative. Furthermore, it is also an objective to provide a method of easily producing an optically active amino acid using the derivative.

The inventors, having extensive investigations to solve the above problems, produced a mixture of novel imidazolidinone derivative isomers, and found that an optically active imidazolidinone derivative can be isolated by preferential crystallization from a solution of an isomeric mixture of the derivative. Further, the inventors found that a single isomer can be obtained by dynamic kinetic resolution, since isomerization takes place during preferential crystallization. Furthermore, the inventors found that an optically active amino acid can be synthesized by using the optically active derivative, and the findings led to completion of the present invention.

The present invention relates to an imidazolidinone derivative represented by the general formula (1):

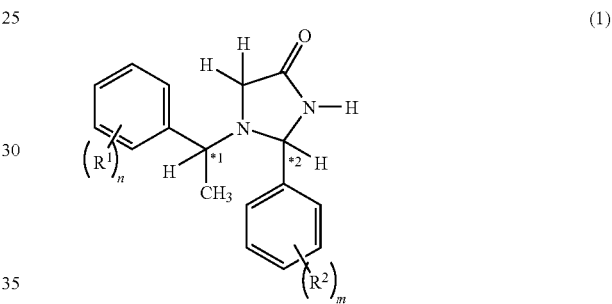

or an optically active form thereof,
wherein, n and m independently represents an integer of 0 to 5 representively indicating the numbers of substituent groups $R^1$ and $R^2$ on the benzene rings; $R^1$ and $R^2$ independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$ or $R^2$, the plural $R^1$ or $R^2$ may be all the same or different; *1 and *2 indicate asymmetric carbon atoms.

The present invention also relates to an imidazolidinone derivative represented by the general formula (2):

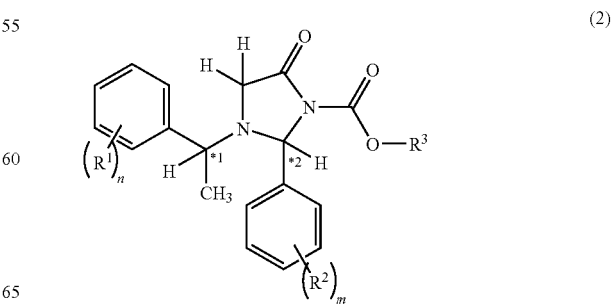

or an optically active form thereof, wherein, n, m, $R^1$, $R^2$, *1 and *2 are the same as described above; $R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms.

Further, the present invention also relates to an optically active imidazolidinone derivative represented by the general formula (3):

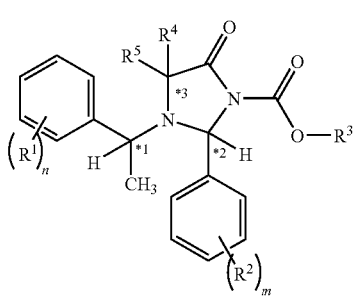
(3)

wherein, n, m, $R^1$, $R^2$, $R^3$ *1 and *2 are the same as described above; $R^4$ and $R^5$ are different, and represent a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and *3 indicates an asymmetric carbon atom.

Furthermore, the present invention relates to a method of producing the imidazolidinone derivative represented by the general formula (1), characterized in comprising a step of condensating an optically active glycinamide derivative represented by the general formula (4):

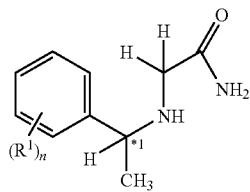
(4)

wherein, n, $R^1$ and *1 are the same as described above, with a substituted benzaldehyde represented by the general formula (5):

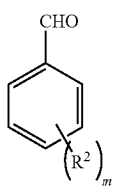
(5)

wherein, m and $R^2$ are the same as described above, in the presence of an acidic catalyst.

The present invention also relates to a method of crystallizing an optically active imidazolidinone derivative, characterized in comprising a step of crystallizing the imidazolidinone derivative represented by the general formula (1) using an organic solvent.

The present invention also relates to the method of crystallizing an optically active imidazolidinone derivative, characterized in that the optically active imidazolidinone derivative is crystallized while the imidazolidinone derivative is isomerized.

The present invention also relates to the method of crystallizing an optically active imidazolidinone derivative, characterized in that an acidic catalyst is used in the isomerization.

The present invention also relates to a method of producing the imidazolidinone derivative represented by the general formula (2), characterized in comprising a step of reacting the imidazolidinone derivative or optically active form thereof, represented by the general formula (1) with a halogenoformic acid ester represented by the general formula (6):

$R^3OCOX$ (6)

wherein, $R^3$ is the same as described above; and X represents a halogen atom, or a pyrocarbonic acid ester represented by the general formula (7):

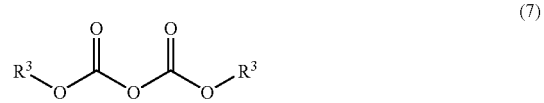
(7)

wherein, $R^3$ is the same as descried above and two $R^3$ are the same, in the presence of a base.

The present invention also relates to a method of crystallizing an optically active imidazolidinone derivative, characterized in comprising a step of crystallizing the imidazolidinone derivative represented by the general formula (2) by using an organic solvent.

The present invention also relates to a method of producing an optically active imidazolidinone derivative represented by the general formula (3), characterized in comprising a step of reacting the optically active imidazolidinone derivative represented by the general formula (2) with one or two kinds of electrophilic agents represented by the general formula (8):

$R^7Y$ (8)

wherein, $R^7$ represents an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and Y represents a leaving group, in the presence of a base.

The present invention also relates to a method of producing the optically active imidazolidinone derivative represented by the above general formula (3), characterized in comprising a step of reacting an optically active imidazolidinone derivative represented by the general formula (11):

(11)

[Structure of formula (11): imidazolidinone derivative with R⁷, phenyl(R¹)ₙ, CH₃ at *1, *2 H, N-C(=O)-O-R³, and phenyl(R²)ₘ substituents]

wherein, n, m, R¹, R², R³, R⁷, *1, *2 and *3 are the same as described above, with an electrophilic agent represented by the general formula (8)':

$$R^{7\prime}Y \qquad (8)'$$

wherein, R⁷' and Y are the same as described above, in the presence of a base.

The present invention also relates to a method of producing an optically active N-(1-substituted phenylethyl)amino acid derivative represented by the general formula (9):

(9)

[Structure of formula (9): R⁵, R⁴, COOH on *3 carbon, NH, phenyl(R¹)ₙ-CH(CH₃) at *1]

wherein, n, R¹, R⁴, R⁵, *1 and *3 are the same as described above, characterized in comprising a step of treating the optically active imidazolidinone derivative represented by the general formula (3) with an acid or a base in at least one of organic solvents and water.

The present invention also relates to a method of producing an optically active amino acid represented by the general formula (10):

(10)

[Structure of formula (10): R⁵, R⁴, COOH on *3 carbon, NH₂]

wherein, R⁴, R⁵ and *3 are the same as described above, characterized in comprising a steps of removing the substituent group on the nitrogen of the optically active imidazolidinone derivative represented by the general formula (3) to obtain an optically active amino acid amide represented by the general formula (12):

(12)

[Structure of formula (12): R⁵, R⁴, CONH₂ on *3 carbon, NH₂]

wherein, R⁴, R⁵ and *3 are the same as described above,
thereafter treating the amino acid amide with an acid or a base in at least one of organic solvents and water.

The present invention also relates to a method of producing an optically active imidazolidinone derivative represented by the general formula (14):

(14)

[Structure of formula (14): imidazolidinone derivative with OH-CH(R⁸) at *4, phenyl(R¹)ₙ, CH₃ at *1, *2 H, N-C(=O)-O-R³, and phenyl(R²)ₘ substituents]

wherein, n, m, R¹, R², R³, R⁸, *1, *2 and *3 are the same as described above; and in case that R⁸ is not a hydrogen atom, *4 indicates an asymmetric carbon atom, characterized in comprising a step of reacting the optically active imidazolidinone derivative represented by the general formula (2) with an aldehyde represented by the general formula (13):

$$R^8\text{—CHO} \qquad (13)$$

wherein, R⁸ represents a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms, in the presence of a base.

The present invention also relates to a method of producing an optically active N-(1-substituted phenylethyl)hydroxyamino acid derivative represented by the general formula (15):

(15)

[Structure of formula (15): OH, H on *4 carbon, R⁸, COOH on *3 carbon, NH, phenyl(R¹)ₙ-CH(CH₃) at *1]

wherein, n, R¹, R⁸, *1, *3 and *4 are the same as described above, characterized in comprising a step of treating the optically active imidazolidinone derivative represented by the general formula (14) with an acid or a base in at least one of organic solvents and water.

The present invention also relates to a method of producing an optically active hydroxyamino acid represented by the general formula (16):

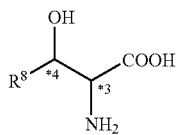

(16)

wherein, $R^8$, *3 and *4 are the same as described above, characterized in comprising a step of removing the substituent group on the nitrogen of the hydroxyamino acid derivative represented by the general formula (15).

The present invention also relates to a method of producing the optically active hydroxyamino acid represented by the general formula (16), characterized in comprising steps of removing the substituent group on the nitrogen of the optically active imidazolidinone derivative represented by the general formula (14) to synthesize an optically active hydroxyamino acid amide represented by the general formula (17):

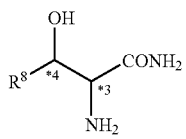

(17)

wherein, $R^8$, *3 and *4 are the same as described above; thereafter treating the hydroxyamino acid amide with an acid or a base in at least one of organic solvents and water.

Hereinafter, the present invention is described more in detail.

At first, the novel compound of the present invention is described.

The first present invention is an isomeric mixture of an imidazolidinone derivative or an optically active form of the derivative represented by the following general formula (1).

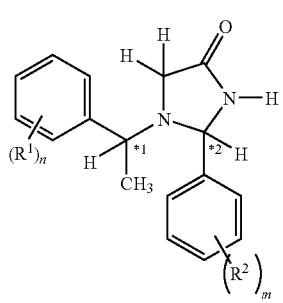

(1)

In the formula, $R^1$ and $R^2$ each independently represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group.

The example of the optionally substituted alkyl group having 1 to 18 carbon atoms includes a methyl group, an ethyl group, an n-propyl group, an isopropyl group, an n-butyl group, a t-butyl group, an n-pentyl group, a neopentyl group, a t-amyl group, an n-hexyl group, an n-heptyl group, an n-octyl group, an n-nonyl group, an n-decyl group and the like.

The example of the optionally substituted aralkyl group having 7 to 18 carbon atoms includes a benzyl group, a p-methoxyphenylmethyl group, a naphthylmethyl group and the like.

The example of the optionally substituted aryl group having 6 to 18 carbon atoms includes a phenyl group, a p-methoxyphenyl group, a naphthyl group, a p-nitrophenyl group and the like.

The example of the halogen atom includes a fluorine atom, a chlorine atom, a bromine atom and an iodine atom.

The example of the optionally substituted alkoxy group having 1 to 18 carbon atoms includes a methoxy group, an ethoxy group, an n-propyloxy group, an isopropyloxy group, an n-butyloxy group, a t-butyloxy group, a methoxymethyloxy group, a benzyloxymethyloxy group, a methylthiomethyloxy group, a 2-chloroethyloxy group, a 2-bromoethyloxy group and the like.

The above alkyl group, aralkyl group, aryl group and alkoxy group may be substituted with a halogen atom, an alkoxy group, a hydroxyl group, an aralkyloxy group, an alkylthio group, an alkylsilyloxy group, an arylalkylsilyloxy group and the like.

At the time of producing an optically active amino acid, $R^1$ and $R^2$ are preferably a chlorine atom, a methyl group, a methoxy group, an ethoxy group or a nitro group.

The reference character n represents an integer of 0 to 5 indicating the number of substituent groups on the benzene ring; and the substituent is $R^1$ as described above and the substitution manner is not particularly limited. The reference character m represents an integer of 0 to 5 indicating the number of substituent groups on the benzene ring; and the substituent is $R^2$ as described above and the substitution manner is not particularly limited.

In case that there are a plurality of $R^1$ and $R^2$, all $R^1$ may be the same or different and all $R^2$ may be the same or different.

The reference numeral *1 indicates an asymmetric carbon atom, and the absolute configuration may be R or S. In the specification, "the configuration is R" means that the isomer with the R configuration exists in large excess than the isomer with the S configuration at the asymmetric carbon atom, and "the configuration is S" means that the isomer with the S configuration exists in large excess than the isomer with the R configuration.

Further, the carbon atom of 2-position in the imidazolidinone ring of a compound represented by the general formula (1), that is, the carbon atom *2 positioned between the two nitrogen atoms, is an asymmetric carbon atom; the compound may be an optically active form or may be a racemic form containing an equimolecular amount of R and S isomers. Accordingly, the compound represented by the general formula (1) has at least one configuration selected from the group consisting of (*1, *2)=(R, R), (R, S), (S, R) and (S, S).

The second present invention is an isomeric mixture of an imidazolidinone derivative represented by the general formula (2):

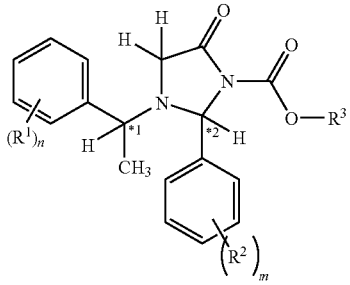

(2)

or an optically active form thereof.

The definitions and specific examples of $R^1$, $R^2$, n and m are the same as described above.

$R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms.

The example of the optionally substituted alkyl group having 1 to 18 carbon atoms includes a methyl group, an ethyl group, an n-propyl group, an isopropyl group, an n-butyl group, a t-butyl group, a 2,2,2-trichloroethyl group, an isobutyl group, a 2-chloroethyl group, a 1,1-dimethyl-2,2,2-trichloroethyl group, a 1-adamantyl group, a 2-trimethylsilylethyl group and the like.

The example of the optionally substituted alkenyl group having 2 to 18 carbon atoms includes an ally group, a vinyl group, a 3-butenyl group, a 2-methyl-2-propenyl group, a 3-phenyl-2-propenyl group, a 3-(p-nitrophenyl)-2-propenyl group and the like.

The example of the optionally substituted alkynyl group having 2 to 18 carbon atoms includes a propynyl group, a 2-butynyl group, a 3-butynyl group, a 2-pentynyl group and the like.

The example of the optionally substituted aralkyl group having 7 to 18 carbon atoms includes a benzyl group, a p-methoxyphenylmethyl group, a p-nitrophenylmethyl group, a p-bromophenylmethyl group, a p-chlorophenylmethyl group, a 2,4-dichlorophenylmethyl group, a naphthylmethyl group, a 9-fluorenylmethyl group and the like.

The example of the optionally substituted aryl group having 6 to 18 carbon atoms includes a phenyl group, a p-methoxyphenyl group, a naphthyl group and the like.

The above alkyl group, alkenyl group, alkynyl group, aralkyl group and aryl group may be substituted with a halogen atom, an alkoxy group, a hydroxyl group, an aralkyloxy group, an alkylthio group, an alkylsilyloxy group, an arylalkylsilyloxy group, a nitro group and the like.

At the time of producing the optically active amino acid, $R^3$ is preferably a methyl group, an ethyl group, an isopropyl group, an isobutyl group, a t-butyl group, an allyl group, a 2,2,2-trichloroethyl group, a benzyl group and a p-methoxyphenylmethyl group; more preferably a t-butyl group, a methyl group, an ethyl group, an allyl group and a benzyl group; and even more preferably a t-butyl group, an allyl group and a benzyl group.

The carbon atom of 2-position in the imidazolidinone ring of a compound represented by the general formula (2), that is, the carbon atom *2 positioned between the two nitrogen atoms, is an asymmetric carbon atom. The compound may be an optically active form or may be a racemic form containing an equimolecular amount of R and S isomers. Accordingly, the compound represented by the general formula (2) has at least one configuration selected from the group consisting of (*1, *2)=(R, R), (R, S), (S, R) and (S, S).

The third present invention is an imidazolidinone derivative represented by a general formula (3):

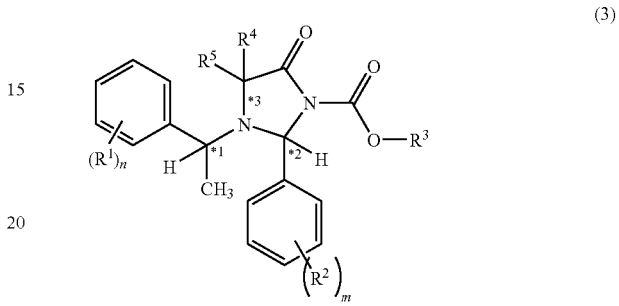

(3)

The definitions and specific examples of $R^1$, $R^2$, $R^3$, n and m are same as described above.

$R^4$ and $R^5$ are differently represent a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms.

The example of the carbon chain of the optionally substituted alkyl group having 1 to 30 carbon atoms includes a methyl group, an ethyl group, an n-propyl group, an isopropyl group, an n-butyl group, an isobutyl group, a 1-methyl-propyl group, a 2-methyl-propyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and the like; and the carbon chain may have a substituent group at any arbitrary position.

The kind of the substituent group includes a halogen atom, an alkoxy group, a hydroxyl group, an aralkyloxy group, an alkylthio group, an alkylsilyloxy group and an arylalkylsilyloxy group. The example thereof includes a 3-chloropropyl group, a 2-methoxyethyl group, a benzyloxymethyl group, a 2-benzyloxyethyl group, a 2-(mercaptomethyl)ethyl group, a 2-(t-butyldimethylsilyloxy)ethyl group, a 2-(t-butyldiphenylsilyloxy)ethyl group, a 2-trimethyhlsilyloxyethyl group and the like.

The example of the optionally substituted alkenyl group having 2 to 18 carbon atoms includes an allyl group, a vinyl group, a 3-butenyl group, a 2-methyl-2-propenyl group, a 3-phenyl-2-propenyl group and the like.

The example of the optionally substituted alkynyl group having 2 to 18 carbon atoms includes a propynyl group, a 2-butynyl group, a 3-butynyl group, a 2-pentynyl group and the like.

The example of the optionally substituted aralkyl group having 7 to 18 carbon atoms includes a benzyl group, a p-methoxyphenylmethyl group, a p-nitrophenylmethyl group, a p-bromophenylmethyl group, a p-chlorophenylmethyl group, a 2,4-dichlorophenylmethyl group, a naphthylmethyl group, a 1-indanoyl group, a diphenylmethyl group and the like.

The example of the optionally substituted aryl group having 6 to 18 carbon atoms includes a phenyl group, a p-methoxyphenyl group, a naphthyl group and the like.

At the time of producing the optically active amino acid, $R^4$ and $R^5$ are preferably a hydrogen atom, a methyl group, an ethyl group, a benzyl group, a propyl group, an allyl group, a propynyl group, a 1-methyl-propynyl group, a 2-methyl-propyl group, a benzyloxymethyl group, a 2-(mercaptomethyl) ethyl group, a p-methoxyphenylmethyl group, a 2-trimethylsilyloxyethyl group, a diphenylmethyl group.

In a compound represented by the general formula (3), the asymmetric center of carbon atom in 2-position of the imidazolidinone ring, i.e. *2, and the asymmetric center of carbon atom in 4-position of the imidazolidinone ring, i.e. *3, are determined to be R or S, respectively; and accordingly, the combination of the absolute configurations is exemplified by (*1, *2, *3)=(R, R, R), (R, R, S), (R, S, R), (R, S, S), (S, R, R), (S, R, S), (S, S, R) and (S, S, S). Among the examples, the compound is an optically active form having one of the absolute configurations.

In the general formulae (1), (2) and (3), an imidazolidinone derivative of which n=0 is preferable. More preferable is an imidazolidinone derivative of which n=0, $R^2$ is a chlorine atom, m=2, and the substituted positions are in 2,6 or 3,4; or an imidazolidinone derivative of which n=0, $R^2$ is a methyl group, m=3, and the substituted positions are in 2,4,6.

Particularly preferable is an imidazolidinone derivative in which n=0, $R^2$ is a chlorine atom, m=2, the substituted positions are in 2, 6 or 3,4, and $R^3$ is a t-butyl group;

an imidazolidinone derivative in which n=0, $R^2$ is a methyl group, m=3, the substituted positions are in 2,4,6, and $R^3$ is a t-butyl group;

an imidazolidinone derivative of which n=0, $R^2$ is a chlorine atom, m=2, the substituted positions are in 2,6, and $R^3$ is a benzyl group; or an imidazolidinone derivative of which n=0, $R^2$ is a chlorine atom, m=2, the substituted positions are in 2,6, and $R^3$ is an allyl group.

The imidazolidinone derivatives of the general formulae (1), (2) and (3) can be produced by the production method described below.

Next, the respective production steps is described in detail.

At first, a method of producing an imidazolidinone derivative represented by the general formula (1) is described.

The imidazolidinone derivative represented by the above general formula (1) can be produced, for example, by condensating an optically active glycinamide derivative represented by the general formula (4):

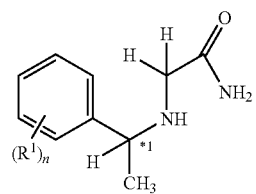

(4)

wherein, n, $R^1$ and *1 are the same as described above, with a substituted benzaldehyde represented by the general formula (5):

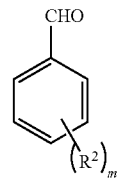

(5)

wherein, m and $R^2$ are the same as described above, in the presence of an acidic catalyst.

An optically active glycinamide represented by the general formula (4) can be easily produced by the method shown in Example 1 or the like. A substituted benzaldehyde represented by the general formula (5) is easily commercially available.

The amount of an optically active glycinamide derivative represented by the general formula (4) is not particularly limited; however, the amount is generally in a range of 0.1 to 10.0 molar equivalents based on molar equivalent of the substituted benzaldehyde (5). The amount is preferably in a range of 0.1 to 5.0 molar equivalents, and more preferably in a range of 0.1 to 3.0 molar equivalents.

The reaction is carried out in the presence of an acidic catalyst. The acidic catalyst is not particularly limited; however, the example includes mineral acids such as hydrochloric acid, hydrobromic acid, hydroiodic acid, sulfuric acid and nitric acid; sulfonic acids such as methanesulfonic acid, p-toluenesulfonic acid, camphorsulfonic acid and trifluoromethanesulfonic acid; and halogeno fatty acids such as trichloroacetic acid and trifluoroacetic acid; and the like. Among the examples, sulfonic acids are preferably used and p-toluenesulfonic acid is more preferable.

The amount of the acidic catalyst is not particularly limited; however, the amount to be used is preferably between 0.001 and 1.0 molar equivalent, more preferably in a range of 0.001 to 0.5 molar equivalents, and even more preferably in a range of 0.001 to 0.1 molar equivalents, based on molar equivalent of the substituted benzaldehyde (5) to be used.

Further, an organic solvent is generally used for the reaction. The solvent to be used is not particularly limited; however, the example includes aliphatic hydrocarbons such as n-hexane, n-heptane, n-octane, n-nonane, cyclohexane and methylcyclohexane; aromatic hydrocarbons such as benzene, toluene, xylene, mesitylene, chlorobenzene and o-dichlorobenzene; acetic acid esters such as methyl acetate, ethyl acetate, n-butyl acetate, t-butyl acetate and isopropyl acetate; ethers such as tetrahydrofuran, 1,4-dioxane, diisopropyl ether, t-butyl methyl ether and cyclopentyl methyl ether; nitriles such as acetonitrile and propionitrile; and amides such as N,N-dimethylformamide, N,N-dimethylacetamide, N,N-dibutylformamide and 1-methyl-2-pyrrolidone; and the like.

The solvent may be singly used, or two or more kinds of the solvents may be arbitrarily combined for use. Among the solvents, aliphatic hydrocarbons and aromatic hydrocarbons are preferable, and n-heptane, n-octane, cyclohexane, methylcyclohexane, benzene, toluene and chlorobenzene are more preferable, and toluene is much more preferable.

The amount of the solvent to be used is not particularly limited; however, the amount is generally in a range of 0.5 to 50 times volume based on a weight of a compound represented by the above formula (5). The amount is much preferably in a range of 1.5 to 25 times volume.

A reaction temperature is not particularly limited as long as condensation reaction of an optically active glycinamide derivative represented by the general formula (4) and a substituted benzaldehyde represented by the general formula (5) can be promoted; however, the temperature is preferably 0 to 150° C. and more preferably in a range of 30 to 150° C. A reaction time is not particularly limited; however, the reaction time is preferably 0.1 to 50 hours and more preferably 2 to 30 hours.

A thus produced imidazolidinone derivative represented by the general formula (1) has about 1:1 ratio of the isomers with respect to the carbon atom in 2-position of the imidazolidinone ring, i.e. the carbon atom positioned between the two nitrogen atoms.

The obtained compound represented by the general formula (1) may be used for the next step directly, or any one of the optically active forms may be preferentially crystallized from a solution of the imidazolidinone derivative isomeric mixture containing two or more optical isomers represented by the above formula (1), of which the optically active form may be used for the next step.

An organic solvent may be used for the crystallization. The solvent to be used is not particularly limited as long as the solubility of each isomer in the solvent is sufficiently different among a plurality of optical isomers, since the solubility difference of each optical isomer is utilized in the crystallization.

Illustrative example includes aliphatic hydrocarbons such as n-hexane, n-heptane, n-octane, n-nonane, cyclohexane and methylcyclohexane; aromatic hydrocarbons such as benzene, toluene, xylene, chlorobenzene and o-dichlorobenzene; acetic acid esters such as methyl acetate, ethyl acetate, n-butyl acetate, t-butyl acetate and isopropyl acetate; ethers such as tetrahydrofuran, 1,4-dioxane, diisopropyl ether, t-butyl methyl ether and cyclopentyl methyl ether; nitriles such as acetonitrile and propionitrile; amides such as N,N-dimethylformamide, N,N-dimethylacetamide and 1-methyl-2-pyrrolidone; and the like.

The solvent may be singly used, or two or more kinds of the solvents may be arbitrarily combined for use. Among the solvents, nitrites are preferable, and acetonitrile is more preferable.

The use amount of the solvent to be used is not particularly limited; however, the amount is generally in a range of 1 to 100 times volume based on the weight of the imidazolidinone derivative isomeric mixture. The amount is preferably 1 to 50 times volume and more preferably 1 to 20 times volume.

The crystallization may be carried out with a proper combination of various methods such as commonly employed crystallization by cooling, crystallization by concentration and crystallization by solvent replacement.

The temperature at the time of the crystallization is not also particularly limited; however, the temperature is preferably in a range of −25 to 80° C., more preferably −10 to 80° C., and even more preferably 0 to 50° C.

The time to carry out the crystallization is not particularly limited; however, the time is preferably 0.1 to 50 hours and more preferably 0.1 to 24 hours.

A crystal of the optically active imidazolidinone derivative containing any one of the optical isomers in an excess amount can be obtained by the preferential crystallization. The optical purity of the obtained derivative is generally in a range of 80 to 100% de. The optical purity is preferably 85% de or higher and particularly preferably 90% de or higher. In addition, it is possible to further improve the optical purity of the optically active imidazolidinone derivative by means of repeated crystallization of the present invention.

Furthermore, in the preferential crystallization process, it is also possible to crystallize one of the optically active imidazolidinone derivatives while the imidazolidinone derivative is isomerized. Such a method of obtaining the optically enriched compound with isomerization is known as the dynamic kinetic resolution (Reference Document: Chemical Review, 2006, vol. 106, p. 2711). Obviously, it has not been exemplified so far that dynamic kinetic resolution can be applied for an imidazolidinone derivative represented by the above general formula (1).

The isomerization method of the imidazolidinone derivative is not particularly limited; however, for example, methods such as use of an acidic catalyst, use of a basic catalyst, use of an optically active acid or base, warming conditions, heating conditions and light irradiation can be exemplified. Among the methods, use of an acidic catalyst is preferable with respect to dynamic kinetic resolution of the imidazolidinone derivative.

The acidic catalyst is not particularly limited as long as the catalyst can promote the isomerization with respect to the 2-position carbon atom of the imidazolidinone ring (the carbon atom opsitioned between the two nitrogen atoms); however, the example includes, for example, mineral acids such as hydrochloric acid, hydrobromic acid, hydroiodic acid, sulfuric acid and nitric acid; sulfonic acids such as methanesulfonic acid, p-toluenesulfonic acid, camphorsulfonic acid and trifluoromethanesulfonic acid; halogeno fatty acids such as trichloroacetic acid and trifluoroacetic acid; and the like. Among the examples, sulfonic acids and halogenoacetic acids are preferable to be used, and p-toluenesulfonic acid or trifluoroacetic acid is more preferable.

The amount of the acidic catalyst is not particularly limited; however, the amount to be used is preferably between 0.001 and 1.0 molar equivalent, more preferably in a range of 0.001 to 0.5 molar equivalents, and even more preferably in a range of 0.001 to 0.4 molar equivalents, based on the molar equivalent of the imidazolidinone derivative to be used.

An organic solvent is also used in the dynamic kinetic resolution, and the example of the solvent includes the solvents as described above as they are. The solvent may be singly used, or two or more kinds of the solvents may be used in combination. The solvent is preferably nitriles, acetic acid esters and aliphatic hydrocarbons, and more preferably acetonitrile, ethyl acetate and hexane.

The amount of the solvent to be used is not also particularly limited; however, the amount is generally preferably in a range of 1 to 100 times volume based on the weight of the imidazolidinone derivative isomeric mixture. The amount is more preferably 1 to 50 times volume and even more preferably 1 to 20 times volume.

The reaction mixture may also be used directly for the dynamic kinetic resolution, since the imidazolidinone derivative isomeric mixture to be used for the dynamic kinetic resolution can be obtained in the presence of a acidic catalyst as described above.

Further, various methods such as commonly employed crystallization by cooling, crystallization by concentration and crystallization by solvent replacement may also be appropriately combined in the dynamic kinetic resolution.

The temperature at the time of the dynamic kinetic resolution is not also particularly limited; however, the temperature is generally preferably in a range of −25 to 120° C., more preferably −10 to 100° C., and even more preferably in a range of 0 to 100° C.

The time of crystallization is not particularly limited; however, the time is preferably 0.1 to 200 hours and more preferably 1 to 100 hours.

It is possible by the above dynamic kinetic resolution to improve the isolated yield of one isomer moreover as compared with common preferential crystallization. The optical purity of the obtained derivative is generally in a range of 80 to 100% de. The optical purity is preferably 85% de or higher and particularly preferably 90% de or higher. Further, it is also possible to improve the optical purity of the optically active imidazolidinone derivative obtained by the dynamic kinetic resolution by repeated crystallization of the present invention described above.

Next, a method of producing an imidazolidinone derivative represented by the general formula (2) is described.

An imidazolidinone derivative represented by the general formula (2) can be produced by reacting an imidazolidinone derivative or an optically active form thereof, represented by the general formula (1) with a halogenoformic acid ester represented by the general formula (6):

$$R^3OCOX \quad (6)$$

or a pyrocarbonic acid ester represented by the general formula (7):

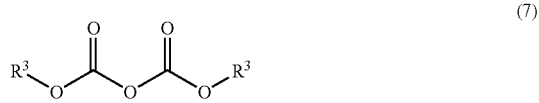

in the presence of a base.

A compound represented by the above formula (1) used for the step may also be treated to remarkably increase content of one optical isomer by the above preferential crystallization or dynamic kinetic resolution, or may not also be subjected to the improvement of the optical purity. In other words, the configuration of (*1, *2) may preferentially be any one of (R, R), (R,S), (S, R) and (S, S), or two or more diastereomers may be contained.

In the general formula (6), $R^3$ is the same as described above, and X represents a halogen atom. The example of X includes a fluorine atom, a chlorine atom, a bromine atom and an iodine atom. X is preferably a chlorine atom. Further, $R^3$ in the general formula (7) can also be exemplified by the same substituent group as descried above.

The example of the compound to be used and represented by the general formulae (6) and (7) includes di-t-butyl dicarbonate, methyl chloroformate, ethyl chloroformate, isopropyl chloroformate, benzyloxycarbonyl chloride, 2,2,2-trichloroethyloxycarbonyl chloride, allyloxycarbonyl chloride and the like; and di-t-butyl dicarbonate, benzyloxycarbonyl chloride and allyloxycarbonyl chloride are preferable.

The molar equivalent of a halogenoformic acid ester of the general formula (6) or a pyrocarbonic acid ester of the general formula (7) to be used is generally preferably 0.1 to 10 molar equivalents and more preferably 0.5 to 5 molar equivalents, based on the molar equivalent of an imidazolidinone derivative represented by the general formula (1).

The reaction is carried out in the presence of a base. The base may be an organic base or an inorganic base, and preferably an organic base. The inorganic base to be used is not particularly limited as long as the base is commonly used by a person skilled in the art, and one or combined two or more kinds of the inorganic bases may be used. The organic base to be used is not particularly limited; however, the example includes aliphatic amines such as triethylamine, diisopropylethylamine and tri-n-butylamine; condensed ring amines such as [2.2.2]diazabicyclooctane, diazabicyclo[5.4.0]undecene and 1,5-diazabicyclo[4.3.0]nonene; pyridines such as pyridine, 2,6-lutidine and 2,4,6-colidine; alkylated aminopyridines such as 4-(N,N-dimethylamino)pyridine and 4-pyridinopyridine; and the like.

The organic bases may be singly used, or two or more kinds of the organic bases may be used in combination. Among the examples, aliphatic amines, alkylated aminopyridines or combinations of the aliphatic amines and alkylaminopyridines are preferable, and triethylamine as the aliphatic amines and 4-(N,N-dimethylamino)pyridine as the alkylaminopyridines are preferable.

The total molar equivalent of the base to be used in the case is generally in a range of 0.1 to 10.0 molar equivalents, preferably in a range of 0.1 to 5.0 molar equivalents, more preferably in a range of 0.5 to 5.0 molar equivalents, even more preferably in a range of 0.5 to 2.5 molar equivalents, and most preferably in a range of 1.0 to 1.5 molar equivalents, based on the molar equivalent of an imidazolidinone derivative represented by the general formula (1). Particularly, when aliphatic amines and alkylated aminopyridines are used in combination as the base, the amount of the alkylated aminopyridines is generally in a range of 0.001 to 5.0 molar equivalents, preferably in a range of 0.001 to 2.5 molar equivalents, and more preferably in a range of 0.001 to 1.0 molar equivalent, based on the molar equivalent of an imidazolidinone derivative represented by the general formula (1).

Generally, a solvent is used for the reaction. The solvent to be used is not particularly limited; however, the example includes aliphatic hydrocarbons such as n-hexane, n-heptane, n-octane, n-nonane, cyclohexane and methylcyclohexane; aromatic hydrocarbons such as benzene, toluene, xylene, chlorobenzene and o-dichlorobenzene; acetic acid esters such as methyl acetate, ethyl acetate, n-butyl acetate, t-butyl acetate and isopropyl acetate; ethers such as tetrahydrofuran, 1,4-dioxane, diisopropyl ether, t-butyl methyl ether and cyclopentyl methyl ether; nitriles such as acetonitrile and propionitrile; and amides such as N,N-dimethylformamide, N,N-dimethylacetamide and 1-methyl-2-pyrrolidone; and the like. The solvent may be singly used, or two or more kinds of the solvents may be arbitrarily combined for use. Among the example, acetonitrile, toluene and ethyl acetate are preferable.

The amount of the solvent to be used is not particularly limited; however, the amount is generally in a range of 1.5 to 50 times volume based on the weight of the imidazolidinone derivative. The amount is particularly preferably 1.5 to 25 times volume.

A reaction temperature is not particularly limited; however, the temperature is preferably −50 to 100° C. and more preferably in a range of −10 to 100° C. and most preferably in a range of −10 to 50° C.

A reaction time is not particularly limited; however, the time is preferably 0.1 to 50 hours and more preferably 0.1 to 25 hours.

An imidazolidinone derivative represented by the general formula (2) and obtained by the above method may be used for the next step directly, or any one of the optically active forms may be preferentially crystallized by the following procedure.

For the crystallization of an imidazolidinone derivative represented by the general formula (2), an organic solvent is generally used. The solvent to be used is not particularly limited as long as the solubility of the each isomer in the solvent is sufficiently different among a plurality of optical isomers, since the solubility difference of the optical isomers is utilized in the crystallization. The example includes aliphatic hydrocarbons such as n-hexane, n-heptane, n-octane, n-nonane, cyclohexane and methylcyclohexane; aromatic hydrocarbons such as benzene, toluene, xylene, chlorobenzene and o-dichlorobenzene; acetic acid esters such as methyl acetate, ethyl acetate, n-butyl acetate, t-butyl acetate and isopropyl acetate; ethers such as tetrahydrofuran, 1,4-dioxane, diisopropyl ether, t-butyl methyl ether and cyclopentyl methyl ether; nitrites such as acetonitrile and propionitrile; amides such as N,N-dimethylformamide, N,N-dimethylacetamide and 1-methyl-2-pyrrolidone; and the like. The solvent may be singly used, or two or more kinds of the solvents may be arbitrarily combined for use. Among the example, hydrocarbons and esters are preferable to be used in combination, and combination of ethyl acetate and hexane or hexane alone is more preferable to be used.

The amount of the solvent to be used is not particularly limited; however, the amount is generally in a range of 1 to 100 times volume based on the weight of the imidazolidinone derivative isomeric mixture. The amount is preferably 1 to 50 times volume, and more preferably 1 to 20 times volume.

When two or more kinds of the solvents are used, the ratio of the solvents to be used is not particularly limited; however, hexane may be used at a ratio in a range of 0 to 100 times volume based on the volume of ethyl acetate.

The crystallization can be carried out by properly combining various methods such as commonly employed crystallization by cooling, crystallization by concentration and crystallization by solvent replacement.

A crystallization temperature is not also particularly limited; however, the temperature is generally in a range of −30 to 80° C., preferably −20 to 80° C., and more preferably in a range of −15 to 50° C.

A time to carry out the crystallization is not particularly limited; however, the time is preferably 0.1 to 80 hours and more preferably 0.1 to 65 hours.

A crystal of the optically enriched imidazolidinone derivative containing any one of optical isomers in an excess amount can be obtained by the preferential crystallization. The optical purity of the obtained optically active form is not particularly limited unless the optical purity exerts a bad influence in the successive steps; however, the optical purity is generally in a range of 80 to 100% de, preferably 85% de or higher, and particularly preferably 90% de or higher. The optical purity of the optically active imidazolidinone derivative can be further improved by repeated crystallization of the present invention.

A residual mother liquid after separation of the optically active imidazolidinone derivative containing, for example, S isomer in an excess amount by the preferential crystallization contains a large amount of R isomer. The mother liquid containing a large amount of R isomer is also subjected to the crystallization operation to obtain a crystal containing an excess amount of R isomer. In such a manner, both crystals of S isomer and R isomer can be obtained.

An optically active imidazolidinone derivative represented by the above general formula (3) can be produced by reacting an optically active imidazolidinone derivative represented by the above formula (2) and obtained in the above manner with an electrophilic agent represented by the general formula (8):

R$^7$Y  (8)

in the presence of a base.

A higher optical purity of a compound represented by the above formula (2) to be used in the step is preferable, since the resoluting compound (3) has higher optical purity; however, the optical purity is not particularly limited.

In the general formula (8), R$^7$ represents an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and the specific example includes the same substituent groups as those for R$^4$ and R$^5$.

Y is a leaving group; and the example includes a halogen atom, a sulfonyloxy group and the like. The example of the halogen atom includes fluorine, chlorine, bromine, and iodine; and the example of the sulfonyloxy group includes a methanesulfonyloxy group, a p-toluenesulfonyloxy group, a trifluoromethanesulfonyloxy group, and the like.

The example of an electrophilic agent represented by the general formula (8) to be used includes iodides such as methyl iodide, ethyl iodide, n-propyl iodide, isopropyl iodide, n-butyl iodide, benzyl iodide and allyl iodide; bromides such as methyl bromide, ethyl bromide, n-propyl bromide, n-butyl bromide, 2-bromobutane, 1-bromo-2-methylpropane, 1-bromo-2-butyne, benzyl bromide, allyl bromide, propynyl bromide, p-methoxybenzyl bromide and benzyl 2-bromoethyl ether; chlorides such as benzyl chloride, benzyloxymethyl chloride, 2-chloroethyl methyl sulfide, allyl chloride, 2-chloroethoxytrimethylsilane and benzhydryl chloride; and sulfonates such as allyl methanesulfonate, benzyl methanesulfonate, allyl p-toluene sulfonate, benzyl p-toluene sulfonate and propyl 2-trifluoromethanesulfonate; and the like.

Among the examples, methyl iodide, benzyl bromide, allyl bromide, n-propyl iodide, propynyl bromide, ethyl iodide, benzyloxymethyl chloride, 2-chloroethyl methyl sulfide, 2-chloroethoxytrimethylsilane, 2-bromobutane, 1-bromo-2-methylpropane, 1-bromo-2-butyne and benzhydryl chloride are preferable; and methyl iodide, benzyl bromide, allyl bromide, p-methoxybenzyl bromide, benzyl 2-bromoethyl ether, 2-chloroethoxytrimethylsilane and benzhydryl chloride are more preferable.

The amount of an electrophilic agent represented by the general formula (8) is not particularly limited; however, the amount is generally preferably 0.1 to 5 equivalents and more preferably 0.5 to 2.5 equivalents, based on the molar equivalent of an optically active imidazolidinone derivative represented by the above formula (2). Needless to say, it is preferable to add 1 equivalent or more of a compound represented by the above formula (8) relative to a compound represented by the above formula (2) in order to obtain a compound represented by the above formula (3) with a high yield.

It is preferable to carry out the reaction in inert gas atmosphere. Particularly, the reaction is preferable to be carried out in nitrogen or argon atmosphere.

A base is employed for the reaction. The base to be used is not particularly limited; however, an inorganic base or an organic base is preferable. Among them, an organic base is preferable and an organometallic base is particularly preferable. The example of the organometallic base includes lithium diisopropylamide, lithium dicyclohexylamide, lithium 2,2,6,6-tetramethylpiperazide, lithium hexamethyldisilazide, sodium hexamethyldisilazide, potassium hexamethyldisilazide, t-butyl magnesium chloride, lithium t-butoxide, sodium t-butoxide, potassium t-butoxide, lithium hydride, sodium hydride, potassium hydride, calcium hydride, and the like.

Among the examples, lithium diisopropylamide, lithium hexamethyldisilazide, sodium hexamethyldisilazide, potassium hexamethyldisilazide, t-butyl magnesium chloride, potassium t-butoxide, sodium t-butoxide, lithium t-butoxide, lithium hydride, sodium hydride, potassium hydride and calcium hydroxide are preferable; and lithium amide bases and disilazide bases are more preferable; and lithium diisopropylamide, lithium disilazide, sodium disilazide and potassium disilazide are most preferable.

The amount of the base is not particularly limited; however, the amount is generally in a range of 0.1 to 2.0 molar equivalents based on the molar equivalent of an optically active imidazolidinone derivative represented by the general formula (2). The amount is preferably in a range of 0.5 to 1.5 molar equivalents and more preferably in a range of 0.9 to 1.3 molar equivalents.

In general, a solvent is used for the reaction. The solvent to be used is not particularly limited; however, a solvent which does not react with the above base is generally preferable in order to avoid reaction with the base. The example includes aliphatic hydrocarbons such as n-hexane, n-heptane, n-octane, n-nonane, cyclohexane and methylcyclohexane; aromatic hydrocarbons such as benzene, toluene, xylene, chlorobenzene, o-dichlorobenzene and ethylbenzene; and ethers such as tetrahydrofuran, 1,2-dimethoxyethane, diethyl ether, diisopropyl ether, t-butyl methyl ether and cyclopentyl methyl ether; and the like. Among the example, tetrahydrofuran, toluene, ethylbenzene, 1,2-dimethoxyethane are preferable. The solvent may be singly used, two or more kinds may be used in combination.

The amount of the solvent to be used is not particularly limited; however, the amount is generally in a range of 1.0 to 50 times volume based on the weight of the imidazolidinone derivative. The amount is preferably 2.5 to 25 times volume.

A reaction temperature is not particularly; however, the reaction is generally carried out, for example, at 30° C. or lower. The temperature is preferably in a range of −100 to 20° C., more preferably in a range of −50 to 20° C., even more preferably in a range of −40 to 20° C., and particularly preferably in a range of −30 to 20° C.

A reaction time is not particularly limited; however, the time is preferably 0.1 to 48 hours and more preferably 0.1 to 24 hours.

The two substituent groups in 4-position of the imidazolidinone ring of an optically active imidazolidinone derivative represented by the above general formula (2) are both hydrogen atoms. It is possible by the above reaction to introduce different two substituent groups successively by one-pot reaction, or to introduce only one substituent group, or to introduce only one substituent group to isolate the product once and then to introduce the second substituent group in steps.

Specifically, when only one kind of an electrophilic agent represented by the above formula (8) is used, a compound represented by the above formula (3) in which one of $R^4$ and $R^5$ is a hydrogen atom and the other is the above $R^7$, i.e. a compound represented by the general formula (11):

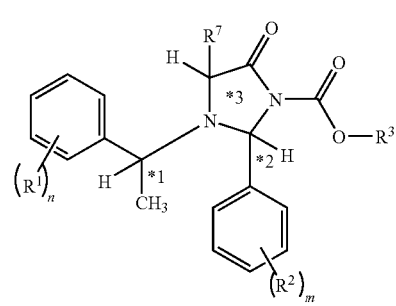

(11)

wherein, n, m, $R^1$, $R^2$, $R^3$, $R^7$, *1, *2 and *3 are the same as described, can be produced.

To the contrary, when different kinds of electrophilic agents, that is, the electrophilic agent (8) and an electrophilic agent (8)':

$$R^{7'}Y \qquad (8)'$$

wherein, $R^{7'}$ is different from $R^7$ and represents an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and Y represents a leaving group,
are used, the different substituent groups $R^4$ and $R^5$ can simultaneously be introduced. In the case, one of $R^4$ and $R^5$ is $R^7$ and the other is $R^{7'}$.

The addition order of a base, a compound represented by the above formula (2), a compound (electrophilic agent) represented by the above formula (8) (general formula (8)') (hereinafter, the general formula (8) includes the general formula (8)') and a reaction solvent is not particularly limited. When two or more kinds of compounds represented by the above formula (8) are used for carrying out the reaction, the addition order of a base, a compound represented by the above formula (2), two kinds of compounds represented by the above formula (8) and a reaction solvent is not particularly limited. It is preferable to react one kind of compound represented by the above formula (8) in a reaction solvent with a compound represented by the above formula (2) in the presence of a base, and thereafter to add a base, and to add the other compound represented by the above formula (8). In such a case, a compound represented by the above formula (11) and obtained by reacting one kind of compound represented by the above formula (8) and a compound represented by the above formula (2) may be isolated once or may not be isolated. Further, one-pot reaction may be carried out without forming a compound represented by the above formula (11) or without confirming the production of a compound represented by the above formula (11).

When one kind of compound represented by the general formula (8) is used as an electrophilic agent, one of $R^4$ and $R^5$ becomes the same as $R^7$ in the compound represented by the general formula (3). When two kinds of compounds represented by the general formula (8) are used, one of $R^4$ and $R^5$ becomes $R^7$ and the other becomes $R^{7'}$.

The amount of a compound represented by the above formula (8) for producing a compound of the general formula (11) is not particularly limited; however, the amount is generally preferably 0.1 to 5 equivalents and more preferably 0.5 to 2.5 equivalents, based on the molar equivalent of a compound represented by the above formula (2). Needless to say, it is preferable to add 1 equivalent or more of a compound represented by the above formula (8) relative to a compound represented by the above formula (2) in order to obtain a compound represented by the above formula (11) with a high yield. When two or more kinds of compounds represented by the above formula (8) are used to introduce different substituent groups by one-pot, the respective compound represented by the above formula (8) may be added in the above equivalent amounts.

Further, it is also possible to produce an optically active imidazolidinone derivative represented by the above formula (3) in which both of $R^4$ and $R^5$ are not hydrogen atom by reacting a compound represented by the above formula (11) and obtained by the above method with an electrophilic agent represented by the above formula (8) in the presence of a base. A detailed reaction condition of the production method is the same as that of the method of carrying out the reaction using one kind of compound represented by the above formula (8) in the production method of a compound of the general formula (3) from a compound of the general formula (2).

An optically active N-(1-substituted phenylethyl)amino acid derivative represented by the general formula (9):

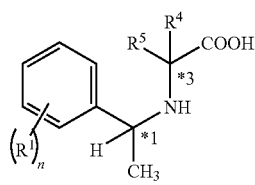

(9)

wherein, n, $R^1$, $R^4$, $R^5$, *1 and *3 are the same as described above, can be produced by treating an optically active imidazolidinone derivative having a substituent group in 4-position of the imidazolidinone ring produced in the above manner and represented by the above formula (3) with an acid or a base in at least one of an organic solvent and water. In the optically active imidazolidinone derivative, one of $R^4$ and $R^5$ may be a hydrogen atom or both may be groups other than hydrogen atom. In the process, the following three transformations are promoted. The order is not particularly concerned. The three reactions are as follows:

i) elimination reaction of the $R^3$-substituted carbonyloxy group on nitrogen atom at 1-position of the imidazolidinone ring;
ii) ring opening reaction by hydrolysis of the N,N-crosslinking substituent group in the imidazolidinone ring; and
iii) hydrolysis reaction of a carboxylic acid amide to a carboxylic acid.

An organic solvent and/or water is used for the reaction. The kind of the organic solvent to be used is not particularly limited, and the example includes aliphatic hydrocarbons such as n-hexane, n-heptane, n-octane, n-nonane, cyclohexane and methylcyclohexane; aromatic hydrocarbons such as benzene, toluene, xylene, chlorobenzene and o-dichlorobenzene; acetic acid esters such as methyl acetate, ethyl acetate, n-butyl acetate, t-butyl acetate and isopropyl acetate; ethers such as diisopropyl ether, t-butyl methyl ether, cyclopentyl methyl ether, tetrahydrofuran and 1,4-dioxane; nitriles such as acetonitrile and propionitrile; alcohols such as methanol, ethanol, n-propanol, isopropanol, n-butanol, isobutanol and 2-methyl-2-propanol; amides such as N,N-dimethylformamide, N,N-dimethylacetamide and 1-methyl-2-pyrrolidone; and the like.

The organic solvent and water may be singly used. Alternatively, two or more kinds of the organic solvents may be used in combination at an arbitrary ratio. Further, the organic solvent and water may be used in combination; and the solvent may be mixed with water at an arbitrary ratio in the case. Non-mixable solvent mixture consisting of solvents which cannot be mixed from each other may be used. Among the example, use of water, alcohols and ethers are preferable, and water, methanol, ethanol, isopropanol and tetrahydrofuran are more preferable.

The amount of the organic solvent and/or water to be used is not particularly limited; however, the amount is generally in a range of 1 to 100 times volume based on the weight of an optically active imidazolidinone derivative represented by the general formula (3). The amount is preferably 1 to 80 times volume, more preferably 1 to 50 times volume, and most preferably 1 to 30 times volume.

An acid or a base is added to the solution of an optically active imidazolidinone derivative produced in the above manner and represented by the general formula (3) to carry out the reaction.

The acid or base to be used is not particularly limited; however, the example of the acid includes mineral acids such as hydrochloric acid, hydrobromic acid, hydroiodic acid, sulfuric acid, nitric acid and fuming nitric acid; sulfonic acids such as methanesulfonic acid, benzenesulfonic acid, toluenesulfonic acid and trifluoromethanesulfonic acid; halogeno fatty acids such as trifluoroacetic acid and trichloroacetic acid; and the like.

The example of the base includes metal hydroxides such as lithium hydroxide, sodium hydroxide, potassium hydroxide, calcium hydroxide, cesium hydroxide, barium hydroxide and magnesium hydroxide; metal alkoxides such as lithium methoxide, sodium methoxide, potassium methoxide, calcium methoxide, lithium ethoxide, sodium ethoxide, potassium ethoxide, calcium ethoxide, lithium t-butoxide, sodium t-butoxide and potassium t-butoxide; and the like.

In the case of using the acid, mineral acids are preferable. Among the examples, hydrochloric acid and sulfuric acid are preferable. In the case of using the base, metal hydroxides are preferable. Among the example, lithium hydroxide, sodium hydroxide, potassium hydroxide and calcium hydroxide are preferable.

The use amount of the acid or base is not also particularly limited; however, the amount is generally in a range of 1 to 100 molar equivalents, preferably in a range of 1 to 80 molar equivalents, more preferably in a range of 1 to 50 molar equivalents, and most preferably in a range of 1 to 40 molar equivalents, based on molar equivalent of the optically active imidazolidinone derivative to be used.

At the time of carrying out the reaction by reacting the acid or base in the above manner, a temperature is not particularly limited. In the case of carrying out the reaction in the acidic condition, the temperature is generally in a range of 0 to 180° C., preferably in a range of 0 to 150° C., and more preferably in a range of 0 to 130° C. In the case of carrying out the reaction in the basic condition, the temperature is generally in a range of −10 to 50° C., preferably in a range of −10 to 30° C.

A time of the reaction is not particularly limited; however the time is preferably 0.1 to 72 hours and more preferably 0.1 to 60 hours.

An optically active 2-(1-substituted phenylethyl)amino acid derivative represented by the general formula (9) can be synthesized in the above manner. The reaction solution of the amino acid derivative generally shows acidity or basicity. It is possible to directly obtain a salt of the amino acid derivative by crystallization from the reaction mixture. It is also possible to obtain the optically active 2-(1-substituted phenylethyl) amino acid derivative by addition of a proper base or acid to almost neutralize, causing crystallization.

An optically active amino acid represented by the general formula (10):

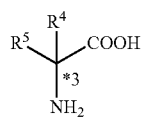

(10)

wherein, $R^4$, $R^5$ and *3 are the same as described above, can be produced by removing a 1-(substituted phenyl)ethyl group as the substituent group on the amino group of an optically active 2-(1-substituted phenylethyl)amino acid derivative represented by the general formula (9) under a normal condition for removing a 1-(substituted phenyl)ethyl group for deprotection, such as an acid, an oxidizing agent or a hydrogenolysis.

The optically active amino acid derivative synthesized in the above manner can be obtained not only by various methods employed commonly for isolating an amino acid, such as ion exchange column, neutralization-induced crystallization, salt forming crystallization, and the like but also by conversion into an N-substituted amino acid, i.e. N-carbamoylation or N-acylation, directly from the reaction mixture. The obtained N-substituted amino acid can also be isolated by procedure such as extraction, crystallization or the like.

An optically active amino acid represented by the general formula (10) can be produced by removing the 1-(substituted phenyl)ethyl group as the protective substituent group on the nitrogen of an optically active imidazolidinone derivative represented by the general formula (3) and an N,N-crosslinking substituent group composing the imidazolidinone ring to synthesize an optically active amino acid amide represented by the general formula (12):

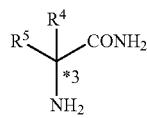

(12)

wherein, $R^4$, $R^5$ and *3 are the same as described above, thereafter treating the amino acid amide with an acid or a base in a solvent containing at least one kind of organic solvents and water.

The 1-(substituted phenyl)ethyl group and the N,N-crosslinking substituent group composing the imidazolidinone ring can be removed by catalytic hydrogenolysis in one step. Further, it is naturally possible to open the ring by hydrolysis with respect to the N,N-crosslinking substituent group of the imidazolidinone ring. The 1-(substituted phenyl)ethyl group can be removed in one step by catalytic hydrogenolysis while the ring opening reaction is carried out.

As an illustrative example of the above procedure, an imidazolidinone derivative represented by the above formula (3) is dissolved in at least one of organic solvents and water, and then a catalyst for hydrogenolysis is added, and the mixture is allowed to react the derivative with a hydrogen gas to give an optically active amino acid amide represented by the above formula (12).

A catalyst for hydrogenolysis to be used in the case is not particularly limited as long as the catalyst is commonly used; however, the example includes palladium catalysts such as palladium carbon, palladium hydroxide carbon, palladium oxide and palladium black; and platinum catalysts such as platinum oxide and platinum black. Among the example, a palladium catalyst is preferable, and palladium-carbon and palladium hydroxide-carbon are more preferable.

The amount of the catalyst is not also particularly limited; however, the amount is generally preferably in a range of 0.01 to 5.0 times by weight and more preferably in a range of 0.05 to 1.5 times by weight, based on the weight of the imidazolidinone derivative as a substrate.

Hydrogen gas is used for the reaction. The use volume and pressure thereof are not particularly limited unless the conditions exert a bad influence on the reaction; however, the pressure is generally preferably in a range of 0.01 MPa to 100 MPa and more preferably in a range of 0.1 to 50 MPa.

An organic solvent and/or water may generally used in the reaction. The kind and the amount of the organic solvent to be used can be exemplified by the same as the examples for the organic solvent to be used in the above conversion from the general formula (3) to the general formula (9), and the combination of the solvents and combination use with water are also the same as those described above.

As the organic solvent, hexane, heptane, toluene, methyl acetate, ethyl acetate, isopropyl acetate, butyl acetate, methanol, ethanol, isopropanol, n-butanol, isobutanol, 2-butanol, 2-methyl-2-propanol, diethyl ether, diisopropyl ether, tetrahydrofuran, t-butyl methyl ether, cyclopentyl methyl ether and the like are preferable, and tetrahydrofuran is more preferable.

The reaction may also be carried out in the presence of an acid. The kind of the acid to be added is not also particularly limited; however, the example includes mineral acids such as hydrochloric acid, hydrobromic acid, hydroiodic acid, sulfuric acid, nitric acid and fuming nitric acid; sulfonic acids such as methanesulfonic acid, benzenesulfonic acid, toluenesulfonic acid and trifluoromethanesulfonic acid; halogeno fatty acids such as trifluoroacetic acid and trichloroacetic acid; formic acid; acetic acid; propionic acid; and the like; and among the examples, hydrochloric acid, sulfuric acid, formic acid and acetic acid are preferable.

An optically active amino acid represented by the general formula (10) can be produced by removing the 1-(substituted phenyl)ethyl group and the N,N-crosslinking substituent group composing the imidazolidinone ring in the above manner to produce an optically active amino acid amide and thereafter carrying out the operation of the above step iii), that is, hydrogenolysis of a carboxylic acid amide to a carboxylic acid. The kind and the use amount of the acid or base to be used in the case can be exemplified by the same as those to be used for conversion to an optically active N-1-(phenylethyl-substituted)amino acid represented by the general formula (9) from an imidazolidinone derivative represented by the general formula (3).

Next, a method of producing an optically active imidazolidinone derivative having a hydroxy group is described. The imidazolidinone derivative is represented by the general formula (14):

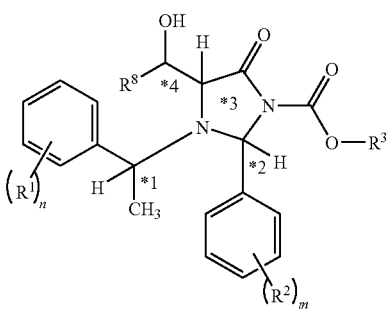

(14)

wherein, n, m, $R^1$, $R^2$, $R^3$, $R^8$, *1, *2 and *3 are the same as described above; and in case that $R^8$ is not a hydrogen atom, *4 indicates an asymmetric carbon atom.

In the method, an optically active imidazolidinone derivative represented by the general formula (2) is reacted with an aldehyde represented by the general formula (13):

wherein, $R^8$ represents a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms, in the presence of a base.

A higher optical purity of a compound represented by the above formula (2) to be used in the step is more preferable, since the resulting compound (14) has higher optical purity with respect to the asymmetric carbon *3; however, the optical purity is not particularly limited.

A compound represented by the general formula (13) is an aldehyde, and $R^8$ in the general formula (13) represents a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms. When $R^8$ is a hydrogen atom, *4 is not an asymmetric carbon atom.

The example of the alkyl group includes a methyl group, an ethyl group, an n-propyl group, an isopropyl group, an n-butyl group, an isobutyl group, a 1-methylpropyl group, a 2-methylpropyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and the like, and the group may have a substituent group at any arbitrary site.

The kind of the substituent group may includes a halogen atom, an alkoxy group, a hydroxyl group, an aralkyloxy group, an alkylthio group, an alkylsilyloxy group, an arylalkylsilyloxy group, and the like. The Example includes a 3-chloropropyl group, a 2-methoxyethyl group, a benzyloxymethyl group, a 2-benzyloxyethyl group, a 2-(mercaptomethyl)ethyl group, a 2-(t-butyldimethylsilyloxy)ethyl group, a 2-(t-butyldiphenylsilyloxy)ethyl group, a 2-trimethylsilyloxyethyl group, and the like.

The example of the optionally substituted alkenyl group having 2 to 18 carbon atoms includes an ally group, a vinyl group, a 3-butenyl group, a 2-methyl-2-propenyl group, a 3-phenyl-2-propenyl group, and the like. The example of the optionally substituted alkynyl group having 2 to 18 carbon atoms includes a propynyl group, a 2-butynyl group, a 3-butynyl group, a 2-pentynyl group, and the like.

The example of the optionally substituted aralkyl group having 7 to 18 carbon atoms includes a benzyl group, a p-methoxyphenylmethyl group, a p-nitrophenylmethyl group, a p-bromophenylmethyl group, a p-chlorophenylmethyl group, a 2,4-dichlorophenylmethyl group, a naphthylmethyl group, a 1-indanoyl group, and the like.

The example of the optionally substituted aryl group having 6 to 18 carbon atoms includes a phenyl group, a p-methoxyphenyl group, a naphthyl group, and the like.

In the production for the optically active hydroxyamino acid, the example of $R^8$ is preferably a hydrogen atom, a methyl group, an ethyl group, a benzyl group, a 2-phenylethyl group, a propyl group, an allyl group, a propynyl group, a 1-methylpropyl group, a 2-methylpropyl group, a benzyloxymethyl group, a 2-(mercaptomethyl)ethyl group, a p-methoxyphenylmethyl group and a 2-trimethylsilyloxyethyl group.

The specific example of an electrophilic agent represented by the general formula (13) to be used includes formaldehyde, acetaldehyde, propionaldehyde, phenylacetaldehyde, 3-phenylpropionaldehyde, butylaldehyde, acrolein, 3-butenylaldehyde, 3-butynylaldehyde, 2-methylbutylaldehyde, 3-methylbutylaldehyde, benzyloxyacetaldehyde, 2-(mercaptomethyl)-propionaldehyde, p-methoxyphenylacetaldehyde, 2-trimethylsilylpropionaldehyde, benzaldehyde, p-methoxybenzaldehyde, and the like.

The amount of an electrophilic agent represented by the general formula (13) is not particularly limited; however, the amount is generally preferably 0.1 to 5 equivalents and more preferably 0.5 to 2.5 equivalents, relative to a compound represented by the above formula (14). Needless to say, it is preferable to add 1 equivalent or more of a compound represented by the above formula (13) relative to a compound represented by the above formula (2) in order to obtain a compound represented by the above formula (14) with a high yield.

The reaction is preferably carried out under inert gas atmosphere. Particularly, the reaction is preferably carried out in nitrogen or argon atmosphere.

A base is employed for the reaction. The base to be used is not particularly limited; however, an inorganic base or an organic base is preferable. Among them, an organic base is preferable, and an organometallic base is most preferable.

The example of an organometal base includes lithium diisopropylamide, lithium dicyclohexylamide, lithium 2,2,6,6-tetramethylpiperazide, lithium hexamethyldisilazide, sodium hexamethyldisilazide, potassium hexamethyldisilazide, t-butyl magnesium chloride, lithium t-butoxide, sodium t-butoxide, potassium t-butoxide, lithium hydride, sodium hydride, potassium hydride, calcium hydride, and the like.

Among the examples, lithium diisopropylamide, lithium hexamethyldisilazide, sodium hexamethyldisilazide, potassium hexamethyldisilazide, t-butyl magnesium chloride, potassium t-butoxide, sodium t-butoxide, lithium t-butoxide, lithium hydride, sodium hydride, potassium hydride and calcium hydroxide are preferable; and lithium amide type bases and disilazide type bases are more preferable; and lithium diisopropylamide, lithium disilazide, sodium disilazide and potassium disilazide are most preferable.

The amount of the base is not particularly limited; however, the amount is generally in a range of 0.1 to 2.0 molar equivalents based on the molar equivalent of an optically active imidazolidinone derivative represented by the general formula (2). The amount is preferably in a range of 0.5 to 1.5 molar equivalents and more preferably in a range of 0.9 to 1.3 molar equivalents.

In general, a solvent is used for the reaction. The solvent to be used is not particularly limited; however, a solvent which does not react with the above base is preferable in order to avoid reaction with the base. The example includes aliphatic hydrocarbons such as n-hexane, n-heptane, n-octane, n-nonane, cyclohexane and methylcyclohexane; aromatic hydrocarbons such as benzene, toluene, xylene, chlorobenzene, o-dichlorobenzene and ethylbenzene; and ethers such as tetrahydrofuran, 1,2-dimethoxyethane, diethyl ether, diisopropyl ether, t-butyl methyl ether and cyclopentyl methyl ether; and the like. Among the example, tetrahydrofuran, toluene, ethylbenzene, 1,2-dimethoxyethane are preferable. The solvent may be singly used, or two or more kinds of the solvents may be used in combination.

The amount of the solvent to be used is not particularly limited; however, the amount is generally preferably in a range of 1.0 to 50 times volume and more preferably 2.5 to 25 times volume, based on the weight of the imidazolidinone derivative.

A reaction temperature is not particularly limited; however, for example, the reaction is generally carried out at 30° C. or lower. The temperature is preferably in a range of −100 to 0° C., more preferably in a range of −100 to 0° C., particularly preferably in a range of −100 to −30° C. A reaction time is not particularly limited; however, the time is preferably 0.1 to 48 hours and more preferably 0.1 to 24 hours.

When $R^8$ is not a hydrogen atom in the reaction, another asymmetric carbon atom *4 is formed. The optical purity at *4 is not particularly limited; however, the purity is generally preferably 50% de or higher and more preferably 60% de or higher.

Next, a method of producing an optically active N-(1-substituted phenylethyl)hydroxyamino acid derivative is described. The optically active N-(1-substituted phenylethyl) hydroxyamino acid derivative is represented by the general formula (15):

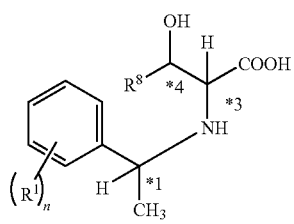

(15)

wherein, n, $R^1$, $R^8$, *1, *3 and *4 are the same as described above.

In the production method, an optically active imidazolidinone derivative represented by the general formula (14) is treated with an acid or a base in at least one of organic solvents and water.

The following three transformations are promoted in the process. The order is not particularly concerned. The three reactions are as follows:

i) elimination reaction of the $R^3$-substituted carbonyloxy group on nitrogen atom at 1-position of the imidazolidinone ring;

ii) ring opening reaction by hydrolysis of the N,N-crosslinking substituent group in the imidazolidinone ring; and iii) hydrolysis reaction of a carboxylic acid amide to a carboxylic acid.

An organic solvent and/or water is used for the reaction. The kind of the organic solvent to be used is not particularly limited; however, the example includes aliphatic hydrocarbons such as n-hexane, n-heptane, n-octane, n-nonane, cyclohexane and methylcyclohexane; aromatic hydrocarbons such as benzene, toluene, xylene, chlorobenzene and o-dichlorobenzene; acetic acid esters such as methyl acetate, ethyl acetate, n-butyl acetate, t-butyl acetate and isopropyl acetate; ethers such as diisopropyl ether, t-butyl methyl ether, cyclopentyl methyl ether, tetrahydrofuran and 1,4-dioxane; nitriles such as acetonitrile and propionitrile; alcohols such as methanol, ethanol, n-propanol, isopropanol, n-butanol, isobutanol and 2-methyl-2-propanol; amides such as N,N-dimethylformamide, N,N-dimethylacetamide and 1-methyl-2-pyrrolidone; and the like. The organic solvent and water may be singly used.

Alternatively, two or more kinds of the organic solvents may be used in combination at an arbitrary ratio. Further, the organic solvent and water may be used in combination; and in the case, the solvent may be mixed with water at an arbitrary ratio. Non-mixable solvent mixture consisting of solvents which cannot intermix each other may be used. Among the examples, use of water, or alcohols and ethers is preferable; and single use of water, and methanol, ethanol, isopropanol and tetrahydrofuran are more preferable.

The amount of the organic solvent and/or water to be used is not particularly limited; however, the amount is generally in a range of 1 to 500 times volume based on the weight of an optically active imidazolidinone derivative represented by the general formula (14). The amount is preferably 1 to 300 times volume and more preferably 1 to 200 times volume.

An acid or a base is added to the solution of an optically active imidazolidinone derivative represented by the general formula (14), produced in the above manner, to carry out the reaction. The acid or base to be used is not particularly limited; however, the example of the acid includes mineral acids such as hydrochloric acid, hydrobromic acid, hydroiodic acid, sulfuric acid, nitric acid and fuming nitric acid; sulfonic acids such as methanesulfonic acid, benzenesulfonic acid, toluenesulfonic acid and trifluoromethanesulfonic acid; and halogeno fatty acids such as trifluoroacetic acid and trichloroacetic acid. The example of the base includes metal hydroxides such as lithium hydroxide, sodium hydroxide, potassium hydroxide, calcium hydroxide, cesium hydroxide, barium hydroxide and magnesium hydroxide; and metal alkoxides such as lithium methoxide, sodium methoxide, potassium methoxide, calcium methoxide, lithium ethoxide, sodium ethoxide, potassium ethoxide, calcium ethoxide, lithium t-butoxide, sodium t-butoxide and potassium t-butoxide.

In the case of using the acid, mineral acids are preferable, and hydrochloric acid and sulfuric acid are particularly preferable. In the case of using the base, metal hydroxides are preferable, and lithium hydroxide, sodium hydroxide, potassium hydroxide and calcium hydroxide are particularly preferable.

The amount of the acid and base is not also particularly limited; however, the amount is generally in a range of 1 to 200 molar equivalents, preferably 1 to 100 molar equivalents, and more preferably in a range of 1 to 60 molar equivalents, based on molar equivalent of the optically active imidazolidinone derivative.

A temperature at the time of carrying out the reaction by the acid or base as the above manner is not particularly limited. In the case of carrying out the reaction under the acidic condition, the temperature is generally in a range of 0 to 180° C., preferably 0 to 150° C., and more preferably in a range of 0 to 130° C. In the case of carrying out the reaction under the basic condition, the temperature is generally in a range of −10 to 50° C., preferably in a range of −10 to 30° C. A time of the reaction is not particularly limited; however, the time is preferably 0.1 to 72 hours and more preferably 0.1 to 60 hours.

An optically active 2-(1-substituted phenylethyl)-3-hydroxyamino acid derivative represented by the general formula (15) can be synthesized in the above manner. The reaction mixture of the hydroxyamino acid derivative generally is acidic or basic. It is possible to directly obtain a salt of the hydroxyamino acid derivative by crystallization from the reaction mixture. It is also possible to obtain the optically active 2-(1-substituted phenylethyl)-3-hydroxyamino acid derivative by addition of a proper base or acid to almost neutralize the mixture and subsequent neutralization-induced crystallization.

Further, an optically active hydroxyamino acid represented by the general formula (16):

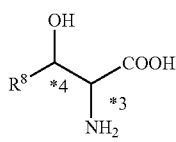

(16)

wherein, $R^8$, *3 and *4 are the same as described above, can be produced by removing the 1-(substituted phenyl)ethyl group as a protective substituent group on the amino group by a general method for removing a 1-(substituted phenyl)ethyl group for deprotection, such as an acid, an oxidizing agent and a catalytic hydrogenolysis. The optically active hydroxyamino acid synthesized in the above manner can be obtained not only by various methods employed generally for isolating an amino acid, such as an ion exchange column, neutralization-induced crystallization, salt forming crystallization, and the like but also by conversion into an N-substituted amino acid by direct N-carbamoylation or N-acylation from the reaction mixture. The obtained N-substituted amino acid can also be isolated by procedure such as extraction, crystallization, or the like.

Furthermore, an optically active amino acid derivative can be produced by removing the 1-(substituted phenyl)ethyl group as the protective substituent group on the nitrogen of an optically active hydroxyimidazolidinone derivative represented by the general formula (14) and the N,N-crosslinking substituent group composing the imidazolidinone ring to obtain an optically active hydroxyamino acid amide represented by the general formula (17):

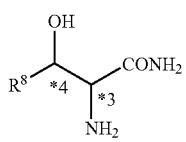

(17)

wherein, $R^8$, *3 and *4 are the same as described above, thereafter treating the hydroxyamino acid amide with an acid or a base in at least one of an organic solvent and water.

The 1-(substituted phenyl)ethyl group and the N,N-crosslinking substituent group composing the imidazolidinone ring can be removed in one step by catalytic hydrogenolysis. With respect to the N,N-crosslinking substituent group of the imidazolidinone ring, the ring can be naturally opened by hydrolysis. The 1-(substituted phenyl)ethyl group can be also removed in one step while the ring opening reaction is carried out.

For example, a method of dissolving an hydroxyimidazolidinone derivative represented by the general formula (14) in at least one of an organic solvent and/or water and thereafter adding a catalyst for hydrogen addition and further reacting with hydrogen gas is exemplified as the procedure. By the method, an optically active amino acid amide represented by the above general formula (17) can be synthesized.

The catalyst for hydrogen addition to be used in the case is not particularly limited as long as the catalyst is generally used; however, the example includes palladium catalysts such as palladium-carbon, palladium hydroxide-carbon, palladium oxide and palladium black; and platinum catalysts such as platinum oxide and platinum black, and a palladium catalyst is preferable, and palladium-carbon and palladium hydroxide-carbon are more preferable.

The amount of the catalyst is not also particularly limited; however, the amount is generally preferably in a range of 0.01 to 5.0 times by weight and more preferably in a range of 0.05 to 1.5 times by weight, based on the weight of the imidazolidinone derivative as a substrate.

Hydrogen gas is used for the reaction, and volume and pressure thereof are not particularly limited unless the conditions exert a bad influence on the reaction. The pressure is generally in a range of 0.01 MPa to 100 MPa and more preferably in a range of 0.1 to 50 MPa.

An organic solvent and/or water may be used for the reaction. With respect to the kind and amount of the organic solvent to be used, the example for the solvent to be used in the above conversion from the general formula (14) to the general formula (15) can be exemplified as it is, and the combination of the solvents and combination use are also the same as those described above. As the organic solvent, hexane, heptane, toluene, methyl acetate, ethyl acetate, isopropyl acetate, butyl acetate, methanol, ethanol, isopropanol, n-butanol, isobutanol, 2-butanol, 2-methyl-2-propanol, diethyl ether, diisopropyl ether, tetrahydrofuran, t-butyl methyl ether, cyclopentyl methyl ether, and the like are preferable, and tetrahydrofuran is more preferable.

An optically active hydroxyamino acid represented by the general formula (17) can be produced by removing the 1-(substituted phenyl)ethyl group and the N,N-crosslinking substituent group composing the imidazolidinone ring in the above manner to produce an optically active hydroxyamino acid amide and thereafter carrying out the operation of the above step iii), that is, hydrolysis of a carboxylic acid amide to a carboxylic acid. As the example of the kind and the amount of the acid or base to be used in the case, the conditions used for conversion to the optically active N-1-(phenylethyl-substituted)amino acid represented by the general formula (15) from the above imidazolidinone derivative represented by the general formula (14) can also be exemplified.

As the above description of the compounds (1), (2) and (3), n=0 is preferable, and the derivative wherein $R^2$ is a chlorine atom, m=2 and phenyl groups are 2,6- or 3,4-disubstituted is preferable in the synthesis of an optically active 2-(1-substituted phenylethyl)amino acid derivative represented by the general formula (9) or the synthesis of an optically active 3-hydroxy-2-(1-substituted phenylethyl)amino acid derivative represented by the general formula (15) through an imidazolidinone derivative isomeric mixture represented by the general formula (1). Further, the derivative wherein $R^2$ is a methyl group and m=3 and the phenyl groups are 2,4,6-substituted is also preferably used. Furthermore, the imidazolidinone derivative wherein $R^3$ is a t-butyl group, a benzyl group or an allyl group is preferably used.

It is no need to say that an optically active imidazolidinone derivative represented by the general formula (2) can be reacted with a substrate which has reactivity for condensation with an imidazolidinone derivative, though the reaction of an optically active imidazolidinone derivative represented by the general formula (2) with a compound represented by the general formula (8) or a compound represented by the general formula (13) is described in the above. The example includes Michel reaction, Mannich reaction, coupling reaction with arylic compound and Claisen condensation.

EFFECT OF THE INVENTION

The optically active imidazolidinone derivative produced by the present invention can be widely used for synthesizing an optically active amino acid, and thereby an optically active amino acid that is important in a wide range of fields including pharmaceutical field in terms of production can easily be produced.

BEST MODE FOR CARRYING OUT THE INVENTION

The present invention is further described in detail with reference to examples hereinbelow; however, it is not intended that the present invention be limited to the examples.

Example 1

(R)-2-[(1-Phenylethyl)amino]-ethanamide

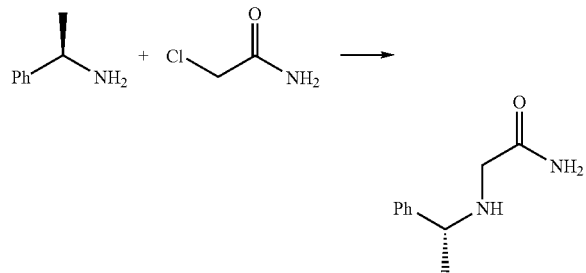

Under nitrogen stream, potassium carbonate (140 g, 1.0 mol) and sodium iodide (15.2 g, 0.1 mol) were added to an anhydrous acetonitrile solution (570 ml) containing chloroacetamide (95 g, 1.0 mol) and (R)-phenylethylamine (123 g, 1.0 mol). The mixture was moderately heated; and after 4 hours, the mixture was refluxed. After the refluxing for 17 hours, the mixture was cooled to room temperature and an insoluble material was separated by filtration. The resulting cake was washed with 200 ml of acetonitrile. After the mother washing solution was concentrated, the residue was dissolved in 1000 ml of ethyl acetate. The solution was washed with water and saturated saline. After the organic layer was concentrated, the residue was again dissolved in 150 ml of ethyl acetate. To the solution, was added dropwise 900 ml of hexane for crystallization to obtain the title compound in an amount of 155 g as a white crystal (yield: 86%).

$^1$H-NMR (400 MHz, CDCl$_3$): δ7.35-7.23 (5H, m), 6.95 (1H, Brs), 5.76 (1H, brs), 3.76 (1H, q, J=6.6 Hz), 3.16 (2H, s), 1.81 (1H, brs), 1.38 (3H, d, J=6.6 Hz)

Example 2

(2,6-Dichlorophenyl)-1-((1'R)-phenylethyl)tetrahydro-1H-4-imidazolone

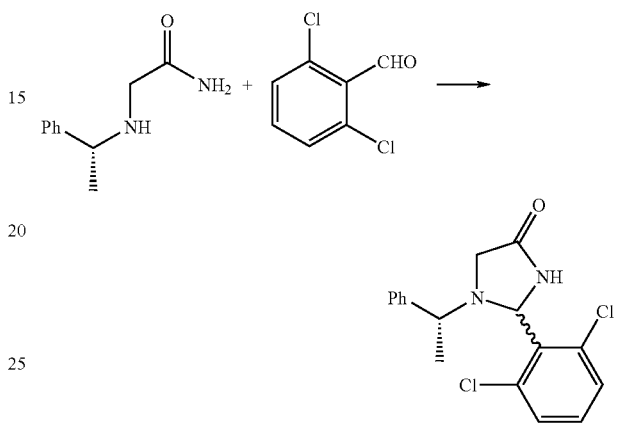

Under nitrogen stream, a toluene solution (500 ml) containing (R)-2-[(1-phenylethyl)amino]-ethanamide (53.5 g, 0.3 mol) obtained by the method in Example 1, 2,6-dichlorobenzaldehyde (50 g, 0.3 mol) and p-toluenesulfonic acid (1.4 g, 7.1 mmol) was refluxed at an outer temperature of 120 to 130° C. for 22 hours. After being cooled to room temperature, the reaction mixture was concentrated to obtain a crude product. After the crude product was dissolved in 160 ml of ethyl acetate, 220 ml of hexane was added dropwise for crystallization to obtain the title compound in an amount of 69.7 g as a white crystal (yield: 72.7%). Further, after the mother solution was concentrated, a similar crystallization operation was carried out twice using 50 ml of ethyl acetate and 50 ml of hexane to obtain the title compound in an amount of 18.5 g as a white crystal (yield: 19.2%). The total amount was 88.2 g (total yield: 91.9%).

$^1$H-NMR (400 MHz, CDCl$_3$): δ7.32-7.18 (8H, m), 6.47 (1H, s), 6.21 (1H, s), 3.87 (1H, q, J=6.6 Hz), 3.49 (1H, dd, J=2.4 Hz, 15.1 Hz), 3.21 (1H, dd, J=1.2 Hz, 15.1 Hz), 1.16 (3H, d, 6.6 Hz)

Example 3

(2R)-(2,6-Dichlorophenyl)-1-((1'R)-phenylethyl) tetrahydro-1H-4-imidazolone

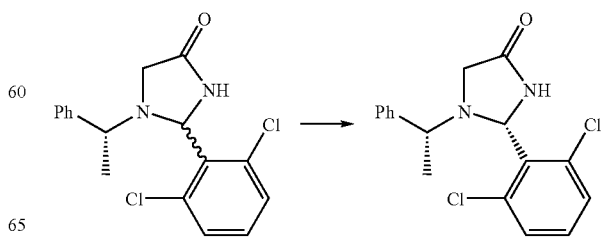

A slurry obtained by adding (2,6-dichlorophenyl)-1-((1'R)-phenylethyl)tetrahydro-1H-4-imidazolone (82.6 g, 0.25 mol) obtained by the method of Example 2 to 140 ml of acetonitrile was filtered to obtain an isomeric mixture of the title compound and 2S isomer as a wet crystal in an amount of 39.5 g (isomer ratio; 2R:2S=73:27). The mixture was successively made to be a slurry and washed with 240 ml of acetonitrile and 70 ml of acetonitrile; and thereafter, dried in vacuum to obtain the title compound in an amount of 16 g (isomer ratio; 2R:2S=99.4:0.6). After the acetonitrile solution as a mother liquid of the slurries was concentrated to obtain a crude material, the crude material was made to be a slurry and washed successively with 573 ml, 286 ml, and 158 ml of acetonitrile; and dried in vacuum to obtain the title compound in an amount of 5.2 g (isomer ratio; 2R:2S=97.9:2.1). The total yield of the compounds was 25.6% (recovered ratio: 51%). The each mother liquid of the produced crystal at the time was mixed together and concentrated to obtain 59.1 g of an isomeric mixture of (2,6-dichlorophenyl)-1-((1'R)-phenylethyl)tetrahydro-1H-4-imidazolone as a brown oily material.

$^1$H-NMR (400 MHz, CDCl$_3$): δ7.32-7.18 (8H, m), 6.47 (1H, s), 6.21 (1H, s), 3.87 (1H, q, J=6.6 Hz), 3.49 (1H, dd, J=2.4 Hz, 15.1 Hz), 3.21 (1H, dd, J=1.2 Hz, 15.1 Hz), 1.16 (3H, d, 6.6 Hz)

Example 4

(2R)-(2,6-Dichlorophenyl)-1-((1'R)-phenylethyl)tetrahydro-1H-4-imidazolone

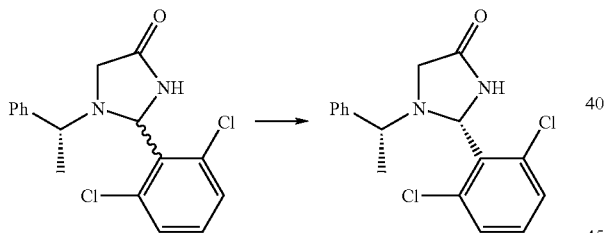

To a suspension of acetonitrile (15 ml) containing (2,6-Dichlorophenyl)-1-((1'R)-phenylethyl)tetrahydro-1H-4-imidazolone (8.8 g, 0.026 mol) obtained in Example 2, were added p-toluenesulfonic acid (100 mg, 0.5 mmol) and distilled water (31 mg, 1.72 mmol). The mixture was heated to 70° C. to obtain a homogenous solution. After the mixture was cooled to 65° C., about 50 mg of the title compound obtained in Example 3 was added as a seed crystal. The mixture was cooled to 60° C. over 1 hour; and then, the mixture was cooled to 50° C. over 3.5 hours. After aging was carried out at 50° C. for 18 hours, the mixture was cooled to 25° C. over 9 hours. Further, after aging was carried out at 25° C. for 15 hours, the precipitated crystal was filtered. The cake was washed with 10 ml of acetonitrile twice and 10 ml of hexane twice to obtain 6.2 g of the title compound as a wet crystal (yield: 70%, 88.4% de). The obtained crystal was washed successively with 10 ml and 5 ml of acetonitrile and further washed with 10 ml of hexane twice; and thereafter, dried in vacuum to obtain 5.0 g of the tile compound (56.1%, yield 99.7% de).

Example 5

(2R)-(2,6-Dichlorophenyl)-1-((1'R)-phenylethyl)tetrahydro-1H-4-imidazolone

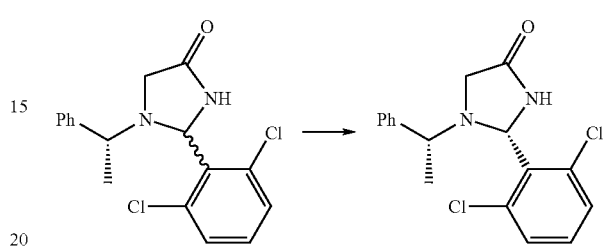

To a suspension of acetonitrile (12.5 ml) containing (2,6-dichlorophenyl)-1-((1'R)-phenylethyl)tetrahydro-1H-4-imidazolone (8.8 g, 0.026 mol) obtained in Example 2, were added p-toluenesulfonic acid (100 mg, 0.5 mmol) and distilled water (31 mg, 1.72 mmol). The mixture was heated to 80° C. to obtain a homogenous solution. After the solution was cooled to 65° C., about 50 mg of the title compound obtained in Example 3 was added as a seed crystal. The mixture was cooled to 60° C. over 45 minutes, and then, was cooled to 50° C. over 2.5 hours. After aging was carried out at 50° C. for 15 hours, the mixture was cooled to 30° C. over 10 hours. Further, after aging was carried out at 30° C. for 13 hours, the precipitated crystal was filtered. The cake was washed with 15 ml of acetonitrile twice and 15 ml of hexane twice to obtain 5.9 g of the title compound (yield: 67%, 99.9% de).

Example 6

(2R)-(2,6-Dichlorophenyl)-1-((1'R)-phenylethyl)tetrahydro-1H-4-imidazolone

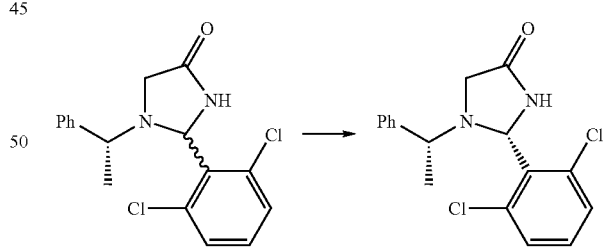

To a suspension of acetonitrile (12.5 ml) containing (2,6-dichlorophenyl)-1-((1'R)-phenylethyl)tetrahydro-1H-4-imidazolone (8.7 g, 0.026 mol) obtained in Example 2, was added trifluoroacetic acid (592 mg, 5.19 mmol). The mixture was heated to 80° C. to obtain a homogenous solution. After the mixture was cooled to 60° C., about 50 mg of the title compound obtained in Example 3 was added as a seed crystal. After the mixture was heated to 65° C. and stirred for 4 hours, the mixture was cooled to 60° C. and aged for 16 hours. After the mixture was further cooled to 5° C. over 6.5 hours, aging was carried out at 5° C. for 4.5 hours. The precipitated crystal was filtered, and the cake was washed with 15 ml of acetonitrile twice and 15 ml of hexane twice. The crystal was dried in vacuum to obtain 5.8 g of the title compound (yield: 67%, 100% de).

Example 7

(2R)-(2,6-Dichlorophenyl)-1-((1'R)-phenylethyl)tetrahydro-1H-4-imidazolone

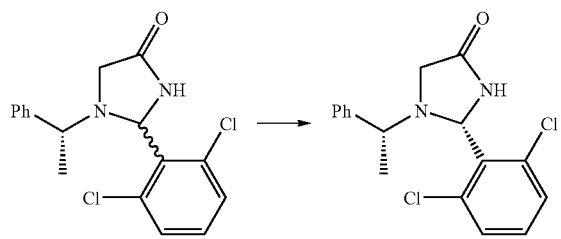

To a suspension of 7.5 ml of ethyl acetate and 7.5 ml of hexane containing (2,6-dichlorophenyl)-1-((1'R)-phenylethyl)tetra-hydro-1H-4-imidazolone (8.8 g, 0.026 mol) obtained in Example 2, was added trifluoroacetic acid (600 mg, 5.26 mmol). The mixture was heated to 80 to 90° C. and refluxed. After 2.5 hours, 2.5 ml of hexane was added dropwise over 15 minutes and the resulting mixture was refluxed for 2 hours. Further, 5 ml of hexane was added dropwise over 15 minutes; and thereafter, the mixture was cooled to 70° C. and aged for 12 hours. The mixture was cooled to 40° C. over 12 hours, and then, aging was carried out at 40° C. for 12 hours. Furthermore, the mixture was cooled to 30° C. and aged for 6 hours. The precipitated crystal was filtered, and the cake was washed with 10 ml and 7.5 ml of ethyl acetate/hexane (2/1 by volume) respectively once and with 10 ml of hexane twice. The crystal was dried in vacuum to obtain 6.7 g of the title compound (yield: 76%, 99.6% de).

Example 8

(2R)-(2,6-Dichlorophenyl)-1-((1'R)-phenylethyl)tetrahydro-1H-4-imidazolone

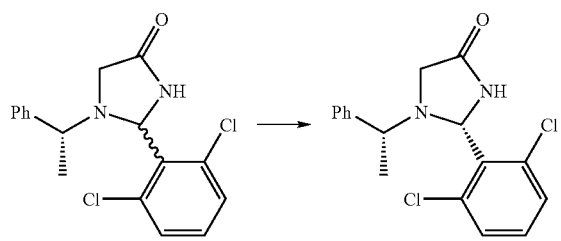

To a suspension of 120 ml of ethyl acetate and 120 ml of hexane containing (2,6-dichlorophenyl)-1-((1'R)-phenylethyl)tetra-hydro-1H-4-imidazolone (137 g, 0.41 mol) obtained in Example 2, was added trifluoroacetic acid (9.3 mg, 0.08 mmol). The mixture was heated to 80 to 90° C. and refluxed. After 1 hour, 120 ml of hexane was added dropwise over 2 hours; and thereafter, the resulting mixture was cooled to 60° C. and aged for 12 hours. The mixture was again heated to 70° C. and aged for 12 hours. The obtained slurry solution was cooled to 28° C. over 54 hours, and the precipitated crystal was filtered. The cake was washed with 160 ml and 120 ml of ethyl acetate/hexane (2/1 by volume) respectively once and with 160 ml of hexane twice. The crystal was dried in vacuum to obtain 115.1 g of the title compound (yield: 84.1%, 98.5% de).

Example 9

1,1-Dimethylethyl-(2R)-(2,6-dichlorophenyl)-5-oxo-3-((1'R)-phenylethyl)tetrahydro-1H-1-imidazolecarboxylate

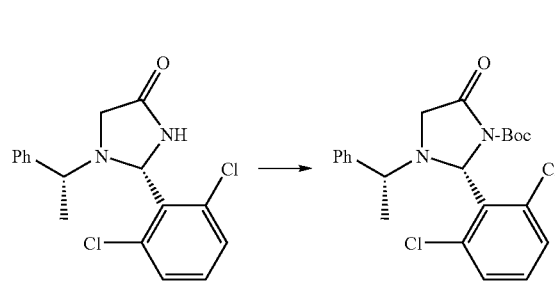

Under nitrogen stream, di-t-butyl dicarbonate (20.5 g, 0.09 mol), triethylamine (9.5 g, 0.09 mol) and 4-(N,N-dimethyl amino)pyridine (0.3 g, 3 mmol) were added at 0° C. to 105 ml of an acetonitrile solution containing (2R)-(2,6-dichlorophenyl)-1-((1'R)-phenylethyl)tetrahydro-1H-4-imidazolone (21 g, 0.06 mol) obtained in Example 8. The mixture was stirred at room temperature for 12 hours. The reaction mixture was concentrated, and then was diluted with ethyl acetate and subjected to treatment by a column tube filled with a small amount of silica gel to remove high polar substance. After the obtained filtrate was concentrated, the residue was dissolved in 15 ml of ethyl acetate. To the solution was added dropwise 150 ml of hexane, and crystallization was carried out to obtain 26.3 g of a wet crystal. The crystal was dried in vacuum at 40° C. for 5 hours to obtain 23 g of the title compound as a white crystal (yield: 84%, 100% de).

$^1$H-NMR (400 MHz, CDCl$_3$): δ7.34-7.17 (8H, m), 6.43 (1H, s), 3.89 (1H, q, J=6.8 Hz), 3.74 (1H, dd, J=2.0 Hz, 16.1 Hz), 3.50 (1H, dd, J=1.0 Hz, 16.1 Hz), 1.29 (3H, d, J=6.8 Hz), 1.26 (9H, s)

Example 10

1,1-Dimethylethyl-(2R)-(2,6-dichlorophenyl)-5-oxo-3-((1'R)-phenylethyl)tetrahydro-1H-1-imidazolecarboxylate

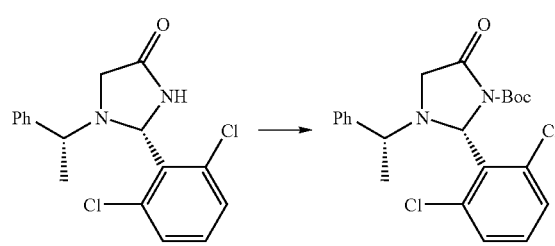

Under nitrogen stream, triethylamine (15.8 g, 0.16 mol) and 4-(N,N-dimethylamino)pyridine (0.45 g, 3.7 mmol) were added at 0° C. to 200 ml of an ethyl acetate solution containing (2R)-(2,6-dichlorophenyl)-1-((1'R)-phenylethyl)tetrahydro-1H-4-imidazolone (50 g, 0.15 mol) obtained in Example 8, and di-t-butyl dicarbonate (37.4 g, 0.17 mol) was furthermore added dropwise. The mixture was stirred at 0° C. for 2 hours. After the reaction mixture was concentrated, the residue was dissolved in 20 ml of ethyl acetate and 400 ml of hexane was added dropwise thereto to carry out crystallization. The crystal was washed with 40 ml of a solution of ethyl acetate/hexane (1/8 by volume) twice and 75 ml of hexane once to obtain a wet crystal. The mother liquid was concentrated to obtain 24 g of a concentrated material; and thereafter, crystallization was carried out using 10 ml of ethyl acetate and 65 ml of hexane. The crystal was washed with 20 ml of a solution of ethyl acetate/hexane (1/8 by volume) twice and 25 ml of hexane once to obtain a wet crystal (secondary crystal). The obtained wet crystals were mixed and dried in vacuum at 40° C. for 24 hours to obtain 58 g of the title compound as a white crystal (yield: 89%, 100% de).

Example 11

1,1-Dimethylethyl-(2S)-(2,6-dichlorophenyl)-5-oxo-3-((1'R)-phenylethyl)tetrahydro-1H-1-imidazolecarboxylate

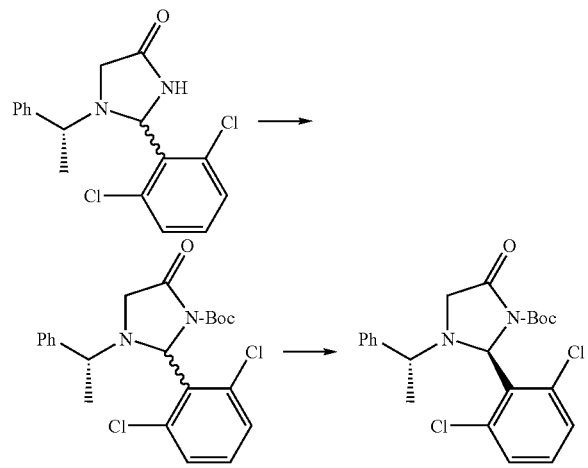

Under nitrogen stream, di-t-butyl dicarbonate (57.5 g, 0.26 mol), triethylamine (26.8 g, 0.26 mol) and 4-(N,N-dimethylamino)pyridine (1.1 g, 9 mmol) were added at 0° C. to 296 ml of an acetonitrile solution containing (2,6-dichlorophenyl)-1-((1'R)-phenylethyl)tetrahydro-1H-4-imidazolone (59 g, 0.18 mol) obtained in Example 3. The mixture was stirred at room temperature for 12 hours. After the reaction mixture was concentrated, the residue was diluted with ethyl acetate and subjected to treatment by a column tube filled with a small amount of silica gel to remove highly polar substance. The obtained filtrate was concentrated to obtain 77 g of a crude product. The product was subjected to crystallization in ethyl acetate and hexane, and further the crystal was dried in vacuum at 40° C. to obtain 33.2 g as a white crystal (yield: 32%, recovery ratio based on the 2S isomer content: 64%, 99.7% de).

$^1$H-NMR (400 MHz, CDCl$_3$): δ7.26-7.10 (8H, m), 6.43 (1H, t, J=1.2 Hz), 3.95 (1H, q, J=6.3 Hz), 3.53 (2H, d, J=1.2 Hz), 1.48 (3H, d, J=6.3 Hz), 1.24 (9H, s)

Example 12

1,1-Dimethylethyl-(2R)-(2,6-dichlorophenyl)-5-oxo-3-((1'R)-phenylethyl)-(4S)-(phenylmethyl)tetrahydro-1H-1-imidazolecarboxylate

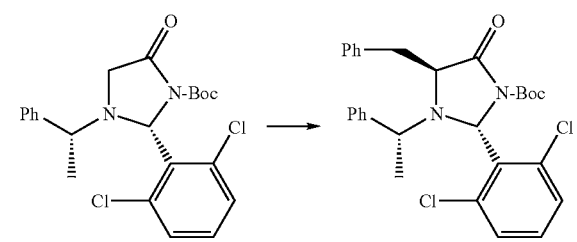

Under nitrogen stream, n-butyllithium (4.5 ml, 1.6 mol/L; n-hexane solution, 7.2 mmol) was added dropwise at −20° C. over 10 minutes to an anhydrous tetrahydrofuran solution (11.5 ml) containing a very small amount of 1,10-phenanthroline (5 mg or less) and diisopropylamine (1.15 ml, 8.2 mmol). After 20 minutes, an anhydrous tetrahydrofuran solution (6 ml) containing 1,1-dimethylethyl-(2R)-(2,6-dichlorophenyl)-5-oxo-3-((1'R)-phenylethyl)tetrahydro-1H-1-imidazolecarboxylate (3.0 g, 6.8 mmol) obtained in Example 9 was added dropwise over 10 minutes. After an equipment used for the dropwise addition was washed with 1.5 ml of anhydrous tetrahydrofuran, aging was carried out at −20° C. for 20 minutes. To the mixture was added dropwise benzyl bromide (1.75 g, 10.2 mmol). The mixture was stirred at −20° C. for 1 hour and thereafter at 0° C. for 15.5 hours. The reaction mixture was diluted with ethyl acetate (100 ml); and then, the mixture was washed with an aqueous solution of ammonium chloride, and distilled water and saturated brine respectively twice; and anhydrous magnesium sulfate was added to the obtained organic layer for drying. After the solid product was separated by filtration, the solvent was removed by distillation in reduced pressure to obtain 4.51 g of a crude product. The product was made to be a slurry and washed with hexane to obtain 2.8 g of the title compound as a slight brownish crystal (yield: 77%).

$^1$H-NMR (400 MHz, CDCl$_3$): δ7.33-7.02 (13H, m), 6.18 (1H, d, J=2.2 Hz), 4.27 (1H, m), 3.98 (1H, q, J=6.8 Hz), 3.29

(1H, dd, J=2.7 Hz, 14.2 Hz), 3.08 (1H, dd, J=6.1 Hz, 14.2 Hz), 1.31 (3H, d, J=6.8 Hz), 1.2 (9H, s)

Example 13

(S)-Phenylalanine

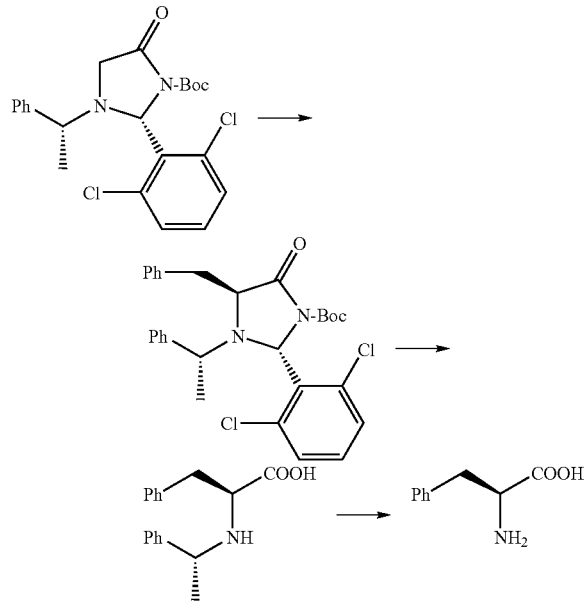

Step 1: Under nitrogen stream, n-butyllithium (4.1 ml, 1.6 mol/L; n-hexane solution, 6.5 mmol) was added dropwise at −15° C. over 5 minutes to an anhydrous tetrahydrofuran solution (12 ml) containing a very small amount of 1,10-phenanthroline (5 mg or less) and diisopropylamine (1.01 ml, 7.1 mmol). After 30 minutes, an anhydrous tetrahydrofuran solution (4 ml) containing 1,1-dimethylethyl-(2R)-(2,6-dichlorophenyl)-5-oxo-3-((1'R)-phenylethyl)tetrahydro-1H-1-imidazolecarboxylate (2.5 g, 5.7 mmol) obtained in Example 9 was added dropwise over 5 minutes. After an equipment used for the dropwise addition was washed with 2 ml of anhydrous tetrahydrofuran, aging was carried out at −15° C. for 20 minutes. An anhydrous tetrahydrofuran solution (2.2 ml) containing benzyl bromide (1.1 g, 6.5 mmol) was added dropwise thereto, and the mixture was stirred at −15° C. for 1 hour and thereafter at 0° C. for 20 hours. The reaction mixture was diluted with ethyl acetate (50 ml), and then, was washed with an aqueous solution of ammonium chloride, distilled water and saturated brine respectively twice, and anhydrous magnesium sulfate was added to the obtained organic layer for drying. After the solid product was separated by filtration, the solvent was removed by distillation in reduced pressure to obtain 3.2 g of a crude product. The crude product was led to the next step without further purification.

Step 2: After 1.6 g (1/2 weight obtained in Step 1) of the crude product of Step 1 was suspended in 8 ml of ethanol and 1 ml of distilled water, concentrated sulfuric acid (3.0 g, 30 mmol) was added and reaction was carried out at 60° C. for 24 hours. After 3.2 ml of distilled water was added thereto, ethanol was removed in reduced pressure. The aqueous solution was washed with 20 ml of toluene 4 times and thereafter the organic solvent was again removed in reduced pressure. To the obtained aqueous solution was added concentrated sulfuric (1.5 g, 15 mmol) acid, and reaction was carried out at an outer temperature of 120 to 130° C. for 16.5 hours to obtain 3-phenyl-(2S)-[(1'R)-phenylethylamino]propionic acid (conversion ratio: 99.8%). The compound was led to the next step without further purification.

Step 3: After 12 ml of ethanol and 2 ml of distilled water were added to the aqueous solution of 3-phenyl-(2S)-[(1'R)-phenylethylamino]propionic acid obtained in Step 2, 20% palladium-carbon (200 mg, 50% wet) was added at room temperature under nitrogen stream. The atmosphere of the reaction vessel was replaced with hydrogen gas and reaction was carried out at 50° C. for 2.5 hours (conversion ratio: 99.6%). After the catalyst was separated by filtration and washed with distilled water, the pH was adjusted to 3.5 with a 30% aqueous solution of sodium hydroxide. The quantity of phenylalanine in the resulting solution was determined by high performance liquid chromatography; and as a result, 218.1 mg of (S)-phenylalanine having an optical purity of 99.5% ee was obtained (total yield: 46.4%).

Quantitative Analysis Method

Column: Chiral Pack WH (inner diameter: 4.6 mm×25 cm) manufactured by Daicel Chemical Industries, Ltd.

Mobile phase: 0.25 mM aqueous copper sulfate solution

Flow rate: 1.0 ml/min

Detector: UV 254 nm

Retention time: (R)-phenylalanine—25.8 minutes
(S)-phenylalanine—46.8 minutes

Example 14

(R)-Phenylalanine

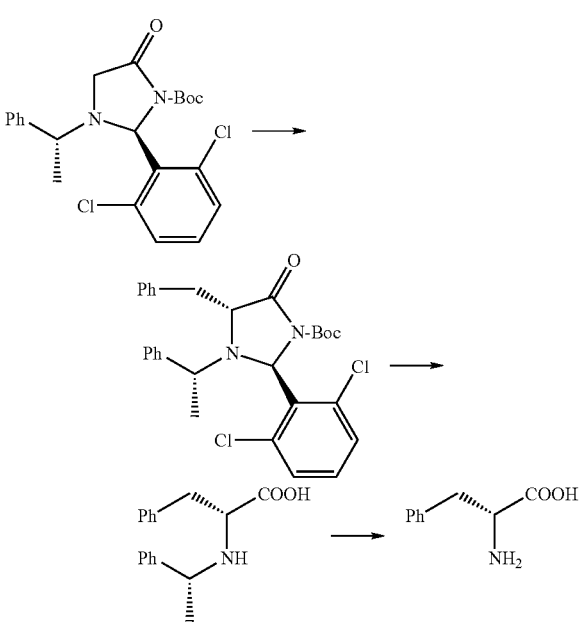

Step 1: Under nitrogen stream, n-butyllithium (8.5 ml, 1.6 mol/L; n-hexane solution, 13.6 mmol) was added dropwise at −15° C. over 5 minutes to an anhydrous tetrahydrofuran solution (20 ml) containing a very small amount of 1,10-phenanthroline (5 mg or less) and diisopropylamine (2.11 ml, 14.8 mmol). After 30 minutes, an anhydrous tetrahydrofuran solution (10 ml) containing 1,1-dimethylethyl-(2S)-(2,6-dichlorophenyl)-5-oxo-3-((1'R)-phenylethyl)tetrahydro-1H-1-imidazolecarboxylate (5.2 g, 11.8 mmol) obtained in Example 11 was added dropwise over 5 minutes. After an equipment used for the dropwise addition was washed with 2.5 ml of anhydrous tetrahydrofuran, aging was carried out at −15° C. for 25 minutes. An anhydrous tetrahydrofuran solution (4.6 ml) containing benzyl bromide (2.3 g, 13.6 mmol) was added dropwise thereto, and the mixture was stirred at −15° C. for 1.5 hours and thereafter at 0° C. for 18 hours. The reaction mixture was diluted with ethyl acetate (100 ml), and then, was washed with an aqueous solution of ammonium chloride, distilled water and saturated brine respectively twice. To the obtained organic layer was added anhydrous magnesium sulfate for drying. After the solid product was separated by filtration, the solvent was removed by distillation in reduced pressure to obtain 7.3 g of a crude product. The crude product was led to the next step without further purification.

Step 2: To the crude product (7.3 g) of Step 1 were added 30 ml of methanol, 20 ml of concentrated hydrochloric acid and 5 ml of distilled water; and reaction was carried out at 50° C. for 14 hours. After 20 ml of methanol was further added and reaction was carried our furthermore for 4 hours, the mixture was stirred at room temperature for 3.5 hours. After the reaction mixture was concentrated in reduced pressure, the water layer was washed with 20 ml of toluene 4 times. To the mixture was added 6.4 g of concentrated sulfuric acid; and reaction was carried out at an outer temperature of 120 to 130° C. for 3 hours (conversion ratio: 97%) and thereafter, the reaction mixture was cooled to room temperature. After 520 mg of activated carbon was added thereto and the mixture was stirred for 0.5 hours, the solid material was separated by filtration. The residue was washed with distilled water/ethanol (1/1 by volume) to obtain a solution containing 3-phenyl-(2R)-[(1'R)-phenylethylamino]propionic acid. The compound was led to the next step without further purification.

Step 3: Under nitrogen stream, 20% palladium-carbon (600 mg, 50% wet) was added at room temperature to an aqueous solution of 3-phenyl-(2R)-[(1'R)-phenylethylamino]propionic acid obtained in Step 2. The atmosphere of the reaction vessel was replaced with hydrogen gas and reaction was carried out at 50° C. for 20 hours (conversion ratio: 65.6%). After the catalyst was separated by filtration and washed with distilled water, 20% palladium-carbon (500 mg, 50% wet) was newly added under nitrogen stream. The atmosphere of the reaction vessel was replaced with hydrogen gas and reaction was carried out at 50° C. for 5 hours (conversion ratio: 95%). After the catalyst was separated by filtration and washed with distilled water, the pH was adjusted to 3.5 with a 30% aqueous solution of sodium hydroxide. The quantity of phenylalanine in the resulting solution was determined by high performance liquid chromatography in the same manner as in Example 12; and as a result, 606.9 mg of (R)-phenylalanine having an optical purity of 99.8% ee was obtained (total yield: 31.0%).

Example 15

(S)-Norvaline

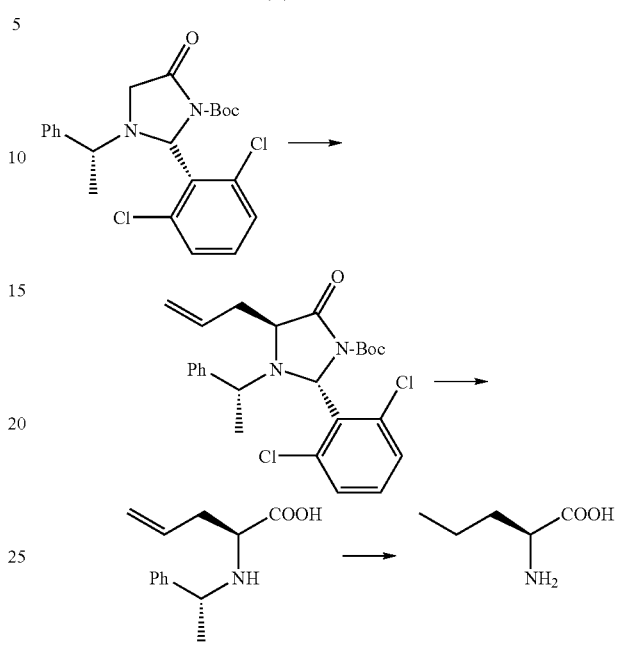

Step 1: Under nitrogen stream, n-butyllithium (8.2 ml, 1.6 mol/L; n-hexane solution, 13.1 mmol) was added dropwise at −15° C. over 10 minutes to an anhydrous tetrahydrofuran solution (20 ml) containing a very small amount of 1,10-phenanthroline (5 mg or less) and diisopropylamine (2.0 ml, 14.2 mmol). After 30 minutes, an anhydrous tetrahydrofuran solution (10 ml) containing 1,1-dimethylethyl-(2R)-(2,6-dichlorophenyl)-5-oxo-3-((1'R)-phenylethyl)tetrahydro-1H-1-imidazolecarboxylate (5.2 g, 11.8 mmol) obtained by the method in Example 9 was added dropwise over 10 minutes. After an equipment used for the dropwise addition was washed with 2.5 ml of anhydrous tetrahydrofuran, aging was carried out at −15° C. for 25 minutes. To the mixture was added dropwise allyl bromide (1.8 g, 14.9 mmol). The mixture was stirred at −15° C. for 1 hour and thereafter at 0° C. for 19 hours. The reaction mixture was diluted with ethyl acetate (100 ml), and then, washed with an aqueous solution of ammonium chloride, distilled water and saturated brine respectively twice. To the obtained organic layer was added anhydrous magnesium sulfate for drying. After the solid product was separated by filtration, the solvent was removed by distillation in reduced pressure to obtain 5.8 g of a crude product. The crude product was led to the next step without further purification. A portion of the product was purified with a thin-layer silica gel plate (Merk Silica Gel Plate 60, 200×200×0.25 mm; three sheets, eluent: hexane/ethyl acetate=3/1 by volume) and NMR spectrum of the product was obtained.

$^1$H-NMR (400 MHz, CDCl$_3$): δ7.33-7.10 (8H, m), 6.59 (1H, d, J=2.4 Hz), 5.94 (1H, m), 5.20 (1H, d, J=0.7 Hz), 5.17 (1H, dd, J=2.0 Hz, 8.8 Hz), 4.12 (1H, m), 3.88 (1H, q, J=6.8 Hz), 2.68-2.54 (2H, m), 1.29-1.26 (12H, m)

Step 2: After 28 ml of methanol, 11.5 ml of concentrated hydrochloric acid and 11.5 ml of distilled water were added to the crude product of Step 1, reaction was carried out at 50° C.

for 18 hours. The reaction mixture was concentrated in reduced pressure to remove methanol; and thereafter, the water layer was washed with 25 ml of toluene 4 times. To the aqueous layer was added 2.3 g of concentrated sulfuric acid, and reaction was carried out at an outer temperature of 120 to 130° C. for 4 hours (conversion ratio: 100%). Then, the reaction mixture was cooled to room temperature. After 300 mg of activated carbon was added to the reaction mixture and the mixture was stirred for 0.5 hours, the solid material was separated by filtration. The residue was washed with distilled water to obtain a solution containing (2S)-[(1'R)-phenylethylamino]-4-pentenoic acid. The compound was led to the next step without further purification.

Step 3: Under nitrogen stream, 20% palladium-carbon (600 mg, 50% wet) was added to the aqueous solution of (2S)-[(1'R)-phenylethylamino]-4-pentenoic acid obtained in Step 2 at room temperature. The atmosphere of the reaction vessel was replaced with hydrogen gas, and reaction was carried out at 50° C. for 27 hours. After the catalyst was separated by filtration and washed with distilled water, 20% palladium-carbon (500 mg, 50% wet) was newly added under nitrogen stream. The atmosphere of the reaction vessel was replaced with hydrogen gas, and reaction was carried out at 50° C. for 20 hours under 2.2 MPa of hydrogen pressure. After the catalyst was separated by filtration and washed with distilled water, the pH was adjusted to 3.5 with a 30% aqueous solution of sodium hydroxide. The quantity of norvaline in the resulting solution was determined by high performance liquid chromatography; and as a result, 573 mg of (S)-norvaline having an optical purity of 98.7% ee was obtained (total yield: 41.5%).

Quantitative Analysis Method
Column: Sumichiral OA-5000 (inner diameter: 4.6 mm×15 cm) manufactured by Sumitomo Chemical Co., Ltd.
Mobile phase: 2 mM aqueous solution of copper sulfate/methanol=95/5 (volume ratio)
Flow rate: 1.0 ml/min
Detector: UV 254 nm
Retention time: (S)-norvaline—12.2 minutes
(R)-norvaline—19.8 minutes Example 16

(R)-Norvaline

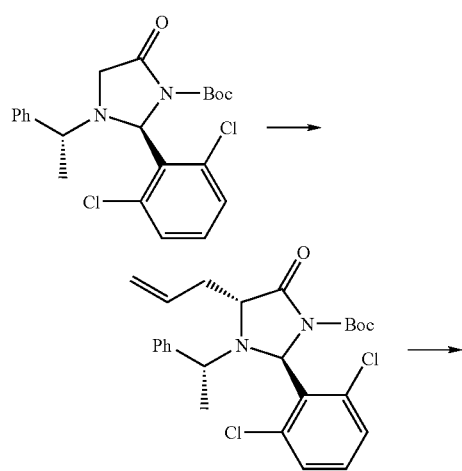

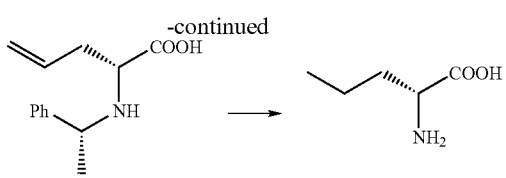

Step 1: Under nitrogen stream, n-butyllithium (8.5 ml, 1.6 mol/L; n-hexane solution, 13.6 mmol) was added dropwise at −15° C. over 5 minutes to an anhydrous tetrahydrofuran solution (20 ml) containing a very small amount of 1,10-phenanthroline (5 mg or less) and diisopropylamine (2.1 ml, 14.8 mmol). After 30 minutes, an anhydrous tetrahydrofuran solution (10 ml) containing 1,1-dimethylethyl-(2S)-(2,6-dichlorophenyl)-5-oxo-3-((1'R)-phenylethyl)tetrahydro-1H-1-imidazolecarboxylate (5.2 g, 11.8 mmol) obtained in Example 11 was added dropwise over 10 minutes. After an equipment used for the dropwise addition was washed with 2.5 ml of anhydrous tetrahydrofuran, aging was carried out at −15° C. for 25 minutes. To the mixture was added dropwise allyl bromide (1.8 g, 14.9 mmol), and the mixture was stirred at −15° C. for 1 hour and thereafter at 0° C. for 18 hours. The reaction mixture was diluted with ethyl acetate (100 ml), and then was washed with an aqueous solution of ammonium chloride, distilled water and saturated brine respectively twice. To the obtained organic layer was added anhydrous magnesium sulfate for drying. After the solid product was separated by filtration, the solvent was removed by distillation in reduced pressure to obtain 5.8 g of a crude product. The crude product was led to the next step without further purification. A portion of the product was purified with a thin-layer silica gel plate (Merk Silica Gel Plate 60, 200×200×0.25 mm; three sheets, eluent: hexane/ethyl acetate=3/1 by volume) and NMR spectrum of the product was obtained.

$^1$H-NMR (400 MHz, CDCl$_3$): δ7.31-7.12 (8H, m), 6.66 (1H, d, J=2.4 Hz), 5.90 (1H, m), 5.15 (1H, s), 5.11 (1H, dd, J=1.5 Hz, 5.4 Hz), 4.00 (1H, q, J=6.8 Hz), 3.81 (1H, m), 2.50-2.39 (2H, m), 1.26-1.24 (12H, m)

Step 2: To the crude product of Step 1 were added, 30 ml of methanol, 15 ml of concentrated hydrochloric acid and 11.5 ml of distilled water; and reaction was carried out at 50° C. for 15 hours. To the mixture was added 2.3 g of concentrated sulfuric acid; and reaction was carried out at an outer temperature of 120 to 130° C. for 4.5 hours (conversion ratio: 92%). Then, the reaction mixture was cooled to room temperature. After 300 mg of activated carbon was added to the reaction mixture and the mixture was stirred for 0.5 hours, the solid material was separated by filtration. The residue was washed with distilled water to obtain a solution containing (2R)-[(1'R)-phenylethylamino]-4-pentenoic acid. The compound was led to the next step without further purification.

Step 3: Under nitrogen stream, methanol and 20% palladium-carbon (500 mg, 50% wet) were added to the aqueous solution of (2R)-[(1'R)-phenylethylamino]-4-pentenoic acid obtained in Step 2 at room temperature. The atmosphere of the reaction vessel was replaced with hydrogen gas, and reaction was carried out at 50° C. for 20 hours. After the catalyst was separated by filtration and washed with distilled water, methanol was removed in reduced pressure. After isopropanol and 20% palladium-carbon (250 mg, 50% wet) were newly added under nitrogen stream, the atmosphere of the reaction vessel was replaced with hydrogen gas and reaction was carried out at 50° C. for 20 hours under 2.2 MPa of hydrogen pressure. After the catalyst was separated by filtration and washed with distilled water, the pH was adjusted to 3.5 with a 30% aqueous solution of sodium hydroxide. The quantity of norvaline in the resulting solution was determined by the same method as that in Example 15; and as a result, 588 mg of (R)-norvaline having an optical purity of 99.6% ee was obtained (total yield: 42.6%).

Example 17

1,1-Dimethylethyl-(2S)-(3,4-dichlorophenyl)-5-oxo-3-((1'R)-phenylethyl)tetrahydro-1H-1-imidazolecarboxylate and 1,1-dimethylethyl-(2R)-(3,4-dichlorophenyl)-5-oxo-3-((1'R)-phenylethyl)tetrahydro-1H-1-imidazolecarboxylate

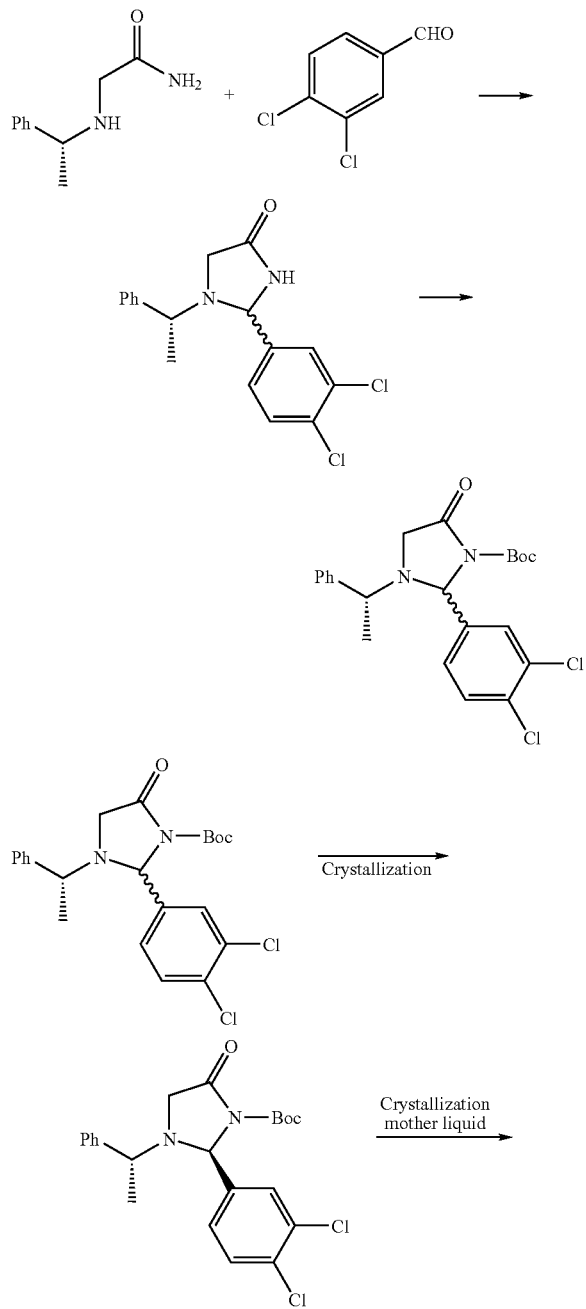

-continued

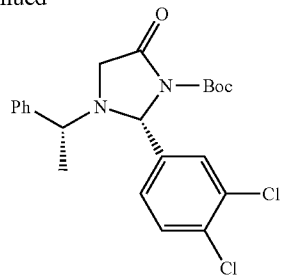

Step 1: Under nitrogen stream, a toluene solution (50 ml) containing (R)-2-[(1-phenylethyl)amino]-ethanamide (5.0 g, 28 mmol), 3,4-dichlorobenzaldehyde (4.9 g, 28 mmol) and p-toluenesulfonic acid (265 mg, 1.4 mmol) was refluxed at an outer temperature of 120 to 130° C. for 18 hours. The reaction mixture was cooled to room temperature, and then was concentrated to obtain a crude product. High polar impurities were removed by short-pass silica gel column chromatography (Merk Silica Gel 60; 75 g, eluent: hexane/ethyl acetate=1/1 by volume), and 4.96 g of an isomeric mixture of (2R)-(3,4-dichlorophenyl)-1-((1'R)-phenylethyl)tetra-hydro-1H-4-imidazolone and (2S)-(3,4-dichloro-phenyl)-1-((1'R)-phenylethyl)tetrahydro-1H-4-imidazolone was obtained (yield: 52.8%). A portion of the product was purified with a thin-layer silica gel plate (Merk Silica Gel Plate; 200× 200×0.25 mm, three sheets; eluent:hexane/ethyl acetate=3/1 by volume), and NMR spectrum of the product was obtained.

$^1$H-NMR (2S isomer) (400 MHz, CDCl$_3$): δ7.26-6.84 (8H, m), 4.97 (1H, d, J=1.7 Hz), 3.71 (1H, q, J=6.6 Hz), 3.61 (1H, dd, J=1.7 Hz, 14.9 Hz), 3.33 (1H, dd, J=2.0 Hz, 14.9 Hz), 1.39 (3H, d, J=6.6 Hz)

$^1$H-NMR (2R isomer) (400 MHz, CDCl$_3$): δ7.55-6.95 (8H, m), 5.09 (1H, s), 3.59 (1H, q, J=6.8 Hz), 3.45 (1H, dd, J=2.0 Hz, 14.9 Hz), 3.23 (1H, dd, J=2.0 Hz, 14.9 Hz), 1.38 (3H, d, J=6.8 Hz)

Step 2: Under nitrogen stream, triethylamine (2.1 g, 14 mmol), di-t-butyl dicarbonate (3.9 g, 16.8 mmol) and 4-(N, N-dimethyl amino)pyridine (170 mg, 1.4 mmol) were added to an anhydrous acetonitrile solution (50 ml) containing the isomeric mixture (4.96 g, 14 mmol) obtained in Step 1, and the mixture was stirred at room temperature for 16 hours. After the reaction mixture was concentrated, high polar impurities were removed by short-pass silica gel column chromatography (Merk Silica Gel 60; 20 g, eluent: hexane/ethyl acetate=1/1 by volume) was carried out to obtain 9.5 g of the title isomeric mixture. A portion of the product was purified with a thin-layer silica gel plate (Merk Silica Gel Plate; 200× 200×0.25 mm, three sheets; eluent: hexane/ethyl acetate=3/1 by volume), and NMR spectrum of the product was obtained. Further, these purified isomers were used as seed crystals in Step 3.

$^1$H-NMR (2S isomer) (400 MHz, CDCl$_3$): δ7.33-7.01 (8H, m), 5.43 (1H, s), 3.74 (1H, q, J=6.6 Hz), 3.62 (1H, d, J=16.4 Hz), 3.48 (1H, d, J=16.4 Hz), 1.42 (3H, d, J=6.6 Hz), 1.30 (9H, s)

$^1$H-NMR (2R isomer) (400 MHz, CDCl$_3$): δ7.44-7.07 (8H, m), 5.44 (1H, s), 3.64 (1H, dd, J=0.7 Hz, 15.9 Hz), 3.59 (1H, q, J=6.6 Hz), 3.51 (1H, dd, J=0.7 Hz, 16.4 Hz), 1.35-1.32 (12H, m)

Step 3: To the isomeric mixture obtained in Step 2, 30 ml of ethyl acetate/hexane (1/3 by volume) was added, and the mixture was stirred at room temperature. The crystal of the (2S) isomer obtained in Step 2 was added to the obtained solution as a seed, and further 50 ml of hexane was added thereto. Thereafter, the resulting mixture was stirred at room temperature for 1 hour. The precipitated crystal was filtered and washed successively with an ethyl acetate/hexane (1/7 by volume) solution and hexane, and then dried at 40° C. in reduced pressure. After the mother liquid was concentrated, similar crystallization operation using 10 ml of ethyl acetate and 100 ml of hexane was furthermore carried out to obtain 1,1-dimethylethyl-(2S)-(3,4-dichlorophenyl)-5-oxo-3-((1'R)-phenylethyl)tetrahydro-1H-1-imidazolecarboxylate in total of 2.14 g as a white crystal (yield: 35.2%, 100% de).

Step 4: The mother liquid obtaine from the (2S) isomer being separated in Step 3 was concentrated; and thereafter, the crystallization operation was carried out in 100 ml of hexane to obtain 1.23 g of 1,1-dimethylethyl-(2R)-(3,4-dichlorophenyl)-5-oxo-3-((1'R)-phenylethyl)tetrahydro-1H-1-imidazolecarboxylate as a white crystal (yield: 20%).

Example 18

3-Phenyl-(2S)-[(1'R)-phenylethylamino]propionic acid

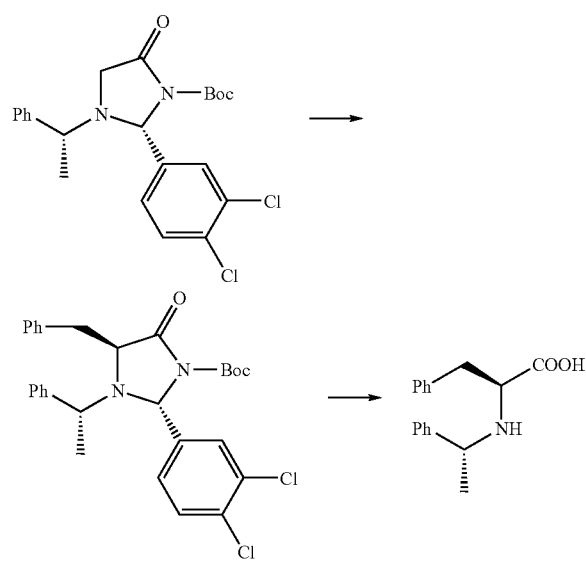

Step 1: Under nitrogen stream, lithium diisopropylamide (3.2 ml, 2.0 mol/L; heptane/tetrahydrofuran/ethylbenzene solution, 6.3 mmol) was added dropwise at −15° C. over 10 minutes to an anhydrous tetrahydrofuran solution (20 ml) containing a very small amount of 1,10-phenanthroline (5 mg or less) and 1,1-dimethylethyl-(2S)-(3,4-dichlorophenyl)-5-oxo-3-((1'R)-phenylethyl)tetrahydro-1H-1-imidazolecarboxylate (2.5 g, 5.7 mmol) obtained in Example 17. After 15 minutes, an anhydrous tetrahydrofuran solution (5 ml) containing benzyl bromide (1.5 g, 8.5 mmol) was added dropwise. The mixture was stirred at −15° C. for 19 hours. The reaction mixture was diluted with ethyl acetate (150 ml), and then was washed with distilled water, an aqueous solution of ammonium chloride and distilled water respectively once and with saturated brine twice. To the obtained organic layer was added anhydrous magnesium sulfate for drying. After the solid product was separated by filtration, the solvent was removed by distillation in reduced pressure to obtain 3.9 g of a crude product. The product was purified by silica gel column chromatography (Merk Silica Gel 60, 420 g and 100 g respectively once, eluent: hexane/ethyl acetate=3/1 by volume) to obtain 1.1 g of an isomeric mixture (yield: 37%) containing an excess amount of 1,1-dimethylethyl-(2R)-(3,4-dichlorophenyl)-5-oxo-3-((1'R)-phenylethyl)-(4S)-(phenylmethyl)tetrahydro-1H-1-imidazolecarboxylate as an oily material. In the case, 1.4 g of a starting material was recovered; and the yield was 84% in consideration of the recovery.

$^1$H-NMR (400 MHz, CDCl$_3$): δ7.25-7.17 (10H, m), 7.03 (2H, m), 6.78 (1H, d, J=2.2 Hz), 6.69 (1H, m), 4.17 (1H, t, 4.2 Hz), 3.82 (1H, q, J=6.8 Hz), 3.33-3.24 (2H, m), 1.37 (3H, d, J=6.8 Hz), 1.28 (9H, s)

Step 2: Under nitrogen stream, 18 ml of tetrahydrofuran, 6 ml of distilled water and lithium hydroxide monohydrate (168 mg, 4 mmol) were added at 0° C. to 1.0 g of the crude product (84%, content: 840 mg, 1.6 mmol) obtained in Step 1, and reaction was carried out at 0° C. for 22.5 hours. Tetrahydrofuran was removed in reduced pressure. The mixture was washed by added ethyl acetate, and the organic layer was discarded. The pH of the aqueous layer was adjusted to 2.5 with a 6 M hydrochloric acid. The aqueous layer was washed by added ethyl acetate, and the organic layer was discarded. The pH of the aqueous solution was adjusted to 6.5; as a result, an amino acid crystal was precipitated. The crystal was separated by filtration, and dried in reduced pressure to obtain 337 mg of the title compound as an off-white solid (yield: 78%). The optical purity of the solid was measured by high performance liquid chromatography; and as a result, 3-phenyl-(2S)-[(1'R)-phenylethylamino]propionic acid was obtained at 59.3% de.

Optical Purity Measurement Method
Column: Symmetry C18 (inner diameter: 4.6 mm×25 cm) manufactured by Waters Corporation
Mobile phase: 50 mM aqueous solution of disodium hydrogen phosphate (pH 2.5)/acetonitrile=75/25 (volume ratio)
Flow rate: 0.5 ml/min
Column temperature: 35° C.
Detector: UV 254 nm
Retention time: (2S) isomer—about 16 minutes
(2R) isomer about −13 minutes Example 19

(R)-α-Methylphenylalanine

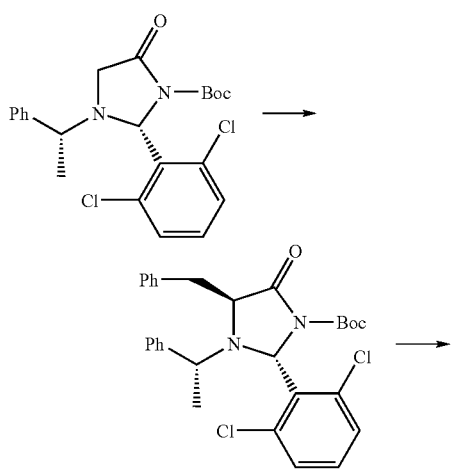

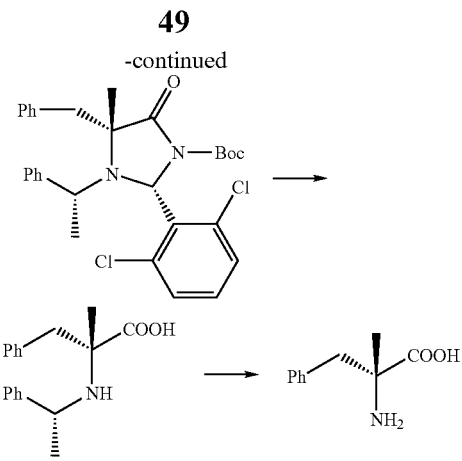

Step 1: Under nitrogen stream, n-butyllithium (1.3 ml, 1.6 mol/L; n-hexane solution, 2.0 mmol) was added dropwise at −20° C. over 10 minutes to an anhydrous tetrahydrofuran solution (5 ml) containing a very small amount of 1,10-phenanthroline (5 mg or less) and diisopropylamine (0.32 ml, 2.3 mmol). After 20 minutes, an anhydrous tetrahydrofuran solution (3.5 ml) containing 1,1-dimethylethyl-(2R)-(2,6-dichlorophenyl)-5-oxo-3-((1'R)-phenylethyl)-(4S)-(phenylmethyl)tetrahydro-1H-1-imidazolecarboxylate (1.0 g, 1.9 mmol) obtained in Example 9 was added dropwise over 10 minutes. After an equipment used for the dropwise addition was washed with 0.5 ml of anhydrous tetrahydrofuran, aging was carried out at −20° C. for 20 minutes. To the mixture was added dropwise methyl iodide (405 mg, 2.9 mmol). The mixture was stirred at −20° C. for 1 hour and thereafter at 0° C. for 16 hours. The reaction mixture was diluted with ethyl acetate (50 ml), and then was washed with an aqueous solution of ammonium chloride, distilled water and saturated brine respectively twice. To the obtained organic layer, anhydrous magnesium sulfate was added for drying. After the solid product was separated by filtration, the solvent was removed by distillation in reduced pressure to obtain 1.0 g of a crude product. The crude product was led to the next step without further purification. A portion (1/10 weight) was purified by using a thin-layer silica gel plate (Merk Silica Gel Plate 60, 200×200×0.25 mm; 1/5 sheets, eluent: hexane/ethyl acetate=3/1 by volume), and NMR spectrum of the product was obtained.

1,1-Dimethylethyl-(2R)-(2,6-dichlorophenyl)-(4R)-methyl-5-oxo-3-((1'R)-phenylethyl)-4-(phenylmethyl)tetrahydro-1H-1-imidazolecarboxylate $^1$H-NMR (400 MHz, CDCl$_3$): δ7.40-6.75 (13H, m), 6.41 (1H, s), 4.33 (1H, q, J=6.8 Hz), 3.63 (1H, d, J=14.2 Hz), 3.37 (1H, d, J=14.2 Hz), 1.76 (3H, d, J=6.8 Hz), 1.38 (3H, s), 1.19 (9H, s)

Step 2: After 35 ml of methanol and 10 ml of concentrated hydrochloric acid were added to 0.9 g of the crude product of Step 1, reaction was carried out at 50° C. for 2 hours. After methanol was removed in reduced pressure for concentration, 20 ml of distilled water was added and further 0.75 g of concentrated sulfuric acid was added thereto, and reaction was carried out at an outer temperature of 120 to 130° C. for 7 hours (conversion ratio: 100%). The reaction mixture was cooled to room temperature. After 200 mg of activated carbon was added to the reaction mixture and the mixture was stirred for 0.5 hours, the solid material was separated by filtration. The residue was washed with distilled water to obtain a solution containing (2R)-methyl-3-phenyl-[(1'R)-phenylethylamino]propionic acid. The compound was led to the next step without further purification.

Step 3: After isopropanol was added to an aqueous solution of (2R)-methyl-3-phenyl-[(1'R)-phenylethylamino]propionic acid obtained in Step 2, 20% palladium-carbon (200 mg, 50% wet) was added under nitrogen stream. The atmosphere of the reaction vessel was replaced with hydrogen gas, and reaction was carried out at 50° C. for 20 hours (conversion ratio: 100%). After the catalyst was separated by filtration and washed with distilled water, the pH was adjusted to 4.0 by a 30% aqueous solution of sodium hydroxide. The quantity of α-methyl-phenylalanine in the resulting solution was determined by high performance liquid chromatography as same as in Example 13; and as a result, 154.9 mg of (R)-α-methyl-phenylalanine having an optical purity of 100% ee was obtained (total yield: 51%).

Quantitative analysis and optical purity analysis condition
Column: Chiral Pack WH (inner diameter: 4.6 mm×25 cm) manufactured by Daicel Chemical Industries, Ltd.
Mobile phase: 2 mM aqueous solution of copper sulfate/methanol=95/5 (volume ratio)
Flow rate: 0.6 ml/min
Detector: UV 254 nm
Retention time: (R)-α-methyl-phenylalanine—about 16 minutes
(S)-α-methyl-phenylalanine—about 42 minutes Example 20

(2,4,6-Trimethylphenyl)-1-((1R')-phenylethyl)tetrahydro-1H-imidazolene

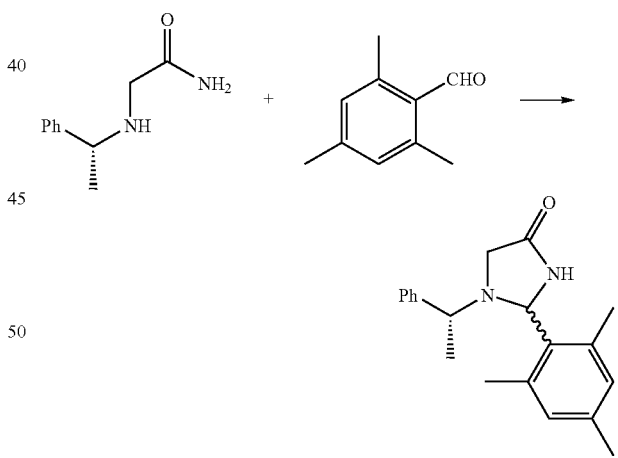

Under nitrogen stream, a toluene solution (50 ml) containing (R)-2-[(1-phenylethyl)amino]-ethanamide (31.6 g, 0.18 ml) obtained in Example 1,2,4,6-trimethylbenzaldehyde (25 g, 0.18 mol) and p-toluenesulfonic acid (805 mg, 4.2 mmol) was refluxed at an outer temperature of 120 to 130° C. for 22 hours. The reaction mixture was cooled to room temperature, and then was concentrated to obtain a crude product. High polar impurities were removed by silica gel column treatment (Merk Silica Gel 60, 600 g: eluent: hexane/ethyl acetate=3/2 by volume), and the obtained eluate was concentrated to obtain 53 g of the title compound as a brown oily material.

$^1$H-NMR (400 MHz, CDCl$_3$): δ7.33-7.19 (6H, m), 7.03 (4H, s), 6.82 (2H, s), 6.63 (2H, s), 6.06 (2H, brs), 5.62 (1H, t, J=2.2 Hz), 5.60 (1H, t, J=2.0 Hz), 3.75 (1H, q, J=6.6 Hz), 3.70 (1H, q, J=6.8 Hz), 3.48-3.34 (3H, m), 3.14 (1H, dd, J=2.2, 14.9 Hz), 3.49 (6H, s), 2.28 (6H, s), 2.25 (3H, s), 2.17 (3H, s), 1.39 (3H, d, J=6.6 Hz), 1.10 (3H, d, J=6.6 Hz)

Example 21

1,1-Dimethylethyl-(2S)-(2,4,6-trimethylphenyl)-5-oxo-3-((1R')-phenylethyl)tetrahydro-1H-1-imidazolecarboxylate

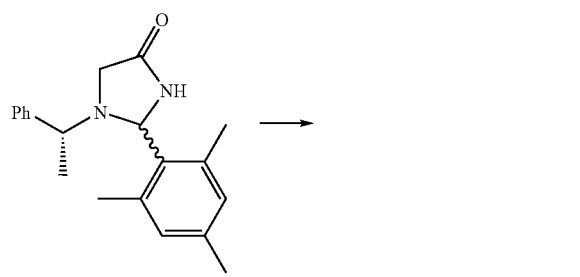

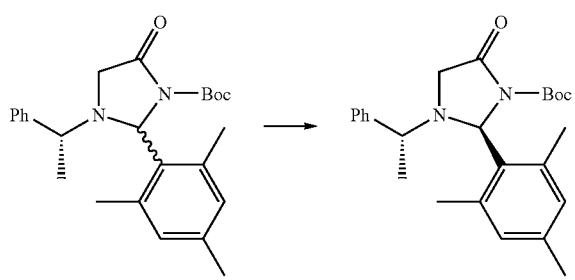

Under nitrogen stream, di-t-butyl dicarbonate (56.2 g, 0.26 mmol), triethylamine (26 g, 0.26 mol) and 4-(N,N-dimethylamino)pyridine (520 mg, 4.3 mmol) were added at 0° C. to 215 ml of an ethyl acetate solution containing (2,4,6-trimethylphenyl)-1-((1'R)-phenylethyl)tetrahydro-1H-4-imidazolone (53 g, 0.17 mmol) obtained in Example 20. The mixture was stirred at room temperature for 17 hours. After the reaction mixture was concentrated, high polar impurities were removed by silica gel column treatment (Merk Silica Gel 60, 700 g: eluent: hexane/ethyl acetate=5/1 by volume). The obtained eluate was concentrated to obtain 58.4 g of a product. The product was dissolved in 230 ml of hexane, and aging was carried out at a crystallization temperature of –10° C. for 64 hours. The crystal was separated by filtration, washed with 50 ml of ice-cooled hexane twice, dried in vacuum to obtain 17.6 g of the title compound as a white crystal (yield based on 2,4,6-trimethylbenzaldehyde: 25.6%, 100% de).

$^1$H-NMR (400 MHz, CDCl$_3$): δ7.25-7.07 (5H, m), 6.77 (2H, brs), 5.97 (1H, s), 3.87 (1H, q, J=6.8 Hz), 3.45 (1H, dd, J=2.2 Hz, 15.4 Hz), 3.29 (1H, dd, J=0.7 Hz, 15.4 Hz), 2.41 (6H, brs), 2.25 (3H, s), 1.46 (3H, d, J=6.8 Hz), 1.17 (9H, s)

Example 22

(R)-Phenylalanine

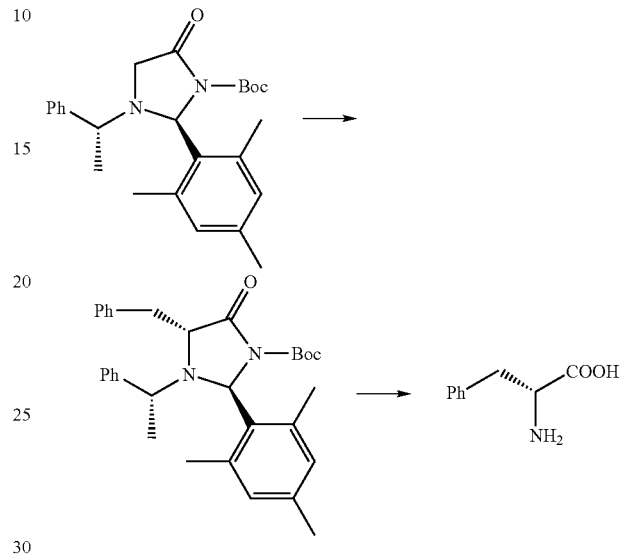

Step 1: Under nitrogen stream, n-butyllithium (16.1 ml, 1.6 mol/L; n-hexane solution, 25.7 mmol) was added dropwise at –20° C. over 10 minutes to an anhydrous tetrahydrofuran solution (30 ml) containing a very small amount of 1,10-phenanthroline (5 mg or less) and of diisopropylamine (4.1 ml, 29.4 mmol). After 20 minutes, an anhydrous tetrahydrofuran solution (20 ml) containing 1,1-dimethylethyl-(2S)-(2,4,6-trimethylphenyl)-5-oxo-3-((1'R)-phenylethyl)tetrahydro-1H-1-imidazolecarboxylate (10 g, 24.5 mmol) obtained by the method in Example 21 was added dropwise thereto over 10 minutes. After an equipment used for the dropwise addition was washed with 2 ml of anhydrous tetrahydrofuran, aging was carried out at –20° C. for 20 minutes. To the mixture was added dropwise benzyl bromide (5.0 g, 29.4 mmol); and the mixture was stirred at –20° C. for 1 hour and thereafter at 0° C. for 18 hours. The reaction mixture was diluted with ethyl acetate (300 ml), and then was washed with an aqueous solution of ammonium chloride, distilled water and saturated brine respectively twice. To the obtained organic layer was added anhydrous magnesium sulfate for drying. After the solid product was separated by filtration, the solvent was removed by distillation in reduced pressure to obtain 12.6 g of a crude product. The crude product was led to the next step without further purification.

Step 2: After 125 ml of tetrahydrofuran and 25 ml of 2M hydrochloric acid were added to the crude product (12.5 g) of Step 1, the pressure of the reaction vessel was reduced and the atmosphere was replaced with nitrogen. To the mixture was added 20% palladium hydroxide-carbon (1.25 g, 50% wet); and the atmosphere of the reaction vessel was replaced with hydrogen gas; and reaction was carried out at 50° C. for 48 hours. The catalyst was separated by filtration, and the cake was washed with 100 ml of tetrahydrofuran and 10 ml of distilled water. Thereafter, the organic solvent was removed in reduced pressure. To the residue was added 10 ml of concentrated hydrochloric acid; and refluxing was carried out for 3.5 hours. After 50 ml of distilled water was added thereto, the resulting reaction mixture was heated to 50° C., and washed with toluene (50 ml×4 times). The organic solvent was removed in reduced pressure, and the pH was adjusted to 2.5 with a 30% aqueous solution of sodium hydroxide. The quantity of phenylalanine in the solution was determined by high performance liquid chromatography as same as in Example 12; and as a result, 3.5 g of (R)-phenylalanine having an optical purity of 100% ee was obtained (total yield: 87%).

Example 23

Phenylmethyl-(2R)-(2,6-dichlorophenyl)-5-oxo-3-((1R')-phenylethyl)tetrahydro-1H-1-imidazolecarboxylate

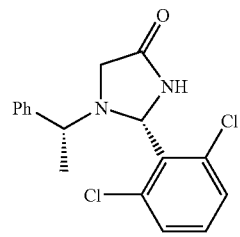

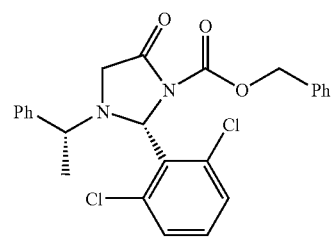

Under nitrogen stream, triethylamine (4.4 g, 43.5 mol) and 4-dimethylaminopyridine (180 mg, 1.5 mmol) were added at room temperature to 25 ml of an ethyl acetate solution containing (2R)-(2,6-dichlorophenyl)-1-((1'R)-phenylethyl)tetrahydro-1H-4-imidazolone (5 g, 14.9 mmol) obtained in Example 8; and the mixture was cooled to 0° C. To the mixture was added dropwise benzyl chloroformate (6.0 g, 35.2 mmol) over 15 minutes; and thereafter, the mixture was stirred for 1 hour. The reaction mixture was diluted with 50 ml of ethyl acetate, and then washed with water and saturated brine. After the organic layer was dried over anhydrous magnesium sulfate, the solvent was removed in reduced pressure to obtain 4.9 g of the title compound as a colorless oily material (yield: 70%).

$^1$H-NMR (400 MHz, CDCl$_3$): δ7.32-7.12 (13H, m), 6.48 (1H, d, J=1.0 Hz), 5.16 (1H, d, J=12.0 Hz), 5.02 (1H, d, J=12.0 Hz), 3.86 (1H, q, J=6.8 Hz), 3.75 (1H, dd, J=1.7 Hz, 16.4 Hz), 3.48 (1H, d, J=16.4 Hz), 1.26 (3H, d, J=6.8 Hz)

Example 24

2-Propenyl-(2R)-(2,6-dichlorophenyl)-5-oxo-3-((1R')-phenylethyl)tetrahydro-1H-1-imidazolecarboxylate

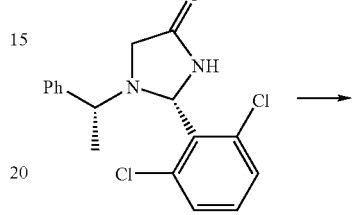

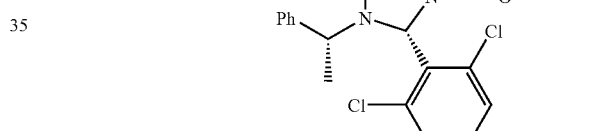
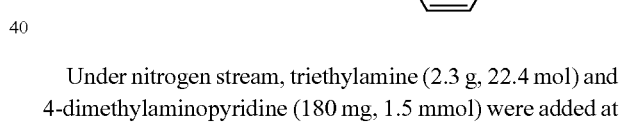

Under nitrogen stream, triethylamine (2.3 g, 22.4 mol) and 4-dimethylaminopyridine (180 mg, 1.5 mmol) were added at 0° C. to 50 ml of an ethyl acetate solution containing (2R)-(2,6-dichlorophenyl)-1-((1'R)-phenylethyl)tetrahydro-1H-4-imidazolone (5 g, 14.9 mmol) obtained in Example 8. An ethyl acetate solution (10 ml) of allyl chloroformate (2.2 g, 17.9 mmol) was added dropwise thereto over 35 minutes; and thereafter, the mixture was stirred for 1 hour. Further, after triethylamine (1.5 g, 14.9 mmol) was added dropwise thereto, an ethyl acetate solution (15 ml) of allyl chloroformate (2.2 g, 17.9 mmol) was added dropwise over 25 minutes; and the mixture was stirred for 1 hour and thereafter at room temperature for 18 hours. The reaction mixture was diluted with 50 ml of ethyl acetate, and washed with an aqueous solution of ammonium chloride, water and saturated brine. After the organic layer was dried over anhydrous magnesium sulfate, the solvent was removed in reduced pressure to obtain 7.2 g of the title compound as a colorless oily material (content from NMR: 65%, 4.7 g, yield: 75%).

$^1$H-NMR (400 MHz, CDCl$_3$): δ7.33-7.16 (8H, m), 6.51 (1H, d, J=1.0 Hz), 5.74 (1H, m), 5.21 (1H, dq, J=1.5 Hz, 17.3 Hz), 5.14 (1H, dq, J=1.2 Hz, 10.5 Hz), 4.57 (2H, m), 3.88 (1H, q, J=6.8 Hz), 3.76 (1H, dd, J=1.7 Hz, 16.4 Hz), 3.50 (1H, dd, J=0.7 Hz, 16.4 Hz), 1.28 (3H, d, J=6.8 Hz)

Example 25

2-Propenyl (2R)-(2,6-dichlorophenyl)-5-oxo-3-((1R')-phenylethyl)-(4S)-(phenylmethyl)tetrahydro-1H-1-imidazolecarboxylate

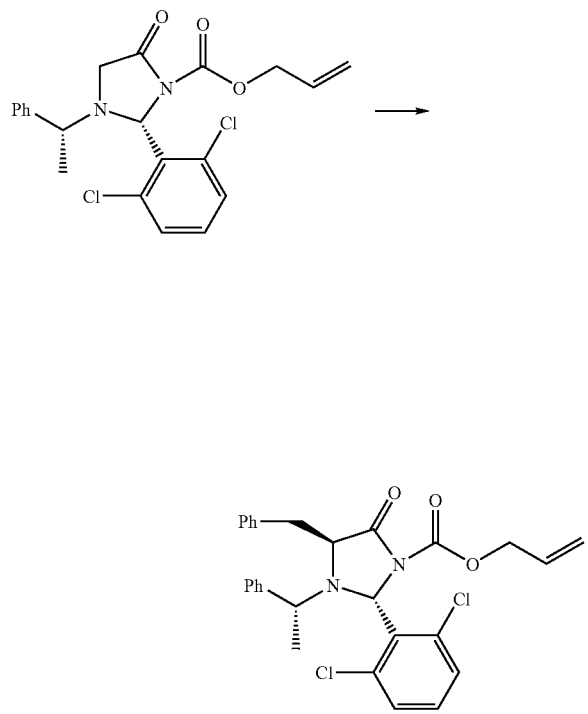

Under nitrogen stream, sodium hexamethyldisilazide (1.9 M tetrahydrofuran solution: 6.7 ml, 12.6 mmol) was added dropwise at −35° C. over about 15 minutes to an anhydrous tetrahydrofuran solution (20 ml) containing a very small amount of 1,10-phenanthroline (5 mg or less), 2-propenyl-(2R)-(2,6-dichloro-phenyl)-5-oxo-3-((1'R)-phenylethyl)tetrahydro-1H-1-imidazole-carboxylate (4.6 g, 11 mmol) obtained in Example 24 and benzyl bromide (2.2 g, 12.6 mmol). The reaction mixture was stirred at −35° C. for 3 hours; and then, was diluted with 50 ml of ethyl acetate and successively washed with a 1M hydrochloric acid, distilled water and saturated brine. After the organic layer was dried over anhydrous magnesium sulfate, the solvent was removed in reduced pressure to obtain a crude product. The crude product was purified by silica gel column chromatography (silica gel 60, 300 g, eluent: hexane/ethyl acetate=3/1 by volume ratio) to obtain 6.0 g of a colorless oily material containing the title compound.

$^1$H-NMR (400 MHz, CDCl$_3$): δ7.32-6.98 (13H, m), 6.25 (1H, d, J=2.0 Hz), 5.67 (1H, m), 5.13 (2H, m), 4.48 (2H, m), 4.31 (1H, t, J=2.9 Hz), 4.00 (1H, q, J=6.6 Hz), 3.31 (1H, dd, J=2.7 Hz, 14.2 Hz), 3.09 (1H, dd, J=6.1 Hz, 14.2 Hz), 1.33 (3H, d, J=6.6 Hz)

Example 26

(2S)-2-Amino-3,3-diphenylpropionic acid

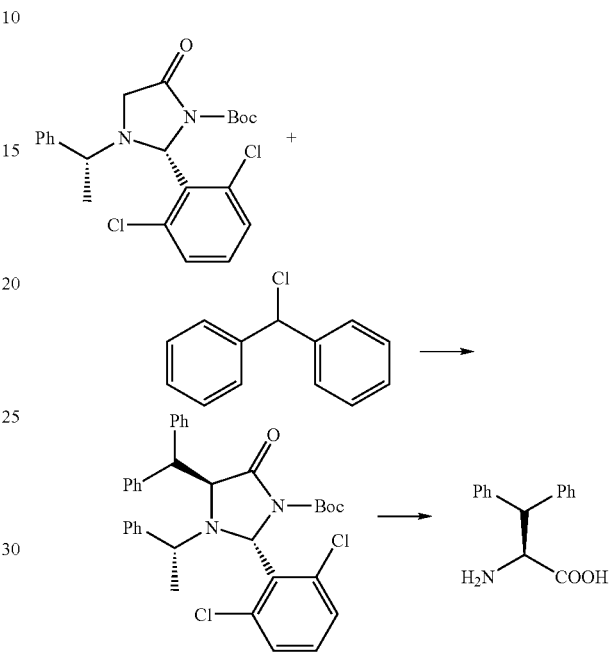

Step 1: Under nitrogen stream, sodium disilazide (1.9 mol/L; tetrahydrofuran solution, 10.6 mmol) was added dropwise at −20° C. over 20 minutes to an anhydrous tetrahydrofuran solution (25 ml) containing a very small amount of 1,10-phenanthroline (5 mg or less), 1-dimethylethyl-(2R)-(2,6-dichlorophenyl)-5-oxo-3-((1'R)-phenylethyl)tetrahydro-1H-1-imidazolecarboxylate (4.0 g, 9.2 mmol) obtained in Example 10 and benzhydryl chloride (3.1 g, 15.3 mmol); and then, reaction was carried out at −20° C. for 15 hours and further at −10° C. for 1 hour and at 0° C. for 4 hours. To the reaction mixture, 6.5 ml of a 4 M acetic acid/tetrahydrofuran solution was added to stop the reaction. The reaction mixture was diluted with 100 ml of ethyl acetate, and then successively washed with distilled water and saturated brine. After the organic layer was dried over anhydrous magnesium sulfate, the solvent was removed in reduced pressure to obtain 7.0 g of a crude product. The crude product was purified by silica gel column chromatography (silica gel 60, 200 g, eluent: hexane/ethyl acetate=5/1 by volume ratio) twice and further purified once in the same manner except that 300 g of silica gel was used to obtain 1,1-dimethylethyl-(2R)-(2,6-dichlorophenyl)-(4S)-(diphenylmethyl)-5-oxo-3-((1'R)-phenylethyl)tetrahydro-1H-1-imidazolecarboxylate in total amount of 1.63 g as a white solid (yield: 30%).

$^1$H-NMR (400 MHz, CDCl$_3$): δ7.50-7.05 (18H, m), 6.25 (1H, d, J=2.2 Hz), 4.67 (1H, dd, J=1.5 Hz, 2.0 Hz), 4.62 (1H, d, J=1.5 Hz), 4.06 (1H, q, J=6.8 Hz), 1.29 (3H, d, J=6.8 Hz), 1.16 (9H, s)

Step 2: After 1,1-dimethylethyl-(2R)-(2,6-dichlorophenyl)-(4S)-(diphenylmethyl)-5-oxo-3-((1'R)-phenylethyl)tetrahydro-1H -1-imidazolecarboxylate (188 mg, 0.31 mmol) was dissolved in a mixed solvent of 7.5 ml of tetrahydrofuran and 1 ml of a 1M hydrochloric acid, the atmosphere of the reaction vessel was replaced with nitrogen. To the mixture was added 90 mg of 20% palladium hydroxide-carbon; and the atmosphere was replaced with nitrogen gas again, and then the atmosphere was replaced with hydrogen gas. After reaction was carried out at room temperature under 2.2 MPa of hydrogen pressure for 100 hours, the catalyst was separated by filtration. The resulting product was washed with 5 ml of tetrahydrofuran three time and 1 ml of distilled water once respectively, and the solvent was removed in reduced pressure. To the mixture was added 7.5 ml of a 6 M hydrochloric acid; and the mixture was heated and refluxed at an outer temperature of 120 to 130° C. for 2.5 hours. Thereafter, the reaction mixture was cooled to an outer temperature of 0° C. After the pH was adjusted to 6 to 7 by adding a 30% aqueous solution of sodium hydroxide thereto, the solvent was removed in reduced pressure. The quantity of (2S)-2-amino-3,3-diphenylpropionic acid contained in the residue was determined in the following analysis condition; and as a result, the yield was 76% at 95.7% ee.

Reference Example 1

Synthesis of 2-amino-3,3-diphenyl propionic acid

Reaction was carried out in a similar manner to Example 26, except that 2.5 g of N-Boc-glycine methyl ester was used in place of 1-dimethylethyl-(2R)-(2,6-dichlorophenyl)-5-oxo-3-((1'R)-phenylethyl)tetrahydro-1H-1-imidazolecarboxylate to obtain 640 mg of 2-(N-Boc-amino)-3,3-diphenylpropionic acid methyl ester as a colorless oily material (yield: 14%). Further, 354 mg of 2-(N-Boc-amino)-3,3-diphenylpropionic acid methyl ester was mixed with a 6 M solution of aqueous hydrochloric acid, and the mixture was refluxed for 5 hours. Thereafter, the mixture was washed with toluene, and neutralized with a 30% aqueous solution of sodium hydroxide to obtain a white solid of 2-amino-3,3-diphenylpropionic acid. The retention time of the respective isomers was confirmed by using the product.

Optical Purity Analysis Condition
Column: Chiral Pack WH (inner diameter: 4.6 mm×25 cm) manufactured by Daicel Chemical Industries, Ltd.
Mobile phase: 2 mM aqueous solution of copper sulfate/methanol=90/10 by volume ratio
Flow rate: 1.0 ml/min
Detector: UV 250 nm
Retention time: (2R) isomer—about 16 minutes
(2S) isomer—about 29 minutes Example 27

(2S,3R)-2-Amino-3-hydroxy-5-phenylpentanoic acid

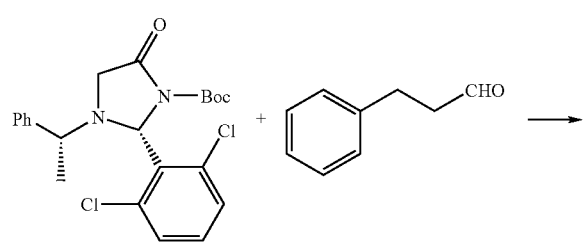

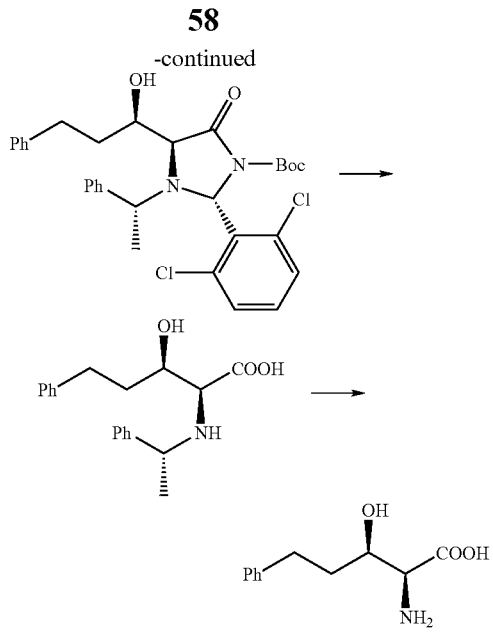

Step 1: Under nitrogen stream, n-butyllithium (5.0 ml, 1.6 mol/L; n-hexane solution, 7.9 mmol) was added dropwise at −0° C. over 5 minutes to an anhydrous tetrahydrofuran solution (10 ml) containing a very small amount of 1,10-phenanthroline (5 mg or less) and diisopropylamine (1.2 ml, 8.6 mmol). The mixture was stirred at 0° C. for 5 minutes, and then was cooled to −78° C. and stirred for 10 minutes. An anhydrous tetrahydrofuran solution (6 ml) containing 1,1-dimethylethyl-(2R)-(2,6-dichlorophenyl)-5-oxo-3-((1'R)-phenylethyl)tetrahydro-1H-1-imidazolecarboxylate (3.0 g, 6.9 mmol) obtained in Example 10 was added dropwise thereto over 10 minutes. After an equipment used for the dropwise addition was washed with 2 ml of anhydrous tetrahydrofuran, aging was carried out at −78° C. for 20 minutes. To the mixture was added dropwise 3-phenylpropionaldehyde (0.93 g, 6.93 mmol) over 10 minutes. After reaction was carried out at −78° C. for 3 hours, 4 ml of a 4 M acetic acid/tetrahydrofuran solution was added to stop the reaction. The mixture was diluted with 100 ml of ethyl acetate, and then was successively washed with an aqueous solution of ammonium chloride, water and saturated brine. After the obtained organic layer was dried over anhydrous magnesium sulfate, the solvent was removed by distillation in reduced pressure to obtain a crude product. The crude product was purified by silica gel column chromatography (silica gel 60, 400 g, eluent: hexane/ethyl acetate=3/1 by volume ratio) to obtain 1,1-dimethylethyl (2R)-(2,6-dichlorophenyl)-(4S)-((1R)-hydroxy-3-phenylpropyl)-5-oxo-3-((1'R)-phenylethyl) tetrahydro-1H-1-imidazolecarboxylate and 1,1-dimethylethyl (2R)-(2,6-dichlorophenyl)-(4S)-((1S)-hydroxy-3-phenylpropyl)-5-oxo-3-((1'R)-phenylethyl) tetrahydro-1H-1-imidazolecarboxylate as a colorless oily material in total amount of 3.5 g (substantial yield: 90%).

The production ratio with respect to the newly formed hydroxyl groups was determined to be R:S=84:16 according to NMR of the crude product.

Step 2: A 6 M hydrochloric acid (9.6 ml) was mixed with 1,1-dimethylethyl (2R)-(2,6-dichlorophenyl)-(4S)-((1R)-hydroxy-3-phenylpropyl)-5-oxo-3-((1'R)-phenylethyl)tetrahydro-1H-1-imidazolecarboxylate (477.5 mg, HPLC: 91.5 area %, 434 mg, 0.767 mmol), and the mixture was refluxed at an outer temperature of 120 to 130° C. for 4 hours. The mixture was cooled to 50° C., and then was washed with 20 ml of toluene twice and 10 ml once. Subsequently, the mixture was cooled to outer temperature of 0° C., and the pH was adjusted to 6 to 7 by adding a 30% aqueous solution of sodium hydroxide and a 1 M hydrochloric acid. To the mixture was added 20 ml of ethyl acetate; and the mixture was stirred at 0° C. for 1 hour. The precipitated crystal was filtered; and successively washed with 5 ml of ethyl acetate, 10 ml of ice-cooled water and ml of hexane. The obtained crystal was dried in vacuum at 40° C. to obtain 195 mg of (3R)-hydroxy-5-phenyl-(2S)-[((1'R)-phenylethyl)amino]pentanoic acid as a white solid (yield: 81%).

$^1$H-NMR (400 MHz, CD$_3$OD): δ7.51-7.36 (5H, m), 7.25-7.11 (5H, m), 4.42 (1H, q, J=6.8 Hz), 3.89 (1H, m), 3.41 (1H, d, J=6.3 Hz), 2.84 (1H, m), 2.61 (1H, m), 1.92 (1H, m), 1.80 (1H, m), 1.67 (3H, d, J=6.8 Hz)

Step 3: After (3R)-hydroxy-5-phenyl-(2S)-[((1'R)— phenylethyl)amino]pentanoic acid (150 mg, 0.48 mmol) was dissolved in a mixed solvent of tetrahydrofuran (10 ml) and a 1 M hydrochloric acid (1.4 ml), the pressure of the reaction vessel was reduced and the atmosphere was replaced with nitrogen. After 20% palladium-carbon (75 mg, 50% wet) was added thereto, the atmosphere was further replaced with nitrogen and then was replaced with hydrogen gas. Reaction was carried out at room temperature under 2.2 MPa of hydrogen pressure for 50 hours. After the catalyst was separated by filtration and washed with 5 ml of tetrahydrofuran three time and 1 ml of distilled water once, the solvent was removed in reduced pressure. Further, the residue was dried in vacuum at 40° C. to obtain 115 mg (yield: 98%, 100% ee) of (2S,3R)-2-amino-3-hydroxy-5-phenylpentanoiciacid hydrochloride as a white solid.

$^1$H-NMR (400 MHz, D$_2$O+DCl): δ7.21-7.07 (5H, m), 3.99 (1H, m), 3.81 (1H, d, J=3.9 Hz), 2.72-2.65 (1H, m), 2.58-2.51 (1H, m), 1.82-1.66 (2H, m)

Optical Purity Analysis Condition

Column: Chiral Pack WH (inner diameter 4.6 mm×25 cm) manufactured by Daicel Chemical Industries, Ltd.

Mobile phase: 2 mM aqueous solution of copper sulfate/methanol=90/10 by volume ratio Flow rate: 0.5 ml/min Detector: UV 254 nm Retention time: (2R,3R) isomer and (2R,3S) isomer— about 14 minutes (2S,3R) isomer—about 27 minutes (2S,3S) isomer—about 42 minutes Example 28

(2R,3S)-2-Amino-3-hydroxy-5-phenylpentanoic acid

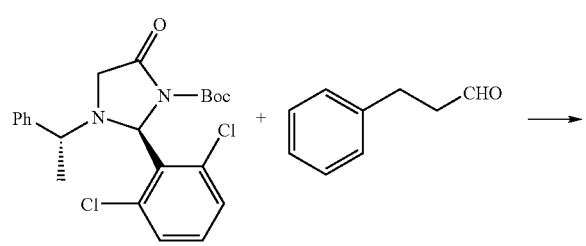

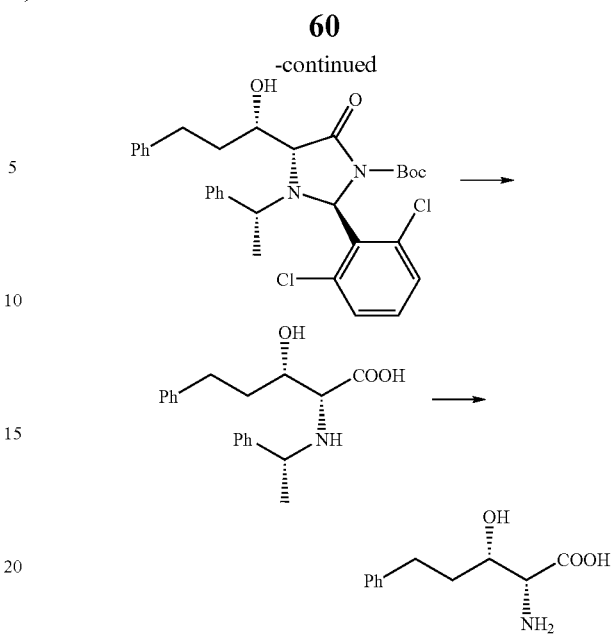

Step 1: Under nitrogen stream, n-butyllithium (4.7 ml, 1.6 mol/L; n-hexane solution, 7.5 mmol) was added dropwise at −0° C. over 8 minutes to an anhydrous tetrahydrofuran solution (10 ml) containing a very small amount of 1,10-phenanthroline (5 mg or less) and diisopropylamine (1.2 ml, 8.6 mmol). The mixture was stirred at 0° C. for 10 minutes; and then, was cooled to −78° C. and stirred for 20 minutes. An anhydrous tetrahydrofuran solution (6 ml) containing 1-dimethylethyl-(2S)-(2,6-dichlorophenyl)-5-oxo-3-((1'R)-phenylethyl)tetrahydro-1H-1-imidazolecarboxylate (3.0 g, 6.9 mmol) obtained in Example 11 was added dropwise over 10 minutes. After an equipment used for the dropwise addition was washed with 2 ml of anhydrous tetrahydrofuran, aging was carried out at −78° C. for 20 minutes. To the mixture was added dropwise 3-phenyl-propionaldehyde (0.92 g, 6.9 mmol) over 10 minutes. After reaction was carried out at −78° C. for 2 hours, 15 ml of a 1 M acetic acid/tetrahydrofuran solution was added to stop the reaction. The mixture was diluted with 100 ml of ethyl acetate; and then, was washed with an aqueous solution of ammonium chloride, water and saturated brine in this order. After the organic layer was dried over anhydrous magnesium sulfate, the solvent was removed by distillation in reduced pressure to obtain a crude product. The production ratio with respect to the newly formed hydroxyl groups was determined to be S:R=83:17 according to $^1$H-NMR of the crude product. The crude product was crystallized from 5 ml of ethyl acetate and 45 ml of hexane to obtain 2.3 g of 1,1-dimethylethyl (2S)-(2,6-dichlorophenyl)-(4R)-((1S)-hydroxy-3-phenylpropyl)-5-oxo-3-((1'R)-phenylethyl)tetrahydro-1H-1-imidazolecarboxylate as a yellow crystal (yield: 59%). No peak corresponding to the other diastereomers was observed in the NMR data.

$^1$H-NMR (400 MHz, CDCl$_3$): δ7.36-7.32 (4H, m), 7.27-7.18 (7H, m), 6.89-6.87 (2H, m), 6.77 (1H, d, J=3.4 Hz), 3.84-3.78 (2H, m), 3.43 (1H, d, J=9.8 Hz), 3.02-2.95 (1H, m), 2.70-2.63 (1H, m), 2.10-2.02 (1H, m), 1.65-1.55 (1H, m), 1.26-1.24 (12H, m)

Step 2: Mixed were 1,1-dimethylethyl (2S)-(2,6-dichloro phenyl)-(4R)-((1S)-hydroxy-3-phenylpropyl)-5-oxo-3-((1'R)-phenylethyl)tetrahydro-1H-1-imidazolecarboxylate (500 mg, purity 92.2 wt %, content 461 mg, 0.81 mmol) and 7.5 ml of a 6 M hydrochloric acid; and the mixture was refluxed at an outer temperature of 120 to 130° C. for 4 hours.

The mixture was cooled at an outer temperature of 50° C.; and then, was washed with respectively 10 ml of toluene three times. The mixture was cooled at an outer temperature of 0° C.; and then, the pH was adjusted to 7.2 by adding a 30% aqueous solution of sodium hydroxide. To the mixture was added 15 ml of ethyl acetate; and aging was carried out at 0° C. for 1 hour. The precipitated crystal was separated by filtration, and successively washed with 15 ml of ethyl acetate, 5 ml of distilled water and 10 ml of hexane. The crystal was dried in vacuum at 40° C. to obtain 182 mg of (3S)-hydroxy-5-phenyl-(2R)-[((1'R)-phenylethyl)amino]pentanoic acid as a white solid (yield: 72%).

$^{1}$H-NMR (400 MHz, CD$_{3}$OD): δ7.48-7.38 (5H, m), 7.22-7.18(2H, m), 7.12-7.09 (3H, m), 4.38 (1H, q, J=6.8 Hz), 3.80 (1H, m), 3.06 (1H, d, J=6.4 Hz), 2.69 (1H, m), 2.43 (1H, m), 1.80-1.63 (2H, m), 1.71 (3H, d, J=6.8 Hz)

Step 3: After (3S)-hydroxy-5-phenyl-(2R)-[((1'R)-phenylethyl)amino]pentanoic acid (100 mg, 0.32 mmol) was dissolved in a mixed solvent of tetrahydrofuran (10 ml) and a 1 M hydrochloric acid (0.6 ml), the atmosphere was replaced with nitrogen. After 59 mg of 20% palladium-carbon was added thereto and the atmosphere was replaced with nitrogen again, the atmosphere was replaced with hydrogen gas and the mixture was stirred at room temperature under 2.2 MPa of hydrogen pressure for 70 hours. The catalyst was separated by filtration and washed with respectively 5 ml of tetrahydrofuran three time and 1 ml of distilled water once; and then, the solvent was removed in reduced pressure. Further, the residue was dried in vacuum at 40° C. to quantitatively obtain (2R,3S)-2-amino-3-hydroxy-5-phenylpentanoic acid as a white solid (80 mg, 100% ee). The optical purity analysis was carried out in the same conditions as those of Example 27. As a result, (2S,3S) isomer was not obserbed.

$^{1}$H-NMR (400 MHz, D$_{2}$O+DCl): δ7.24-7.10 (5H, m), 4.00 (1H, m), 3.82 (1H, d, J=3.4 Hz), 2.75-2.68 (1H, m), 2.60-2.53 (1H, m), 1.81-1.71 (2H, m)

Reference Example 2

Synthesis of mixture of 2-amino-3-hydroxy-5-phenylpentanoic acid isomers

Reaction was carried out in the same manner as in Example 27, except that 2.5 g of N-Boc-glycine methyl ester was used in place of 1-dimethylethyl-(2R)-(2,6-dichlorophenyl)-5-oxo-3-((1'R)-phenylethyl)tetrahydro-1H-1-imidazolecarboxylate to obtain 3.3 g of 2-(N-Boc-amino)-3-hydroxy-5-phenylpentanoic acid methyl ester as a white solid (yield: 78%). Further, 11.0 g of 2-(N-Boc-amino)-3-hydroxy-5-phenylpentanoic acid methyl ester was mixed with a 6 M hydrochloric acid, and the mixture was refluxed for 4 hours. Thereafter, the solvent was removed in reduced pressure to obtain 2-amino-3-hydroxy-5-phenylpentanoic acid hydrochloride. The retention time of the respective isomers was confirmed using the product. Further, the pH of the aqueous solution of the hydrochloride salt was adjusted to 6 to 7 by a 30% aqueous solution of sodium hydroxide to obtain 346 mg of 2-amino-3-hydroxy-5-phenylpentanoic acid as a white solid (yield: 53%).

Example 29

(2R,3S)-2-Amino-3-hydroxy-5-phenylpentanoic acid

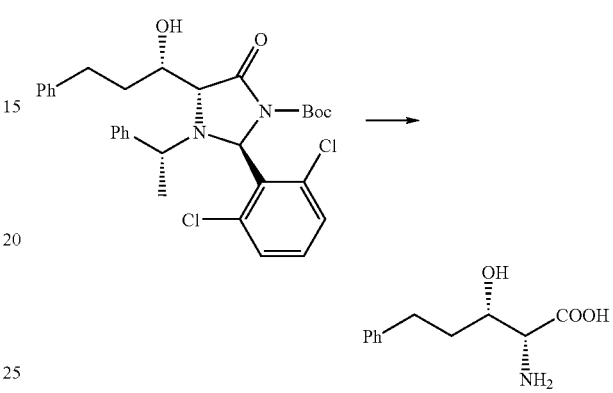

After 1,1-dimethylethyl (2S)-(2,6-dichlorophenyl)-(4R)-((1S)-hydroxy-3-phenylpropyl)-5-oxo-3-((1'R)-phenylethyl)tetra hydro-1H-1-imidazolecarboxylate (200 mg, 0.35 mmol) obtained in the Step 1 of Example 28 was dissolved in tetrahydrofuran (7.5 ml) and a 1 M aqueous solution of hydrogen chloride (1 ml), the atmosphere was replaced with nitrogen. After palladium hydroxide-carbon (100 mg) was added thereto and the atmosphere was replaced with nitrogen again, the atmosphere was replaced with hydrogen gas. After reaction was carried out at a reaction temperature of 40° C. under a hydrogen pressure of 2.2 MPa for 42 hours, the catalyst was separated by filtration and the residue was washed with tetrahydrofuran (10 ml×2). The solvent was removed in reduced pressure to obtain 104 mg of a crude product. An aqueous 6 M hydrochloric acid solution (4 ml) was added to the crude product, and reaction was carried out at an outer temperature of 120 to 130° C. for 4 hours. Subsequently, the solvent was removed in reduced pressure; and as a result, 109 mg of (2R,3S)-2-amino-3-hydroxy-5-phenylpentanoic acid hydrochloride as a crude product was obtained. Analysis was carried out in the same conditions as those in Example 27; as a result, the purity was determined to be 99.3% ee.

Example 30

(2S,3R)-2-Amino-3-hydroxy-4-phenylbutanoic acid

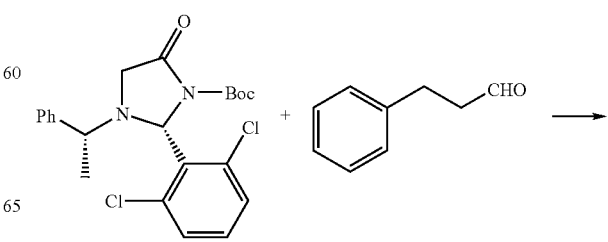

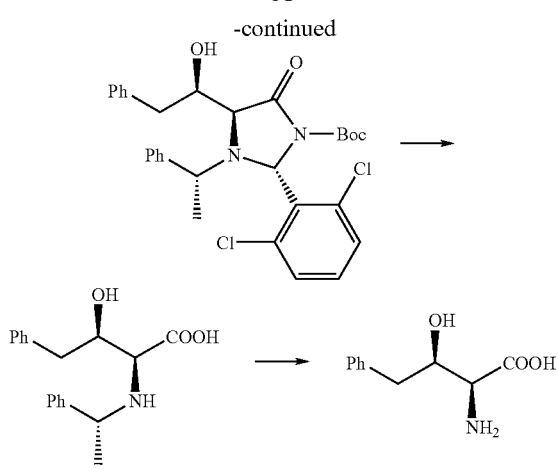

Step 1: Under nitrogen stream, n-butyllithium (5.0 ml, 1.6 mol/L; n-hexane solution) was added dropwise at −0° C. over 10 minutes to an anhydrous tetrahydrofuran solution (10 ml) containing a very small amount of 1,10-phenanthroline (5 mg or less) and diisopropylamine (1.2 ml, 8.6 mmol). After aging was carried out at 0° C. and −78° C. for respectively 10 minutes, an anhydrous tetrahydrofuran solution (6 ml) containing 1-dimethylethyl-(2R)-(2,6-dichlorophenyl)-5-oxo-3-((1'R)-phenylethyl)tetrahydro-1H-1-imidazolecarboxylate (3.0 g, 6.9 mmol) obtained by the method of Example 10 was added dropwise over 10 minutes to the mixture. After an equipment used for the dropwise addition was washed with 2 ml of anhydrous tetrahydrofuran, aging was carried out at −78° C. for 25 minutes. To the mixture was added dropwise phenylacetaldehyde (1.0 g, 8.6 mmol) over 5 minutes. After reaction was carried out at −78° C. for 3 hours, 4.2 ml of a 4M acetic acid/tetrahydrofuran solution was added to stop the reaction. The mixture was diluted with 100 ml of ethyl acetate, and then was washed with water and saturated brine in this order. After the organic layer was dried over anhydrous magnesium sulfate, the solvent was removed by distillation in reduced pressure to obtain 4.4 g of a crude product. The production ratio with respect to the newly formed hydroxyl groups was determined to be R:S=86:14 according to $^1$H-NMR of the crude product. The crude product was purified by silica gel column chromatography (silica gel 60, 350 g, eluent: hexane/ethyl acetate=3/1 by volume ratio) to obtain 2.6 g of 1,1-dimethylethyl-(2R)-(2,6-dichlorophenyl)-4-((1R)-hydroxy-2-phenylethyl)-5-oxo-3-((1'R)-phenylethyl)tetrahydro-1H-1-imidazolecarboxylate as a colorless oily material (substantial yield: 68%). Further, a portion of the product was purified with a thin-layer silica gel plate (Merk Silica Gel Plate, 200×200×0.25 mm; three sheets; eluent: hexane/ethyl acetate=3/1 by volume) to obtain 50 mg of 1,1-dimethylethyl-(2R)-(2,6-dichlorophenyl)-4-((1S)-hydroxy-2-phenylethyl)-5-oxo-3-((1'R)-phenylethyl)tetrahydro-1H-1-imidazolecarboxylate, and was analyzed by $^1$H-NMR.

1,1-Dimethylethyl-(2R)-(2,6-dichlorophenyl)-(4S)-((1R)-hydroxy-2-phenylethyl)-5-oxo-3-((1'R)-phenylethyl)tetrahydro-1H-1-imidazolecarboxylate $^1$H-NMR (400 MHz, CDCl$_3$): 7.37-7.01 (13H, m), 6.75 (1H, d, J=2.7 Hz), 4.41 (1H, t, J=3.4 Hz), 4.00 (1H, m), 3.80 (1H, d, J=6.8 Hz), 3.46 (1H, d, J=11.5 Hz), 3.23 (1H, dd, J=2.4 Hz, 13.7 Hz), 2.60 (1H, dd, J=10.5 Hz, 13.7 Hz), 1.36 (3H, d, J=7.1 Hz), 1.27 (9H, s)

1,1-Dimethylethyl-(2R)-(2,6-dichlorophenyl)-(4S)-((1S)-hydroxy-2-phenylethyl)-5-oxo-3-((1'R)-phenylethyl)tetrahydro-1H-1-imidazolecarboxylate $^1$H-NMR (400 MHz, CDCl$_3$): 7.29-6.97 (13H, m), 6.33 (1H, s), 4.38 (1H, brs), 4.27 (1H, q, J=7.1 Hz), 3.49 (2H, brs), 3.36 (1H, dd, J=6.1 Hz, 13.7 Hz), 3.19 (1H, dd, J=8.5 Hz, 13.4 Hz), 1.49 (3H, d, J=7.1 Hz), 1.21 (9H, s)

Step 2: Mixed were 1,1-dimethylethyl-(2R)-(2,6-dichlorophenyl)-(4S)-((1R)-hydroxy-3-phenylethyl)-5-oxo-3-((1'R)-phenylethyl)tetrahydro-1H-1-imidazolecarboxylate (1.3 g, content: 85.3%; 1.1 g, 1.98 mmol) and 12.9 ml of a 6M aqueous solution of hydrogen chloride, the mixture was refluxed at an outer temperature of 120 to 130° C. for 4.5 hours. The mixture was cooled to an outer temperature of 80° C.; and then, was washed with respectively 20 ml of toluene three times, and cooled to an outer temperature of 0° C. After the pH was adjusted to 6 to 7 by adding a 30% aqueous solution of sodium hydroxide thereto, aging was carried out at 0° C. for 2 hours. The precipitated crystal was separated by filtration, and successively washed with 5 ml of ice-cooled water and 5 ml of ethyl acetate. Then, the obtained crystal was dried at 40° C. in vacuum; and as a result, 554 mg of (3R)-hydroxy-4-phenyl-(2S)-[(1'R)-(phenylethyl)amino]butanoic acid was obtained as a white solid (yield: 94%). It was found that the product contains about 6.5% of (3S)-hydroxy-4-phenyl-(2S)-[(1'R)-phenylethyl)amino]butanoic acid which was not separated in Step 1 according to $^1$H-NMR (about 86.9% de).

(3R)-Hydroxy-4-phenyl-(2S)-[(1'R)-phenylethyl)amino]butanoic acid $^1$H-NMR (400 MHz, CD$_3$OD): 7.46-7.37 (5H, m), 7.30-7.18 (5H, m), 4.41 (1H, q, J=6.8 Hz), 4.17 (1H, m), 3.42 (1H, d, J=6.3 Hz), 3.03 (1H, dd, J=3.9 Hz, 14.2 Hz), 2.81 (1H, dd, J=8.8 Hz, 14.2 Hz), 1.68 (3H, d, J=6.8 Hz)

Step 3: After 300 mg of (3R)-hydroxy-4-phenyl-(2S)-[(1'R)-(phenylethyl)amino]butanoic acid was dissolved in a mixed solvent of 10 ml of tetrahydrofuran and 3 ml of a 1 M aqueous solution of hydrogen chloride, the atmosphere was replaced with nitrogen. After 100 mg of 20% palladium-carbon was added thereto and the atmosphere was replaced with nitrogen again, the atmosphere was replaced with hydrogen gas. Reaction was carried out at room temperature under 2.2 MPa of hydrogen pressure for 24 hours. Thereafter, the catalyst was separated by filtration, and washed with respectively 5 ml of tetrahydrofuran three time and 1 ml of distilled water once. The solvent was removed in reduced pressure; and as a result, (2S,3R)-2-amino-3-hydroxy-4-phenylbutanoic acid hydrochloride was quantitatively obtained as a white solid (240 mg). From HPLC analysis, the crystal contained (2R,3R) isomer:(2S,3R) isomer:(2S,3S) isomer at a ratio of 6:88:6.

(2S,3R)-2-Amino-3-hydroxy-4-phenylbutanoic acid hydrochloride $^1$H-NMR (400 MHz, D$_2$O+DCl): δ6.33-6.21 (5H, m), 3.44 (1H, m), 3.08 (1H, m), 1.97 (1H, dd, J=4.2 Hz, 13.4 Hz), 1.82 (1H, dd, J=9.3 Hz, 13.9 Hz)

Optical Purity Analysis Condition
Column: Chiral Pack WH (inner diameter: 4.6 mm×25 cm) manufactured by Daicel Chemical Industries, Ltd.
Mobile phase: 2 mM aqueous solution of copper sulfate/methanol =90/10 by volume ratio
Flow rate: 0.5 ml/min Detector: UV 254 nm
Retention time: (2R,3R) isomer and (2R,3S) isomer—
about 18 minutes
(2S,3R) isomer—about 25 minutes
(2S,3S) isomer—about 33 minutes Reference Example 3

Synthesis of mixture of
2-amino-3-hydroxy-5-phenylbutanoic acid isomers

Reaction was carried out in the same manner as in Example 30, except that 2.5 g of N-Boc-glycine methyl ester was used in place of 1-dimethylethyl-(2R)-(2,6-dichlorophenyl)-5-oxo-3-((1'R)-phenylethyl)tetrahydro-1H-1-imidazolecarboxylate to obtain 3.1 g of 2-(N-Boc-amino)-3-hydroxy-4-phenylbutanoic acid methyl ester as a colorless oily material (yield: 76%). Further, 1.7 g of 2-(N-Boc-amino)-3-hydroxy-5-phenylbutanoic acid methyl ester was mixed with a 6 M solution of aqueous hydrochloric acid. The mixture was refluxed for 4 hours; and thereafter, the mixture was washed with toluene, and neutralized with a 30% aqueous solution of sodium hydroxide to obtain 0.74 g of 2-amino-3-hydroxy-4-phenylbutanoic acid as a white solid (yield: 70%). The retention time of the respective isomers was confirmed using the product.

INDUSTRIAL APPLICABILITY

An optically active imidazolidinone derivative produced by the present invention can be widely used for synthesizing an optically active amino acid; and accordingly, an optically active amino acid that is important in various fields such as pharmaceutical field in terms of production can easily be produced.

The invention claimed is:
1. An imidazolidinone derivative represented by the general formula (1):

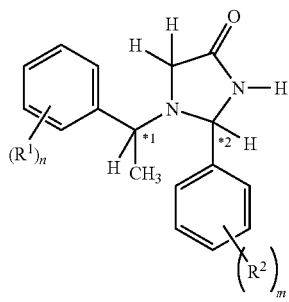

(1)

or an optically active form thereof,
wherein, n and m independently represents an integer of 0 to 5 representively indicating the numbers of substituent groups $R^1$ and $R^2$ on the benzene rings; $R^1$ and $R^2$ independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$ or $R^2$, the plural $R^1$ or $R^2$ may be all the same or different; *1 and *2 indicate asymmetric carbon atoms.

2. An imidazolidinone derivative represented by the general formula (2):

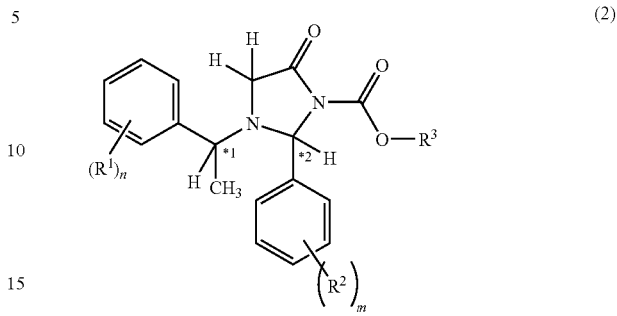

(2)

or an optically active form thereof,
wherein, n and m independently represents an integer of 0 to 5 representively indicating the numbers of substituent groups $R^1$ and $R^2$ on the benzene rings; $R^1$ and $R^2$ independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$ or $R^2$, the plural $R^1$ or $R^2$ may be all the same or different; *1 and *2 indicate asymmetric carbon atoms; $R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms.

3. An optically active imidazolidinone derivative represented by the general formula (3):

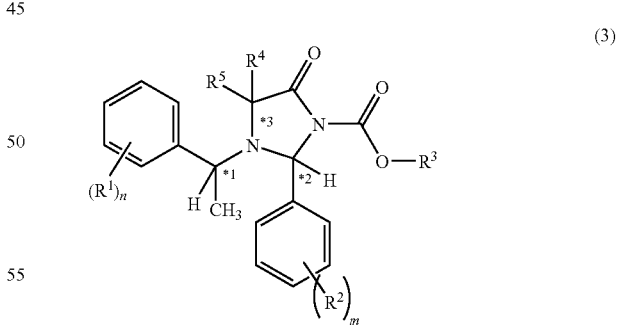

(3)

wherein, n and m independently represents an integer of 0 to 5 representively indicating the numbers of substituent groups $R^1$ and $R^2$ on the benzene rings; $R^1$ and $R^2$ independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R¹ or R², the plural R¹ or R² may be all the same or different; R³ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aryl group having 6 to 18 carbon atoms, or an optionally substituted aralkyl group having 7 to 18 carbon atoms; R⁴ and R⁵ are different, and represent a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and *1, *2 and *3 indicate asymmetric carbon atoms.

4. A method of producing an imidazolidinone derivative comprising a step of condensating an optically active glycinamide derivative represented by the general formula (4):

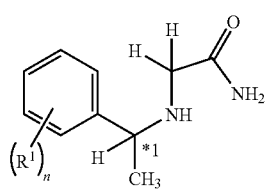

(4)

wherein, n represents an integer of 0 to 5 indicating the number of substituent groups R¹ on the benzene ring; R¹ represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R¹, the plural R¹ may be all the same or different; and *1 indicates an asymmetric carbon atom, with a substituted benzaldehyde represented by the general formula (5):

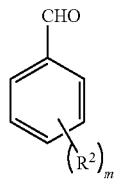

(5)

wherein, m represents an integer of 0 to 5 indicating the number of substituent groups R² on the benzene ring; R² represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; and in case that there are a plurality of R², the plural R² may be all the same or different, in the presence of an acidic catalyst, wherein the imidazolidinone derivative is represented by the general formula (1):

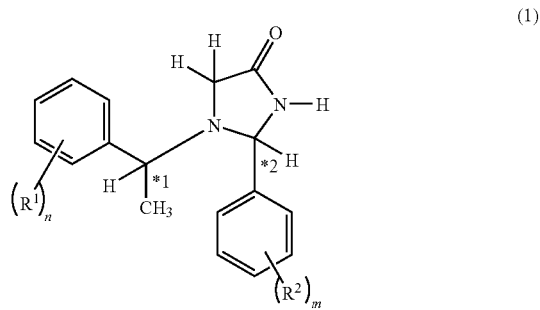

(1)

wherein, n, m, R¹, R² and *1 are the same as described above; and *2 indicates an asymmetric carbon atom.

5. The method of producing an imidazolidinone derivative according to claim 4, wherein the acidic catalyst is sulfonic acids.

6. A method of crystallizing an optically active imidazolidinone derivative, comprising a step of crystallizing the imidazolidinone derivative represented by the general formula (1):

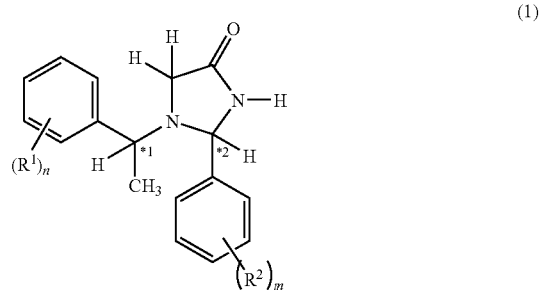

(1)

or an optically active form thereof, wherein, n and m independently represents an integer of 0 to 5 representively indicating the numbers of substituent groups R¹ and R² on the benzene rings; R¹ and R² independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R¹ or R2, the plural R¹ or R² may be all the same or different; *1 and *2 indicate asymmetric carbon atoms, using an organic solvent, wherein the optically active imidazolidinone derivative is crystallized while the imidazolidinone derivative is isomerized.

7. The method of crystallization according to claim 6, wherein an acidic catalyst is used in the isomerization.

8. A method of producing an imidazolidinone derivative represented by the general formula (2):

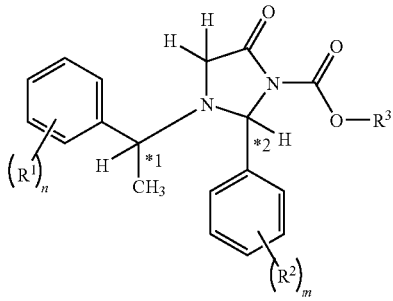

(2)

wherein, n and m independently represents an integer of 0 to 5 representively indicating the numbers of substituent groups $R^1$ and $R^2$ on the benzene rings; $R^1$ and $R^2$ independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$ or $R^2$, the plural $R^1$ or $R^2$ may be all the same or different; *1 and *2 indicate asymmetric carbon atoms; $R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms, comprising a step of reacting an imidazolidinone derivative or an optically active form thereof, represented by the general formula (1):

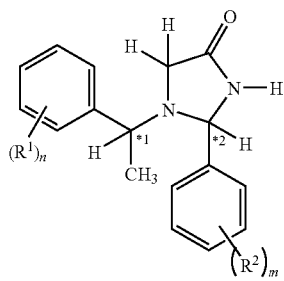

(1)

wherein, n, m, $R^1$, $R^2$, *1 and *2 are the same as described above, with a halogenoformic acid ester represented by the general formula (6):

R³OCOX     (6)

wherein, $R^3$ is the same as described above; and X represents a halogen atom, or a pyrocarbonic acid ester represented by the general formula (7):

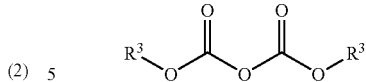

(7)

wherein, $R^3$ is the same as described above and two $R^3$ are the same, in the presence of a base.

9. The production method according to claim 8, further comprising a step of condensating an optically active glycinamide derivative represented by the general formula (4):

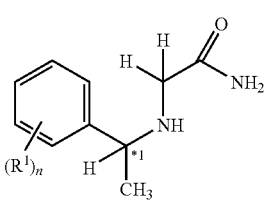

(4)

wherein, n, $R^1$, and *1 are the same as described above, with a substituted benzaldehyde represented by the general formula (5):

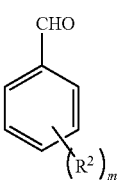

(5)

wherein, m and $R^2$ are the same as described above, in the presence of an acidic catalyst, to obtain the imidazolidinone derivative represented by the general formula (1).

10. A method of producing an optically active imidazolidinone derivative represented by the general formula (3):

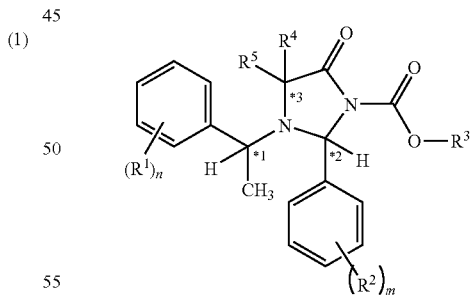

(3)

wherein, n and m independently represents an integer of 0 to 5 representively indicating the numbers of substituent groups $R^1$ and $R^2$ on the benzene rings; $R^1$ and $R^2$ independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$ or $R^2$, the plural $R^1$ or $R^2$ may be all the same or different; $R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aryl group having 6 to 18 carbon atoms, or an optionally substituted aralkyl group having 7 to 18 carbon atoms; $R^4$ and $R^5$ are different and represent a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and *1, *2 and *3 indicate asymmetric carbon atoms; and at least one of $R^4$ and $R^5$ is $R^7$, comprising a step of reacting an optically active imidazolidinone derivative represented by the general formula (2):

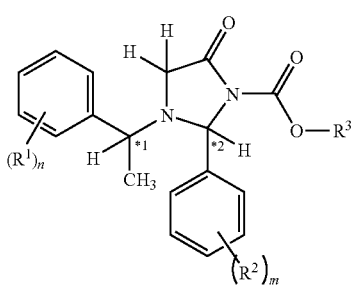

(2)

wherein, n, m, $R^1$, $R^2$, $R^3$, *1 and *2 are the same as described above, with one or two kinds of electrophilic agents represented by the general formula (8):

$$R^7Y \qquad (8)$$

wherein, $R^7$ represents an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and Y represents a leaving group, in the presence of a base.

11. The production method according to claim 10, wherein the compound represented by the general formula (2) is obtained by reacting an imidazolidinone derivative or an optically active form thereof, represented by the general formula (1):

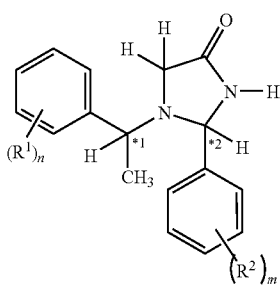

(1)

wherein, n, m, $R^1$, $R^2$, *1 and *2 are the same as described above, with a halogenoformic acid ester represented by the general formula (6):

$$R^3OCOX \qquad (6)$$

wherein, $R^3$ is the same as described above; and X represents a halogen atom, or a pyrocarbonic acid ester represented by the general formula (7):

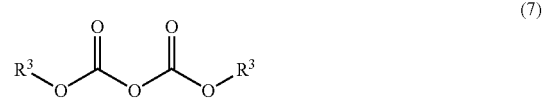

(7)

wherein, $R^3$ is the same as described above and two $R^3$ are the same, in the presence of a base.

12. The method of producing an optically active imidazolidinone derivative according to claim 10, wherein the base to be used is at least one kind of lithium diisopropylamide, lithium hexamethyldisilazide, sodium hexamethyldisilazide, potassium hexamethyldisilazide, t-butyl magnesium chloride, potassium t-butoxide, sodium t-butoxide, lithium t-butoxide, lithium hydride, sodium hydride, potassium hydride and calcium hydride.

13. A method of producing an optically active N-(1-substituted phenylethyl)amino acid derivative represented by the general formula (9):

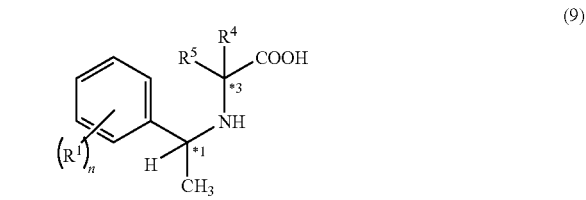

(9)

wherein, n represents an integer of 0 to 5 representively indicating the numbers of substituent groups $R^1$ on the benzene ring; $R^1$ represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$, the plural $R^1$ may be all the same or different; $R^4$ and $R^5$ are different and represent a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and *1 and *3 indicate asymmetric carbon atoms, comprising a step of treating an optically active imidazolidinone derivative represented by the general formula (3):

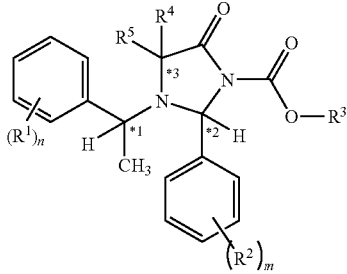
(3)

wherein, n, $R^1$, $R^4$, $R^5$, *1 and *3 are the same as described above; m represents an integer of 0 to 5 representively indicating the numbers of substituent groups $R^2$ on the benzene ring; $R^2$ represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^2$, the plural $R^2$ may be all the same or different; $R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aryl group having 6 to 18 carbon atoms, or an optionally substituted aralkyl group having 7 to 18 carbon atoms; and *2 indicates an asymmetric carbon atom, with an acid or a base in a solvent containing at least one kind of organic solvents and water.

14. A method of producing an optically active amino acid represented by the general formula (10):

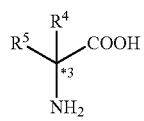
(10)

wherein, $R^4$, $R^5$ and *3 are the same as described above,
comprising a step of removing the protective substituent group on the nitrogen of the amino acid derivative represented by the general formula (9) and obtained by the method according to claim 13.

15. A method of producing an optically active amino acid represented by the general formula (10):

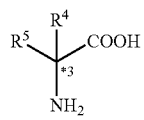
(10)

wherein, $R^4$ and $R^5$ are different and represent a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and *3 indicates an asymmetric carbon atom, comprising a steps of removing the substituent group on the nitrogen of the optically active imidazolidinone derivative represented by the general formula (3) to obtain an optically active amino acid amide represented by the general formula (12):

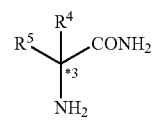
(12)

wherein, $R^4$, $R^5$ and *3 are the same as described above,
thereafter treating the amino acid amide with an acid or a base in at least one of organic solvents and water.

16. A method of producing an optically active N-(1-substituted phenylethyl)amino acid derivative represented by the general formula (9):

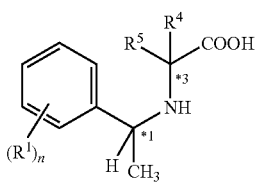
(9)

wherein, n represents an integer of 0 to 5 representively indicating the numbers of substituent groups $R^1$ on the benzene ring; $R^1$ represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$, the plural $R^1$ may be all the same or different; $R^4$ and $R^5$ are different and represent a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and *1 and *3 indicate asymmetric carbon atoms, comprising a step of treating an optically active imidazolidinone derivative represented by the general formula (3):

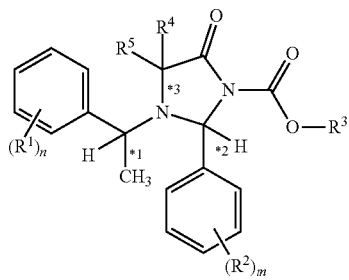
(3)

wherein, n, $R^1$, $R^4$, $R^5$, *1 and *3 are the same as described above; m represents an integer of 0 to 5 representively indicating the numbers of substituent groups $R^2$ on the benzene ring; $R^2$ represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^2$, the plural $R^2$ may be all the same or different; $R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aryl group having 6 to 18 carbon atoms, or an optionally substituted aralkyl group having 7 to 18 carbon atoms; and *2 indicates an asymmetric carbon atom, with an acid or a base in a solvent containing at least one kind of organic solvents and water, wherein the optically active imidazolidinone derivative represented by the general formula (3) is produced by the method according to claim 10.

17. A method of producing an optically active imidazolidinone derivative represented by the general formula (14):

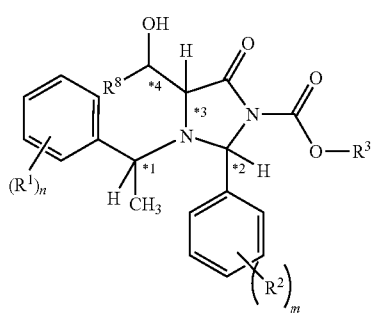
(14)

wherein, n and m independently represents an integer of 0 to 5 representively indicating the numbers of substituent groups $R^1$ and $R^2$ on the benzene rings; $R^1$ and $R^2$ independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of $R^1$ or $R^2$, the plural $R^1$ or $R^2$ may be all the same or different; $R^3$ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; *1, *2 and *3 indicate asymmetric carbon atoms; $R^8$ represents a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; and when $R^8$ is not a hydrogen atom, *4 indicates an asymmetric carbon atom, comprising a step of reacting an optically active imidazolidinone derivative represented by the general formula (2):

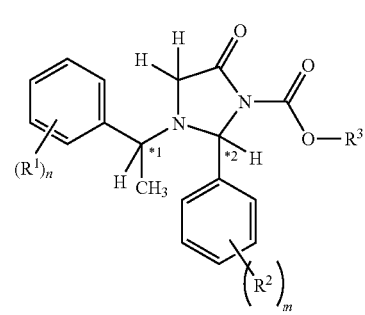
(2)

wherein, n, m, $R^1$, $R^2$, $R^3$, *1 and *2 are the same as described above, with an aldehyde represented by the general formula (13):

$R^8$-CHO (13)

wherein, $R^8$ is the same as described above, in the presence of a base.

18. The method of producing an optically active imidazolidinone derivative according to claim 17, wherein the base to be used is at least one of lithium diisopropylamide, lithium hexamethyldisilazide, sodium hexamethyldisilazide, potassium hexamethyldisilazide, t-butyl magnesium chloride, potassium t-butoxide, sodium t-butoxide, lithium t-butoxide, lithium hydride, sodium hydride, potassium hydride and calcium hydride.

19. The production method according to claim 17, wherein a compound represented by the general formula (2):

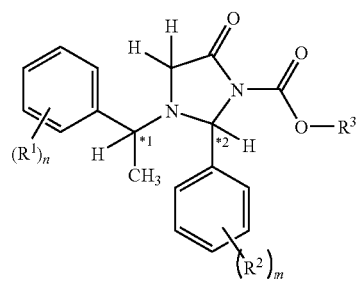
(2)

wherein, n, m, $R^1$, $R^2$, $R^3$, *1 and *2 are the same as described above, is obtained by reacting an imidazolidinone derivative or an optically active form thereof, represented by the general formula (1):

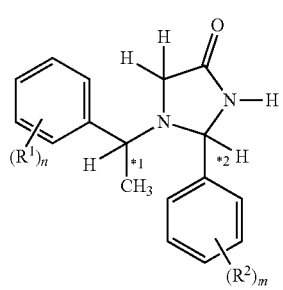
(1)

wherein, n, m, R¹, R², *1 and *2 are the same as described above, with a halogenoformic acid ester represented by the general formula (6):

$$R^3OCOX \quad (6)$$

wherein, R³ is the same as described above; and X represents a halogen atom, or a pyrocarbonic acid ester represented by the general formula (7):

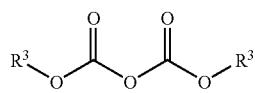

(7)

wherein, R³ is the same as descried above and two R³ are the same, in the presence of a base.

20. A method of producing an optically active N-(1-substituted phenylethyl)hydroxyamino acid derivative represented by the general formula (15):

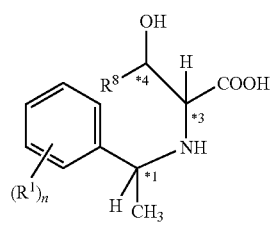

(15)

wherein, n represents an integer of 0 to 5 representively indicating the numbers of substituent groups R¹ on the benzene ring; R¹ represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R¹, the plural R¹ may be all the same or different; R⁸ represents a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; *1 and *3 indicate asymmetric carbon atoms; and when R⁸ is not a hydrogen atom, *4 indicates an asymmetric carbon atom, comprising a step of treating an optically active imidazolidinone derivative represented by the general formula (14):

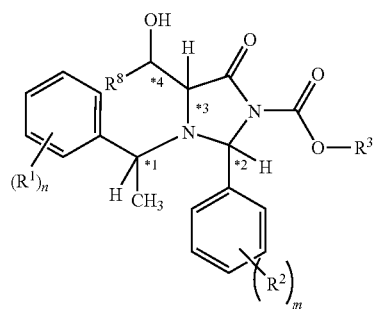

(14)

wherein, n, R¹, R⁸, *1, *3, and *4 are the same as described above; m represents an integer of 0 to 5 representively indicating the numbers of substituent groups R² on the benzene ring; R² represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R², the plural R² may be all the same or different; R³ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; *2 indicates an asymmetric carbon atom, with an acid or a base in at least one of organic solvents and water.

21. A method of producing an optically active hydroxyamino acid represented by the general formula (16):

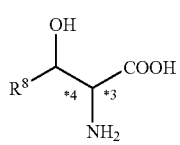

(16)

wherein, R⁸, *3 and *4 are the same as described above, comprising a step of removing the substituent group on the nitrogen of the hydroxyamino acid derivative represented by the general formula (15) and obtained according to claim 20.

22. A method of producing an optically active hydroxyamino acid represented by the general formula (16):

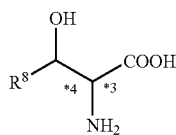

(16)

wherein, R⁸ represents a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; *3 indicates an asymmetric carbon atom; and when R⁸ is not a hydrogen atom, *4 indicates an asymmetric carbon atom, comprising steps of removing the ptotective substituent group on the nitrogen of the optically active imidazolidinone derivative represented by the general formula (14):

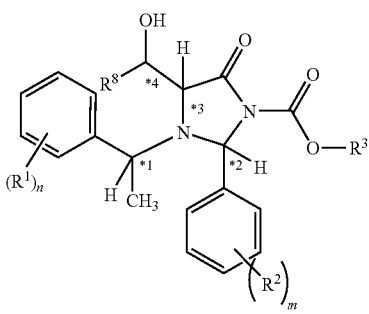
(14)

wherein, n, R⁸, *3 and *4 are the same as described above; m independently represents an integer of 0 to 5 representively indicating the numbers of substituent groups R¹ and R² on the benzene rings; R¹ and R² independently represent an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R¹ or R², the plural R¹ or R² may be all the same or different; R³ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; *1 and *2 indicate asymmetric carbon atoms, to synthesize an optically active hydroxyamino acid amide represented by the general formula (17):

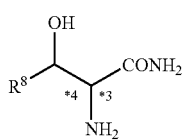
(17)

wherein, R⁸, *3 and *4 are the same as described above; thereafter treating the hydroxyamino acid amide with an acid or a base in at least one of organic solvents and water.

23. A method of producing an optically active N-(1-substituted phenylethyl)hydroxyamino acid derivative represented by the general formula (15):

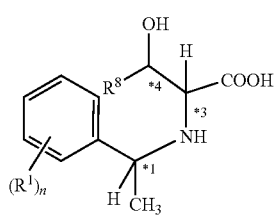
(15)

wherein, n represents an integer of 0 to 5 representively indicating the numbers of substituent groups R¹ on the benzene ring; R¹ represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R¹, the plural R¹ may be all the same or different; R⁸ represents a hydrogen atom, an optionally substituted alkyl group having 1 to 30 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; *1 and *3 indicate asymmetric carbon atoms; and when R⁸ is not a hydrogen atom, *4 indicates an asymmetric carbon atom, comprising a step of treating an optically active imidazolidinone derivative represented by the general formula (14):

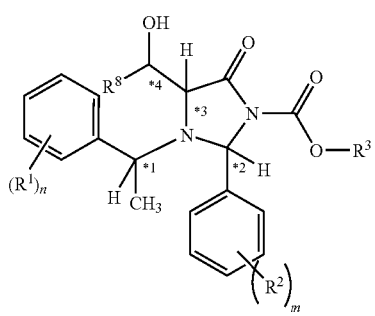
(14)

wherein, n, R¹, R⁸, *1, *3, and *4 are the same as described above; m represents an integer of 0 to 5 representively indicating the numbers of substituent groups R² on the benzene ring; R² represents an optionally substituted alkyl group having 1 to 18 carbon atoms, an optionally substituted aralkyl group having 7 to 18 carbon atoms, an optionally substituted aryl group having 6 to 18 carbon atoms, a halogen atom, a hydroxyl group, an optionally substituted alkoxy group having 1 to 18 carbon atoms, or a nitro group; in case that there are a plurality of R², the plural R² may be all the same or different; R³ represents an optionally substituted alkyl group having 1 to 18 carbon atoms, an optionally substituted alkenyl group having 2 to 18 carbon atoms, an optionally substituted alkynyl group having 2 to 18 carbon atoms, an optionally substituted aralkyl group having 7 to 18 carbon atoms, or an optionally substituted aryl group having 6 to 18 carbon atoms; *2 indicates an asymmetric carbon atom, with an acid or a base in at least one of organic solvents and water, wherein the optically active imidazolidinone derivative represented by the general formula (14) is obtained by the method according to claim 17.

\* \* \* \* \*